US012239558B2

(12) United States Patent
Schreck et al.

(10) Patent No.: US 12,239,558 B2
(45) Date of Patent: Mar. 4, 2025

(54) CATHETER SYSTEM AND METHODS OF USING SAME

(71) Applicant: Endologix LLC, Irvine, CA (US)

(72) Inventors: Stefan Schreck, Fallbrook, CA (US); Elbert Tzeng, Irvine, CA (US); Todd Abraham, Mission Viejo, CA (US); Jonathan Phan, Garden Grove, CA (US); Joshua Benjamin, Aliso Viejo, CA (US); Jacqueline Macias, South Gate, CA (US); Kevin Chu, Tustin, CA (US); Bill Gould, Fallbrook, CA (US)

(73) Assignee: Endologix LLC, Irvine, CA (US)

( * ) Notice: Subject to any disclaimer, the term of this patent is extended or adjusted under 35 U.S.C. 154(b) by 1054 days.

(21) Appl. No.: 16/881,620

(22) Filed: May 22, 2020

(65) Prior Publication Data

US 2020/0281751 A1  Sep. 10, 2020

Related U.S. Application Data

(60) Continuation of application No. 15/632,064, filed on Jun. 23, 2017, now Pat. No. 10,660,775, which is a
(Continued)

(51) Int. Cl.
*A61F 2/966* (2013.01)
*A61F 2/07* (2013.01)
(Continued)

(52) U.S. Cl.
CPC .............. *A61F 2/966* (2013.01); *A61F 2/07* (2013.01); *A61F 2/90* (2013.01); *A61F 2/954* (2013.01);
(Continued)

(58) Field of Classification Search
CPC ...... A61F 2002/9505; A61F 2002/9511; A61F 2002/9665; A61F 2/95; A61F 2/954;
(Continued)

(56) References Cited

U.S. PATENT DOCUMENTS 519,928 A    5/1894  Schanck
1,065,935 A   7/1913  Gail
(Continued)

FOREIGN PATENT DOCUMENTS

CA    2220141    11/1996
CA    2287406    12/1997
(Continued)

OTHER PUBLICATIONS

US 5,690,647 A, 11/1997, Osborne (withdrawn)
(Continued)

*Primary Examiner* — Ryan J. Severson
(74) *Attorney, Agent, or Firm* — Foley & Lardner LLP

(57) ABSTRACT

A modular catheter system including a sheath projecting distally from a delivery catheter having a main body module An inner core module carrying a stent thereon, the inner core being axially movable through the main body of the delivery catheter and the delivery catheter sheath, a handle member supported by the main body of the delivery catheter, the handle member being selectively axially engageable with the inner core such that the handle member and the inner core move together in an axial direction when the handle member is engaged with the inner core; and an adjustment member supported by the main body, the adjustment member being configured such that rotation of the adjustment member causes the adjustment member to move axially along the main body by either axially sliding the handle member relative to the main body or by rotating the adjustment member.

18 Claims, 32 Drawing Sheets

Related U.S. Application Data continuation of application No. 15/379,268, filed on Dec. 14, 2016, now Pat. No. 9,687,374, which is a continuation of application No. 14/462,485, filed on Aug. 18, 2014, now Pat. No. 9,549,835, which is a division of application No. 13/408,952, filed on Feb. 29, 2012, now Pat. No. 8,808,350.

(60) Provisional application No. 61/448,154, filed on Mar. 1, 2011.

(51) Int. Cl.
    *A61F 2/90*      (2013.01)
    *A61F 2/954*      (2013.01)
    *A61M 25/00*      (2006.01)
    *A61M 25/06*      (2006.01)
    *A61F 2/95*      (2013.01)
    *A61M 25/09*      (2006.01)

(52) U.S. Cl.
CPC .... *A61M 25/0097* (2013.01); *A61M 25/0662* (2013.01); *A61F 2/9517* (2020.05); *A61F 2002/9665* (2013.01); *A61M 2025/09125* (2013.01)

(58) Field of Classification Search
CPC .. A61F 2/962; A61F 2/966; A61F 2/97; A61F 2/9517; A61M 25/0097; A61M 2025/09116
See application file for complete search history.

(56) References Cited

U.S. PATENT DOCUMENTS

| | | |
|---|---|---|
| 2,127,903 A | 8/1938 | Bowen |
| 2,335,333 A | 11/1943 | Wysong |
| 2,437,542 A | 5/1944 | Krippendorf |
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,245,703 A | 4/1966 | Manly |
| 3,805,301 A | 4/1974 | Liebig |
| 3,994,149 A | 11/1976 | Dahlman |
| 4,362,156 A | 12/1982 | Feller, Jr. et al. |
| 4,473,067 A | 9/1984 | Schiff |
| 4,497,074 A | 2/1985 | Ray et al. |
| 4,501,263 A | 2/1985 | Harbuck |
| 4,503,568 A | 3/1985 | Madras |
| 4,525,157 A | 6/1985 | Vaillancourt |
| 4,562,596 A | 1/1986 | Kornberg |
| 4,580,568 A | 4/1986 | Gianturco |
| 4,592,754 A | 6/1986 | Gupte et al. |
| 4,617,932 A | 10/1986 | Kornberg |
| 4,723,550 A | 2/1988 | Bales et al. |
| 4,723,938 A | 2/1988 | Goodin et al. |
| 4,756,307 A | 7/1988 | Crownshield |
| 4,768,507 A | 9/1988 | Fischell et al. |
| 4,772,266 A | 9/1988 | Groshong |
| 4,795,465 A | 1/1989 | Marten |
| 4,800,882 A | 1/1989 | Gianturco |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,917,668 A | 4/1990 | Haindl |
| 4,922,905 A | 5/1990 | Strecker |
| 4,960,412 A | 10/1990 | Fink |
| 4,978,334 A | 12/1990 | Toye et al. |
| 4,981,478 A | 1/1991 | Evard et al. |
| 4,981,947 A | 1/1991 | Tomagou et al. |
| 4,994,069 A | 2/1991 | Ritchrt et al. |
| 4,994,071 A | 2/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,064,414 A | 11/1991 | Revane |
| 5,064,435 A | 11/1991 | Porter |
| 5,078,726 A | 1/1992 | Kreamer |
| 5,084,010 A | 1/1992 | Plaia et al. |
| 5,098,392 A | 3/1992 | Fleischhacker et al. |
| 5,098,395 A | 3/1992 | Fields |
| 5,104,399 A | 4/1992 | Lazarus |
| 5,108,380 A | 4/1992 | Herlitze et al. |
| 5,108,424 A | 4/1992 | Hoffman, Jr. et al. |
| 5,116,349 A | 5/1992 | Aranyi |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,137,519 A | 8/1992 | Littrell et al. |
| 5,141,497 A | 8/1992 | Erskine |
| 5,151,105 A | 9/1992 | Kwan-Gett |
| 5,156,619 A | 10/1992 | Ehrenfeld |
| 5,178,634 A | 1/1993 | Martinez |
| 5,186,712 A | 2/1993 | Kelso et al. |
| 5,195,978 A | 3/1993 | Schiffer |
| 5,195,980 A | 3/1993 | Catlin |
| 5,197,976 A | 3/1993 | Herweck et al. |
| 5,201,757 A | 4/1993 | Heyn et al. |
| 5,203,774 A | 4/1993 | Gilson et al. |
| 5,205,829 A | 4/1993 | Lituchy |
| 5,211,658 A | 5/1993 | Clouse |
| 5,222,969 A | 6/1993 | Gillis |
| 5,250,036 A | 10/1993 | Farivar |
| 5,256,141 A | 10/1993 | Gencheff et al. |
| 5,263,932 A | 11/1993 | Jang |
| 5,267,982 A | 12/1993 | Sylvanowicz |
| 5,275,622 A | 1/1994 | Lazarus et al. |
| 5,279,592 A | 1/1994 | Amor et al. |
| 5,282,824 A | 2/1994 | Gianturco |
| 5,282,860 A | 2/1994 | Matsuno et al. |
| 5,290,310 A | 3/1994 | Makower et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpeil |
| 5,324,306 A | 6/1994 | Makower et al. |
| 5,330,500 A | 7/1994 | Song |
| 5,334,157 A | 8/1994 | Klein et al. |
| 5,342,387 A | 8/1994 | Summers |
| 5,350,397 A | 9/1994 | Palermo et al. |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,376,077 A | 12/1994 | Gomringer |
| 5,383,892 A | 1/1995 | Cardon et al. |
| 5,387,235 A | 2/1995 | Chuter |
| 5,389,087 A | 2/1995 | Miraki |
| 5,391,152 A | 2/1995 | Patterson |
| 5,397,310 A | 3/1995 | Chu et al. |
| 5,397,355 A | 3/1995 | Marin et al. |
| 5,403,283 A | 4/1995 | Luther |
| 5,403,341 A | 4/1995 | Solar |
| 5,405,323 A | 4/1995 | Rogers et al. |
| 5,405,377 A | 4/1995 | Cragg |
| 5,405,378 A | 4/1995 | Strecker |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |
| 5,443,500 A | 8/1995 | Sigwart |
| 5,453,090 A | 9/1995 | Martinez et al. |
| 5,456,713 A | 10/1995 | Chuter |
| 5,458,615 A | 10/1995 | Klemm et al. |
| 5,462,530 A | 10/1995 | Jang |
| 5,464,449 A | 11/1995 | Ryan et al. |
| 5,464,450 A | 11/1995 | Buscemi et al. |
| 5,464,499 A | 11/1995 | Moslehi et al. |

(56) References Cited

U.S. PATENT DOCUMENTS

| | | |
|---|---|---|
| 5,472,417 A | 12/1995 | Martin et al. |
| 5,484,444 A | 1/1996 | Braunschweiler et al. |
| 5,489,295 A | 2/1996 | Piplani et al. |
| 5,496,365 A | 3/1996 | Sgro |
| 5,505,710 A | 4/1996 | Dorsey, III |
| 5,507,727 A | 4/1996 | Crainich |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,152 A | 8/1996 | Funderburk et al. |
| 5,545,211 A | 8/1996 | An et al. |
| 5,549,635 A | 8/1996 | Solar |
| 5,545,118 A | 9/1996 | Jang |
| 5,554,118 A | 9/1996 | Jang |
| 5,554,181 A | 9/1996 | Das |
| 5,562,697 A | 10/1996 | Christiansen |
| 5,562,726 A | 10/1996 | Chuter |
| 5,562,728 A | 10/1996 | Lazarus et al. |
| 5,571,169 A | 11/1996 | Plaia et al. |
| 5,571,172 A | 11/1996 | Chin |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,195 A | 1/1997 | Taheri et al. |
| 5,591,197 A | 1/1997 | Orth et al. |
| 5,591,198 A | 1/1997 | Boyle et al. |
| 5,591,226 A | 1/1997 | Trerotola et al. |
| 5,591,228 A | 1/1997 | Edoga |
| 5,591,229 A | 1/1997 | Parodi |
| 5,591,230 A | 1/1997 | Horn et al. |
| 5,593,417 A | 1/1997 | Rhodes |
| 5,599,305 A | 2/1997 | Hermann et al. |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,755 A | 5/1997 | Heller et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,634,928 A | 6/1997 | Fischell et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,653,748 A | 8/1997 | Strecker |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,671 A | 10/1997 | Inoue |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,697,971 A | 12/1997 | Fischell et al. |
| 5,700,269 A | 12/1997 | Pinchuk et al. |
| 5,707,354 A | 1/1998 | Salmon et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,725,519 A | 3/1998 | Penner et al. |
| 5,733,267 A | 3/1998 | Del Toro |
| 5,733,325 A | 3/1998 | Robinson et al. |
| 5,738,660 A | 4/1998 | Luther |
| 5,738,674 A | 4/1998 | Williams et al. |
| 5,741,233 A | 4/1998 | Riddle et al. |
| 5,746,766 A | 5/1998 | Edoga |
| 5,746,776 A | 5/1998 | Smith et al. |
| 5,749,880 A | 5/1998 | Banas et al. |
| 5,749,921 A | 5/1998 | Lenker et al. |
| 5,755,735 A | 5/1998 | Richter et al. |
| 5,755,770 A | 5/1998 | Ravenscroft |
| 5,755,771 A | 5/1998 | Penn et al. |
| 5,755,777 A | 5/1998 | Chuter |
| 5,765,682 A | 6/1998 | Bley et al. |
| 5,766,203 A | 6/1998 | Imran et al. |
| 5,769,885 A | 6/1998 | Quiachon et al. |
| 5,769,887 A | 6/1998 | Brown et al. |
| 5,772,636 A | 6/1998 | Brimhall et al. |
| 5,776,142 A | 7/1998 | Gunderson |
| 5,782,807 A | 7/1998 | Falvai et al. |
| 5,782,817 A | 7/1998 | Franzel et al. |
| 5,782,855 A | 7/1998 | Lau et al. |
| 5,782,909 A | 7/1998 | Quiachon et al. |
| 5,788,707 A | 8/1998 | Del Toro et al. |
| 5,797,952 A | 8/1998 | Klein |
| 5,800,456 A | 9/1998 | Maeda et al. |
| 5,800,508 A | 9/1998 | Goicoechea et al. |
| 5,800,517 A | 9/1998 | Anderson et al. |
| 5,800,526 A | 9/1998 | Anderson et al. |
| 5,800,540 A | 9/1998 | Chin |
| 5,810,836 A | 9/1998 | Hussein et al. |
| 5,810,873 A | 9/1998 | Morales |
| 5,817,100 A | 10/1998 | Igaki |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,053 A | 10/1998 | Khosravi et al. |

(56) References Cited

U.S. PATENT DOCUMENTS

| | | |
|---|---|---|
| 5,843,046 A | 12/1998 | Motisi et al. |
| 5,843,092 A | 12/1998 | Heller et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,860,998 A | 1/1999 | Robinson et al. |
| 5,865,844 A | 2/1999 | Plaia et al. |
| 5,867,432 A | 2/1999 | Toda |
| 5,868,783 A | 2/1999 | Tower |
| 5,871,536 A | 2/1999 | Lazarus |
| 5,876,432 A | 3/1999 | Lau et al. |
| 5,879,321 A | 3/1999 | Hill |
| 5,879,333 A | 3/1999 | Smith |
| 5,879,334 A | 3/1999 | Brimhall |
| 5,879,366 A | 3/1999 | Shaw et al. |
| 5,885,217 A | 3/1999 | Gisselberg et al. |
| 5,891,193 A | 4/1999 | Robinson et al. |
| 5,893,868 A | 4/1999 | Hanson et al. |
| 5,893,887 A | 4/1999 | Jayaraman |
| 5,902,334 A | 5/1999 | Dwyer et al. |
| 5,906,619 A | 5/1999 | Olson et al. |
| 5,906,640 A | 5/1999 | Penn et al. |
| 5,906,641 A | 5/1999 | Thompson et al. |
| 5,910,145 A | 6/1999 | Fischell et al. |
| 5,911,700 A | 6/1999 | Mozsary et al. |
| 5,911,710 A | 6/1999 | Barry et al. |
| 5,911,752 A | 6/1999 | Dustrude et al. |
| 5,916,263 A | 6/1999 | Goicocehea et al. |
| 5,919,225 A | 7/1999 | Lau et al. |
| 5,925,075 A | 7/1999 | Myers et al. |
| 5,925,076 A | 7/1999 | Inoe |
| 5,928,279 A | 7/1999 | Shannon et al. |
| 5,935,135 A | 8/1999 | Bramfitt et al. |
| 5,935,161 A | 8/1999 | Robinson et al. |
| 5,938,696 A | 8/1999 | Goicoechea et al. |
| 5,948,018 A | 9/1999 | Dereume et al. |
| 5,954,729 A | 9/1999 | Bachmann et al. |
| 5,957,973 A | 9/1999 | Quiachon et al. |
| 5,961,546 A | 10/1999 | Robinson et al. |
| 5,961,548 A | 10/1999 | Shmulewitz |
| 5,971,958 A | 10/1999 | Zhang |
| 5,976,153 A | 11/1999 | Fischell et al. |
| 5,976,155 A | 11/1999 | Foreman et al. |
| 5,997,562 A | 12/1999 | Zadno-Azizi et al. |
| 6,001,125 A | 12/1999 | Golds et al. |
| 6,004,294 A | 12/1999 | Brimhall et al. |
| 6,004,347 A | 12/1999 | McNamara et al. |
| 6,004,348 A | 12/1999 | Banas et al. |
| 6,017,363 A | 1/2000 | Hojeibane |
| 6,019,777 A | 2/2000 | Mackenzie |
| 6,019,785 A | 2/2000 | Strecker |
| 6,027,508 A | 2/2000 | Ren et al. |
| 6,027,779 A | 2/2000 | Campbell et al. |
| 6,027,811 A | 2/2000 | Campbell et al. |
| 6,030,414 A | 2/2000 | Taheri |
| 6,030,415 A | 2/2000 | Chuter |
| 6,033,413 A | 3/2000 | Mikus et al. |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,059,824 A | 5/2000 | Taheri |
| 6,063,092 A | 5/2000 | Shin |
| 6,063,113 A | 5/2000 | Kavteladze et al. |
| 6,068,635 A | 5/2000 | Gianotti |
| 6,070,589 A | 6/2000 | Keith et al. |
| 6,074,398 A | 6/2000 | Leschinsky |
| 6,077,295 A | 6/2000 | Limon et al. |
| 6,077,296 A | 6/2000 | Shokoohi et al. |
| 6,077,297 A | 6/2000 | Robinson et al. |
| 6,080,191 A | 6/2000 | Summers |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,005 A | 8/2000 | Botich et al. |
| 6,096,027 A | 8/2000 | Layne |
| 6,106,548 A | 8/2000 | Reubin et al. |
| 6,110,180 A | 8/2000 | Foreman et al. |
| 6,113,607 A | 9/2000 | Lau et al. |
| 6,117,142 A | 9/2000 | Goodson et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,132,458 A | 10/2000 | Stachle et al. |
| 6,139,532 A | 10/2000 | Howell et al. |
| 6,143,016 A | 11/2000 | Bleam et al. |
| 6,146,389 A | 11/2000 | Geitz |
| 6,146,415 A | 11/2000 | Fitz |
| 6,149,680 A | 11/2000 | Shelso et al. |
| 6,152,944 A | 11/2000 | Holman et al. |
| 6,159,195 A | 12/2000 | Ha et al. |
| 6,159,198 A | 12/2000 | Gardeski et al. |
| 6,162,237 A | 12/2000 | Chan |
| 6,165,195 A | 12/2000 | Wilson et al. |
| 6,165,214 A | 12/2000 | Lazarus |
| 6,168,610 B1 | 1/2001 | Marin et al. |
| 6,171,281 B1 | 1/2001 | Zhang |
| 6,174,327 B1 | 1/2001 | Mertens et al. |
| 6,174,329 B1 | 1/2001 | Mertens et al. |
| 6,183,443 B1 | 2/2001 | Kratoska et al. |
| 6,183,481 B1 | 2/2001 | Lee et al. |
| 6,183,509 B1 | 2/2001 | Dibie |
| 6,187,036 B1 | 2/2001 | Shaolian et al. |
| 6,187,037 B1 | 2/2001 | Satz |
| 6,192,944 B1 | 2/2001 | Greenhalgh |
| 6,193,726 B1 | 2/2001 | Vanney |
| 6,197,007 B1 | 3/2001 | Thorne et al. |
| 6,197,016 B1 | 3/2001 | Fourkas et al. |
| 6,197,049 B1 | 3/2001 | Shaolian et al. |
| 6,203,735 B1 | 3/2001 | Edwin et al. |
| 6,210,429 B1 | 4/2001 | Vardi et al. |
| 6,214,038 B1 | 4/2001 | Piplani et al. |
| 6,221,081 B1 | 4/2001 | Mikus et al. |
| 6,221,090 B1 | 4/2001 | Wilson |
| 6,221,098 B1 | 4/2001 | Wilson |
| 6,221,102 B1 | 4/2001 | Baker et al. |
| 6,224,627 B1 | 5/2001 | Armstrong et al. |
| 6,228,062 B1 | 5/2001 | Howell et al. |
| 6,231,563 B1 | 5/2001 | White et al. |
| 6,238,410 B1 | 5/2001 | Vrba et al. |
| 6,254,609 B1 | 7/2001 | Vrba et al. |
| 6,254,628 B1 | 7/2001 | Wallace et al. |
| 6,258,099 B1 | 7/2001 | Mareiro et al. |
| 6,261,316 B1 | 7/2001 | Shaolian et al. |
| 6,264,682 B1 | 7/2001 | Wilson et al. |
| 6,273,895 B1 | 8/2001 | Pinchuk et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,283,991 B1 | 9/2001 | Cox et al. |
| 6,287,329 B1 | 9/2001 | Duering et al. |
| 6,299,634 B1 | 10/2001 | Bergeron |
| 6,302,893 B1 | 10/2001 | Limon et al. |
| 6,312,406 B1 | 11/2001 | Jayaraman |
| 6,331,184 B1 | 12/2001 | Abrams |
| 6,331,190 B1 | 12/2001 | Shokoohi et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,544 B1 | 3/2002 | Wilson et al. |
| 6,361,555 B1 | 3/2002 | Wilson |

(56) References Cited

U.S. PATENT DOCUMENTS

| | | |
|---|---|---|
| 6,361,557 B1 | 3/2002 | Gittings et al. |
| 6,361,559 B1 | 3/2002 | Houser et al. |
| 6,361,637 B2 | 3/2002 | Martin et al. |
| 6,379,365 B1 | 4/2002 | Diaz |
| 6,380,457 B1 | 4/2002 | Yurek et al. |
| 6,383,213 B2 | 5/2002 | Wilson et al. |
| 6,387,120 B2 | 5/2002 | Wilson et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout et al. |
| 6,416,474 B1 | 7/2002 | Penner et al. |
| 6,416,529 B1 | 7/2002 | Holman et al. |
| 6,416,542 B1 | 7/2002 | Marcade et al. |
| 6,428,567 B2 | 8/2002 | Wilson et al. |
| 6,432,130 B1 | 8/2002 | Hanson |
| 6,432,131 B1 | 8/2002 | Ravenscroft |
| 6,432,134 B1 | 8/2002 | Anson et al. |
| 6,440,161 B1 | 8/2002 | Madrid et al. |
| 6,447,540 B1 | 9/2002 | Fontaine et al. |
| 6,451,043 B1 | 9/2002 | McInnes et al. |
| 6,464,721 B1 | 10/2002 | Marcade et al. |
| 6,468,298 B1 | 10/2002 | Pelton |
| 6,475,166 B1 | 11/2002 | Escano |
| 6,475,170 B1 | 11/2002 | Doron et al. |
| 6,478,777 B1 | 11/2002 | Honeck et al. |
| 6,482,211 B1 | 11/2002 | Choi |
| 6,485,513 B1 | 11/2002 | Fan |
| 6,491,719 B1 | 12/2002 | Fogrty et al. |
| 6,500,202 B1 | 12/2002 | Shaolian et al. |
| 6,508,790 B1 | 1/2003 | Lawrence |
| 6,508,833 B2 | 1/2003 | Pavcnick et al. |
| 6,508,835 B1 | 1/2003 | Shaolian et al. |
| 6,508,836 B1 | 1/2003 | Wilson et al. |
| 6,511,325 B1 | 1/2003 | Lalka et al. |
| 6,514,281 B1 | 2/2003 | Blaeser et al. |
| 6,517,522 B1 | 2/2003 | Bell et al. |
| 6,517,569 B2 | 2/2003 | Mikus et al. |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,554,848 B2 | 4/2003 | Boylan et al. |
| 6,558,396 B1 | 5/2003 | Inoue |
| 6,562,063 B1 | 5/2003 | Euteneurer et al. |
| 6,565,596 B1 | 5/2003 | White et al. |
| 6,565,597 B1 | 5/2003 | Fearnot et al. |
| 6,569,192 B1 | 5/2003 | Foreman et al. |
| RE38,146 E | 6/2003 | Palmaz et al. |
| 6,572,643 B1 | 6/2003 | Gharibadeh |
| 6,572,645 B2 | 6/2003 | Leonhardt |
| 6,576,005 B1 | 6/2003 | Geitz |
| 6,576,006 B2 | 6/2003 | Limon et al. |
| 6,576,009 B2 | 6/2003 | Ryan et al. |
| 6,579,312 B2 | 6/2003 | Wilson et al. |
| 6,582,390 B1 | 6/2003 | Sanderson |
| 6,582,394 B1 | 6/2003 | Reiss et al. |
| 6,582,459 B1 | 6/2003 | Lau et al. |
| 6,582,460 B1 | 6/2003 | Cryer |
| 6,585,758 B1 | 7/2003 | Chouinard et al. |
| 6,589,213 B2 | 7/2003 | Reydel |
| 6,589,251 B2 | 7/2003 | Yee et al. |
| 6,589,262 B1 | 7/2003 | Honebrink et al. |
| 6,592,548 B2 | 7/2003 | Jayaraman |
| 6,592,581 B2 | 7/2003 | Bowe |
| 6,592,614 B2 | 7/2003 | Lenker et al. |
| 6,592,615 B1 | 7/2003 | Marcade et al. |
| 6,599,315 B2 | 7/2003 | Wilson |
| 6,602,280 B2 | 8/2003 | Chobotov |
| 6,607,551 B1 | 8/2003 | Sullivan et al. |
| 6,607,552 B1 | 8/2003 | Hanson |
| 6,613,073 B1 | 9/2003 | White et al. |
| 6,613,075 B1 | 9/2003 | Healy et al. |
| 6,616,675 B1 | 9/2003 | Evard et al. |
| 6,620,191 B1 | 9/2003 | Svensson |
| 6,641,564 B1 | 11/2003 | Kraus |
| 6,652,492 B1 | 11/2003 | Bell et al. |
| 6,652,579 B1 | 11/2003 | Cox et al. |
| 6,656,213 B2 | 12/2003 | Solem |
| 6,660,030 B2 | 12/2003 | Shaolian et al. |
| 6,663,665 B2 | 12/2003 | Shaolian et al. |
| 6,669,716 B1 | 12/2003 | Gilson et al. |
| 6,669,718 B2 | 12/2003 | Besselink |
| 6,669,719 B2 | 12/2003 | Wallace et al. |
| 6,673,102 B1 | 1/2004 | Vonesh et al. |
| 6,676,666 B2 | 1/2004 | Vrba et al. |
| 6,676,667 B2 | 1/2004 | Mareiro et al. |
| 6,689,157 B2 | 2/2004 | Madrid et al. |
| 6,699,274 B2 | 3/2004 | Stinson |
| 6,699,275 B1 | 3/2004 | Knudson et al. |
| 6,702,843 B1 | 3/2004 | Brown et al. |
| 6,702,845 B1 | 3/2004 | Cully et al. |
| 6,722,705 B2 | 4/2004 | Korkor |
| 6,723,075 B2 | 4/2004 | Davey et al. |
| 6,733,523 B2 | 5/2004 | Shaolian et al. |
| 6,743,210 B2 | 6/2004 | Hart et al. |
| 6,749,627 B2 | 6/2004 | Thompson et al. |
| 6,752,819 B1 | 6/2004 | Brady et al. |
| 6,755,855 B2 | 6/2004 | Yurek et al. |
| 6,761,733 B2 | 7/2004 | Chobotov et al. |
| 6,767,359 B2 | 7/2004 | Weadock |
| 6,790,224 B2 | 9/2004 | Gerberding |
| 6,792,979 B2 | 9/2004 | Konya et al. |
| 6,800,065 B2 | 10/2004 | Duane et al. |
| 6,808,509 B1 | 10/2004 | Davey |
| 6,808,520 B1 | 10/2004 | Fourkas et al. |
| 6,814,752 B1 | 11/2004 | Chuter |
| 6,818,014 B2 | 11/2004 | Brown et al. |
| 6,821,292 B2 | 11/2004 | Pazienza et al. |
| 6,827,726 B2 | 12/2004 | Parodi |
| 6,840,950 B2 | 1/2005 | Standford et al. |
| 6,846,316 B2 | 1/2005 | Abrams |
| 6,849,084 B2 | 2/2005 | Rabkin et al. |
| 6,849,086 B2 | 2/2005 | Cragg |
| 6,858,038 B2 | 2/2005 | Heuser |
| 6,866,669 B2 | 3/2005 | Buzzard et al. |
| 6,872,193 B2 | 3/2005 | Shaw et al. |
| 6,875,229 B2 | 4/2005 | Wilson et al. |
| 6,878,158 B2 | 4/2005 | Shin et al. |
| 6,887,249 B1 | 5/2005 | Houser et al. |
| 6,887,251 B1 | 5/2005 | Suval |
| 6,887,256 B2 | 5/2005 | Gilson et al. |
| 6,896,699 B2 | 5/2005 | Wilson et al. |
| 6,899,727 B2 | 5/2005 | Armstrong et al. |
| 6,899,728 B1 | 5/2005 | Phillips et al. |
| 6,908,477 B2 | 6/2005 | McGuckin |
| 6,911,039 B2 | 6/2005 | Shiu et al. |
| 6,918,925 B2 | 7/2005 | Tehrani |
| 6,923,829 B2 | 8/2005 | Boyle et al. |
| 6,926,732 B2 | 8/2005 | Derus et al. |
| 6,929,661 B2 | 8/2005 | Bolduc et al. |
| 6,932,837 B2 | 8/2005 | Amplatz et al. |
| 6,939,352 B2 | 9/2005 | Buzzard et al. |
| 6,939,368 B2 | 9/2005 | Simso |
| 6,939,370 B2 | 9/2005 | Hartley et al. |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,945,990 B2 | 9/2005 | Greenean |
| 6,953,475 B2 | 10/2005 | Shaolian et al. |
| 6,955,679 B1 | 10/2005 | Hendricksen et al. |
| 6,955,688 B2 | 10/2005 | Wilson et al. |
| 6,960,217 B2 | 11/2005 | Bolduc |
| 6,962,602 B2 | 11/2005 | Vardi |
| 6,981,982 B2 | 1/2006 | Armstrong et al. |
| 6,984,244 B2 | 1/2006 | Perez et al. |
| 6,991,639 B2 | 1/2006 | Holman et al. |

(56) References Cited

U.S. PATENT DOCUMENTS

| | | |
|---|---|---|
| 6,994,722 B2 | 2/2006 | DiCarlo |
| 7,004,926 B2 | 2/2006 | Navia et al. |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,022,133 B2 | 4/2006 | Yee et al. |
| 7,025,773 B2 | 4/2006 | Gittings et al. |
| 7,025,779 B2 | 4/2006 | Elliott |
| 7,029,496 B2 | 4/2006 | Rakos et al. |
| 7,052,511 B2 | 5/2006 | Weldon et al. |
| 7,056,323 B2 | 6/2006 | Mareiro et al. |
| 7,074,236 B2 | 7/2006 | Rabkin et al. |
| 7,096,554 B2 | 8/2006 | Austin et al. |
| 7,101,390 B2 | 9/2006 | Nelson |
| 7,105,016 B2 | 9/2006 | Shiu et al. |
| 7,105,017 B2 | 9/2006 | Kerr |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,127,789 B2 | 10/2006 | Stinson |
| 7,137,993 B2 | 11/2006 | Acosta et al. |
| 7,144,422 B1 | 12/2006 | Rao |
| 7,160,318 B2 | 1/2007 | Greenberg et al. |
| 7,162,302 B2 | 1/2007 | Wang et al. |
| 7,163,715 B1 | 1/2007 | Kramer |
| 7,172,577 B2 | 2/2007 | Mangano et al. |
| 7,175,651 B2 | 2/2007 | Kerr |
| 7,175,652 B2 | 2/2007 | Cook et al. |
| 7,175,657 B2 | 2/2007 | Khan et al. |
| 7,189,256 B2 | 3/2007 | Smith |
| 7,189,257 B2 | 3/2007 | Schmitt et al. |
| 7,201,770 B2 | 4/2007 | Johnson et al. |
| 7,229,472 B2 | 6/2007 | DePalma et al. |
| 7,235,095 B2 | 6/2007 | Haverkost et al. |
| 7,241,308 B2 | 7/2007 | Andreas et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,285,130 B2 | 10/2007 | Austin |
| 7,297,156 B2 | 11/2007 | Nelson |
| 7,300,454 B2 | 11/2007 | Park et al. |
| 7,314,481 B2 | 1/2008 | Karpiel |
| 7,314,483 B2 | 1/2008 | Landau et al. |
| 7,316,708 B2 | 1/2008 | Gordon et al. |
| 7,320,703 B2 | 1/2008 | DiMatteo et al. |
| 7,331,980 B2 | 2/2008 | Dubrul et al. |
| 7,367,980 B2 | 5/2008 | Kida et al. |
| 7,381,216 B2 | 6/2008 | Buzzard et al. |
| 7,402,168 B2 | 7/2008 | Acosta et al. |
| 7,407,509 B2 | 8/2008 | Greenberg et al. |
| 7,413,560 B2 | 8/2008 | Chong et al. |
| 7,419,501 B2 | 9/2008 | Chiu et al. |
| 7,425,219 B2 | 9/2008 | Quadri et al. |
| 7,435,253 B1 | 10/2008 | Hartley et al. |
| 7,473,271 B2 | 1/2009 | Gunderson |
| 7,476,244 B2 | 1/2009 | Buzzard et al. |
| 7,481,805 B2 | 1/2009 | Magnusson |
| 7,491,230 B2 | 2/2009 | Holman et al. |
| 7,520,895 B2 | 4/2009 | Douglas et al. |
| 7,526,849 B2 | 5/2009 | Serrano |
| 7,537,606 B2 | 5/2009 | Hartley |
| 7,553,324 B2 | 6/2009 | Andreas et al. |
| 7,572,289 B2 | 8/2009 | Sisken et al. |
| 7,578,838 B2 | 8/2009 | Melsheimer |
| 7,578,841 B2 | 8/2009 | Yadin et al. |
| 7,591,832 B2 | 9/2009 | Eversull et al. |
| 7,618,398 B2 | 11/2009 | Holman et al. |
| 7,632,299 B2 | 12/2009 | Weber |
| 7,635,382 B2 | 12/2009 | Pryor |
| 7,635,383 B2 | 12/2009 | Gumm |
| 7,637,932 B2 | 12/2009 | Bolduc et al. |
| 7,641,684 B2 | 1/2010 | Hilaire et al. |
| 7,651,519 B2 | 1/2010 | Dittman |
| 7,666,219 B2 | 2/2010 | Rasmussen et al. |
| 7,674,284 B2 | 3/2010 | Melsheimer |
| 7,678,141 B2 | 3/2010 | Greenan et al. |
| 7,691,135 B2 | 4/2010 | Shaolian et al. |
| 7,691,139 B2 | 4/2010 | Baker et al. |
| 7,695,508 B2 | 4/2010 | Der Leest et al. |
| 7,699,885 B2 | 4/2010 | Leonhardt et al. |
| 7,717,923 B2 | 5/2010 | Kennedy et al. |
| 7,722,657 B2 | 5/2010 | Hartley |
| 7,736,337 B2 | 6/2010 | Diep et al. |
| 7,736,383 B2 | 6/2010 | Bressler et al. |
| 7,736,384 B2 | 6/2010 | Bressler et al. |
| 7,753,951 B2 | 7/2010 | Shaked et al. |
| 7,758,625 B2 | 7/2010 | Wu et al. |
| 7,763,063 B2 | 7/2010 | Arbefeuille et al. |
| 7,766,952 B2 | 8/2010 | Horan et al. |
| 7,771,463 B2 | 8/2010 | Ton et al. |
| 7,785,340 B2 | 8/2010 | Heidner et al. |
| 7,785,361 B2 | 8/2010 | Nikolchev et al. |
| 7,794,473 B2 | 9/2010 | Tessmer et al. |
| 7,799,266 B2 | 9/2010 | Parker et al. |
| 7,833,259 B2 | 11/2010 | Boatman |
| 7,837,724 B2 | 11/2010 | Keeble et al. |
| 7,842,066 B2 | 11/2010 | Gilson et al. |
| 7,846,135 B2 | 12/2010 | Runfola |
| 7,867,267 B2 | 1/2011 | Sullivan et al. |
| 7,867,270 B2 | 1/2011 | Hartley |
| 7,871,419 B2 | 1/2011 | Devellian et al. |
| 7,871,430 B2 | 1/2011 | Pavcnik et al. |
| 7,879,081 B2 | 2/2011 | DeMatteo et al. |
| 7,883,537 B2 | 2/2011 | Grayzel et al. |
| 7,922,755 B2 | 4/2011 | Acosta et al. |
| 7,935,140 B2 | 5/2011 | Griffin |
| 7,942,924 B1 | 5/2011 | Perez et al. |
| 8,002,814 B2 | 8/2011 | Kennedy, II et al. |
| 8,021,420 B2 | 9/2011 | Dolan |
| 8,025,692 B2 | 9/2011 | Feeser |
| 8,034,100 B2 | 10/2011 | Shaolian et al. |
| 8,062,344 B2 | 11/2011 | Dorn et al. |
| 8,075,607 B2 | 12/2011 | Melsheimer |
| 8,075,608 B2 | 12/2011 | Gordon et al. |
| 8,092,508 B2 | 1/2012 | Leynov et al. |
| 8,167,892 B2 | 5/2012 | Feller, III et al. |
| 8,182,522 B2 | 5/2012 | Sarac et al. |
| 8,216,295 B2 | 7/2012 | Bemjamin et al. |
| 8,221,494 B2 | 7/2012 | Schreck et al. |
| 8,236,040 B2 | 8/2012 | Mayberry et al. |
| 8,357,192 B2 | 1/2013 | Mayberry et al. |
| 8,491,646 B2 | 7/2013 | Schreck |
| 8,523,931 B2 | 9/2013 | Mayberry et al. |
| 8,568,466 B2 | 10/2013 | Shaolian et al. |
| 8,808,350 B2 | 8/2014 | Schreck et al. |
| 8,821,564 B2 | 9/2014 | Schreck et al. |
| 8,844,430 B2 | 9/2014 | Mastropasqua et al. |
| 8,945,202 B2 | 2/2015 | Mayberry et al. |
| 9,549,835 B2* | 1/2017 | Schreck ............ A61M 25/0097 |
| 2005/0027305 A1 | 2/2005 | Shiu et al. |
| 2005/0038494 A1 | 2/2005 | Eidenschink |
| 2006/0229561 A1 | 10/2006 | Huszar |
| 2007/0168014 A1 | 7/2007 | Jimenez et al. |
| 2010/0004730 A1* | 1/2010 | Benjamin ......... A61M 25/0662 |
| | | 604/167.03 |
| 2011/0009945 A1 | 1/2011 | Parker et al. |
| 2011/0015728 A1 | 1/2011 | Jimenez et al. |
| 2011/0046712 A1 | 2/2011 | Melsheimer et al. |
| 2011/0054586 A1 | 3/2011 | Mayberry et al. |
| 2011/0054587 A1 | 3/2011 | Mayberry et al. |
| 2011/0121023 A1 | 5/2011 | Milan |
| 2011/0178588 A1 | 7/2011 | Haselby |
| 2011/0218607 A1 | 9/2011 | Arbefeuille et al. |
| 2011/0218617 A1 | 9/2011 | Nguyen |
| 2011/0224742 A1 | 9/2011 | Weisel et al. |
| 2011/0224782 A1 | 9/2011 | Douglas et al. |
| 2011/0251664 A1 | 10/2011 | Acosta De Acevedo |
| 2011/0257718 A1 | 10/2011 | Argentine |
| 2011/0270371 A1 | 11/2011 | Argentine |
| 2011/0282425 A1 | 11/2011 | Dwork |
| 2011/0313503 A1 | 12/2011 | Berra et al. |

(56) References Cited

U.S. PATENT DOCUMENTS

| | | |
|---|---|---|
| 2012/0109279 A1 | 5/2012 | Mayberry |
| 2012/0277847 A1 | 11/2012 | Benjamen |
| 2013/0184805 A1 | 7/2013 | Sawada |
| 2014/0358214 A1 | 12/2014 | Schreck et al. |

FOREIGN PATENT DOCUMENTS

| | | |
|---|---|---|
| DE | 295 21 548 U1 | 2/1995 |
| DE | 295 21 776 U1 | 2/1995 |
| DE | 100 17 147 | 10/2001 |
| EP | 0 177 330 | 6/1991 |
| EP | 0 564 373 | 10/1993 |
| EP | 0 596 145 | 5/1994 |
| EP | 0 621 015 | 10/1994 |
| EP | 0 659 389 | 6/1995 |
| EP | 0 688 545 | 12/1995 |
| EP | 0 689 806 | 1/1996 |
| EP | 0 712 614 | 5/1996 |
| EP | 0 732 088 | 9/1996 |
| EP | 0 740 928 A1 | 11/1996 |
| EP | 0 740 928 B1 | 11/1996 |
| EP | 0 747 020 | 12/1996 |
| EP | 0 775 470 | 5/1997 |
| EP | 0 782 841 | 7/1997 |
| EP | 0 783 873 | 7/1997 |
| EP | 0 783 874 | 7/1997 |
| EP | 0 875 262 | 11/1998 |
| EP | 0 880 938 | 12/1998 |
| EP | 0 880 948 | 12/1998 |
| EP | 0 904 745 | 3/1999 |
| EP | 0 974 314 | 1/2000 |
| EP | 1 358 903 | 11/2003 |
| EP | 1 508 313 | 2/2005 |
| EP | 2 680 915 | 1/2014 |
| ES | 1 038 606 | 7/1998 |
| GB | 1 193 759 | 6/1970 |
| JP | 04-25755 | 1/1992 |
| JP | H05-81257 | 11/1993 |
| JP | H623057 A | 2/1994 |
| JP | 30-09638 | 4/1994 |
| JP | 08-052165 | 2/1996 |
| JP | 08-336597 | 12/1996 |
| JP | 09-164209 | 6/1997 |
| JP | 9-511160 | 11/1997 |
| JP | 2000-500047 | 1/2000 |
| JP | 2004-130068 | 4/2004 |
| JP | 2010-536418 A | 12/2010 |
| WO | WO 90/14054 | 11/1990 |
| WO | WO 93/13825 | 7/1993 |
| WO | WO 94/24961 | 11/1994 |
| WO | WO 95/21592 | 8/1995 |
| WO | WO 96/14808 | 5/1996 |
| WO | WO 96/34580 | 11/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/17911 | 5/1997 |
| WO | WO 97/19652 | 6/1997 |
| WO | WO 97/26936 | 7/1997 |
| WO | WO 97/033532 | 9/1997 |
| WO | WO 97/045072 | 12/1997 |
| WO | WO 98/02100 | 1/1998 |
| WO | WO 98/53761 | 12/1998 |
| WO | WO-99/04728 A1 | 2/1999 |
| WO | WO 99/029262 | 6/1999 |
| WO | WO 99/44536 | 9/1999 |
| WO | WO 99/47077 | 9/1999 |
| WO | WO 99/58084 | 11/1999 |
| WO | WO 00/78248 | 12/2000 |
| WO | WO 02/36179 | 5/2002 |
| WO | WO 02/39888 | 5/2002 |
| WO | WO 02/060345 | 8/2002 |
| WO | WO 03/068302 | 8/2003 |
| WO | WO 05/037076 | 4/2005 |
| WO | WO 05/037141 | 4/2005 |
| WO | WO 05/067819 | 7/2005 |
| WO | WO 06/071915 | 7/2006 |
| WO | WO 06/117321 | 11/2006 |
| WO | WO 07/027830 | 3/2007 |
| WO | WO 07/092276 | 8/2007 |
| WO | WO 09/023221 | 2/2009 |
| WO | WO-2010/002931 A1 | 1/2010 |
| WO | WO 11/049808 | 4/2011 |
| WO | WO 12/118901 | 9/2012 |

OTHER PUBLICATIONS

US 6,413,270 B1, 07/2002, Thornton et al. (withdrawn)
U.S. Appl. No. 15/639,028, filed Jun. 20, 2017, Benjamin et al.
International Preliminary Report on Patentability, re PCT/US2012/027151, mailed Sep. 12, 2013, in 8 pages.
International Search Report and Written Opinion, re PCT/US2012/027151, mailed Jun. 26, 2012.
European Office Action dated Jun. 15, 2020, from application No. 12709432.4.
Chinese Office Action dated Dec. 10, 2014, from application No. 201280021287.5.
Chinese Office Action dated Jun. 9, 2017, from application No. 201510649289.4.
Chinese Office Action dated Nov. 16, 2017, from application No. 201510649289.4.
Chinese Office Action dated Oct. 27, 2016, from application No. 201510649289.4.
European Office Action dated Apr. 14, 2016, from application No. 12709432.4.
European Office Action dated Aug. 21, 2018, from application No. 12709432.4.
Japanese Notice of Reasons for Refusal dated Jan. 7, 2016, from application No. 2013-556828.
Japanese Notice of Reasons for Refusal dated Jul. 26, 2017, from application No. 2013-556828.
Japanese Notice of Reasons for Refusal dated Sep. 8, 2016, from application No. 2013-556828.
Non-final Office dated Sep. 12, 2019, from U.S. Appl. No. 15/632,064.
Notice of Allowance dated Apr. 14, 2014, from U.S. Appl. No. 13/408,952.
Notice of Allowance dated Feb. 28, 2017, from U.S. Appl. No. 15/379,268.
Notice of Allowance dated Jan. 22, 2020, from U.S. Appl. No. 15/632,064.
Notice of Allowance dated Sep. 21, 2016, from U.S. Appl. No. 14/462,485.

* cited by examiner

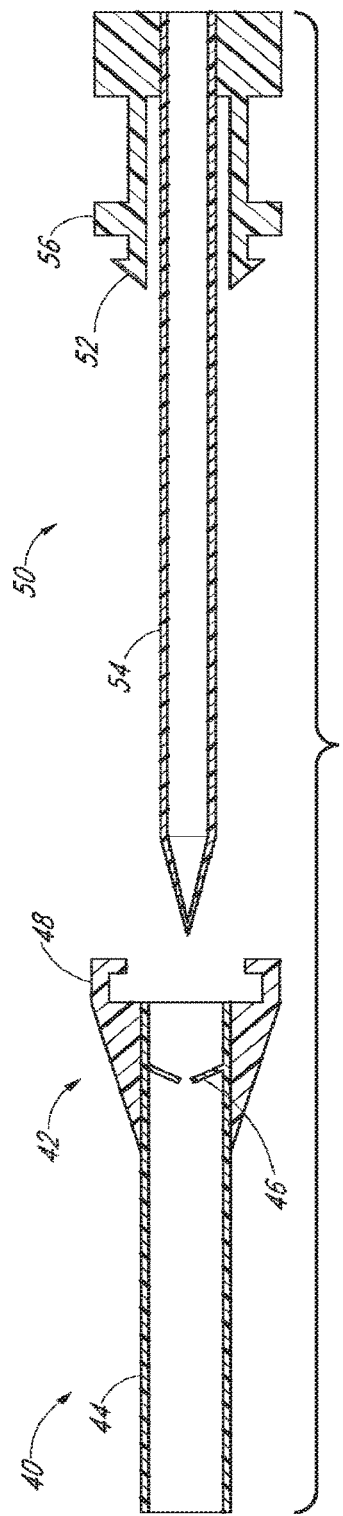
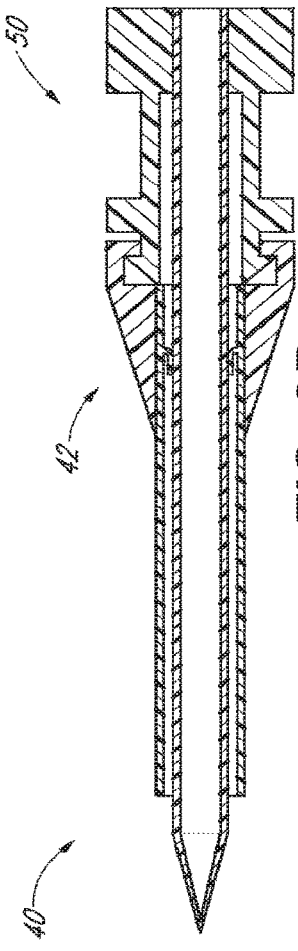
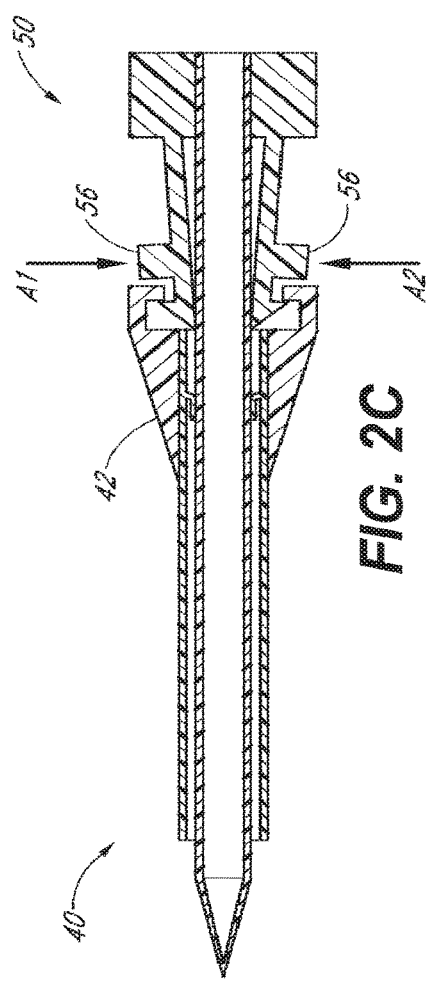
FIG. 2A
FIG. 2B
FIG. 2C

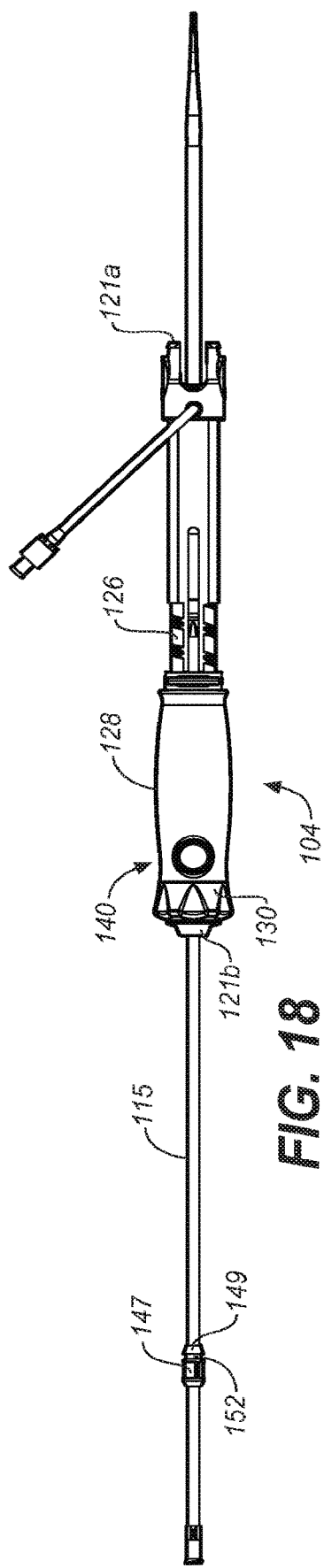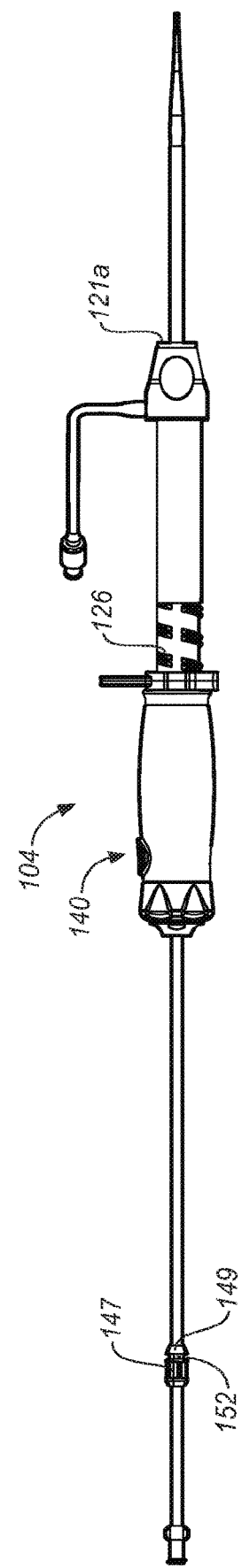
FIG. 18
FIG. 19

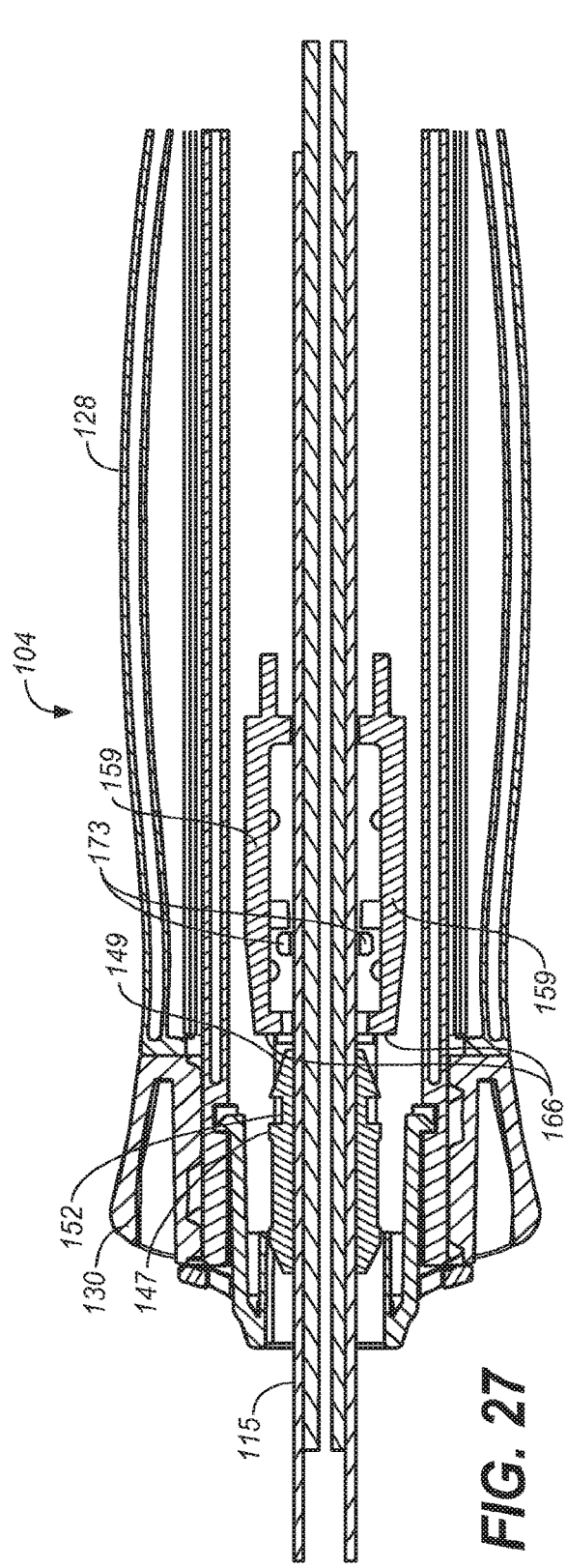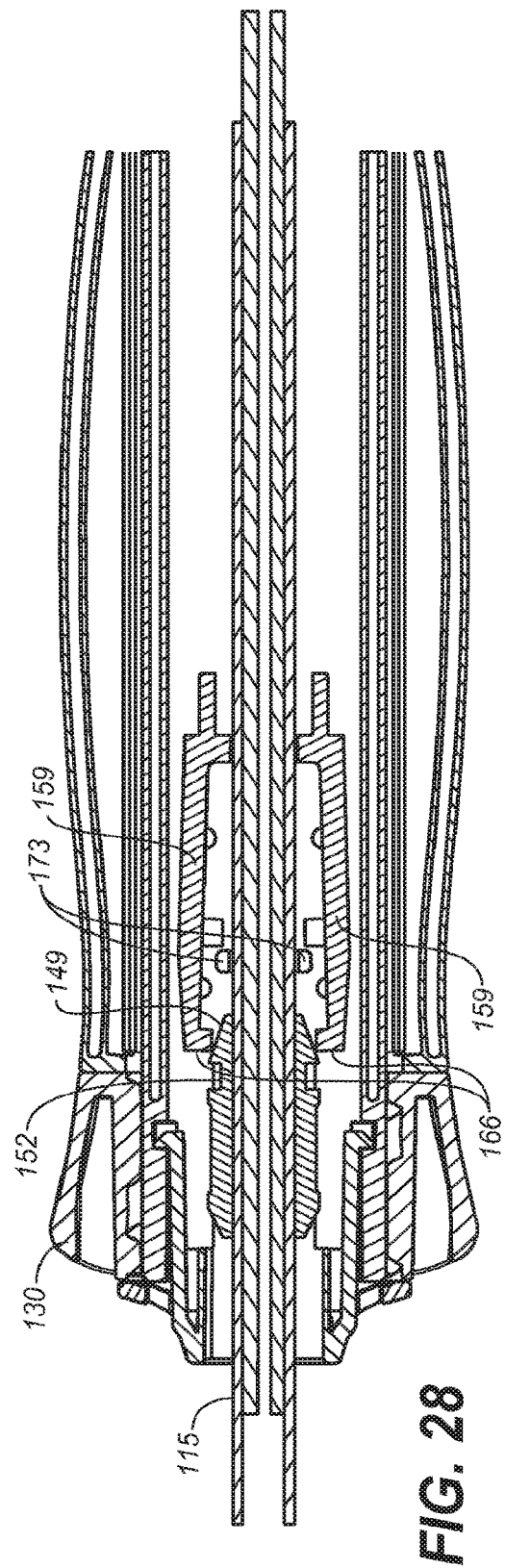

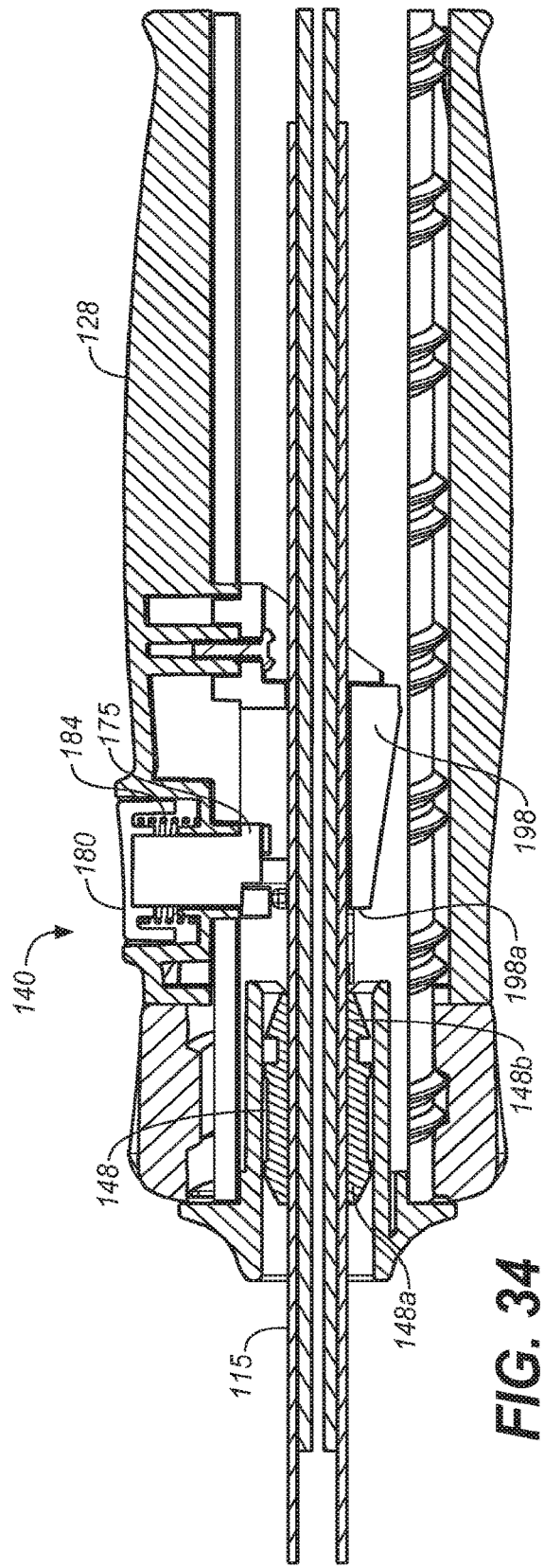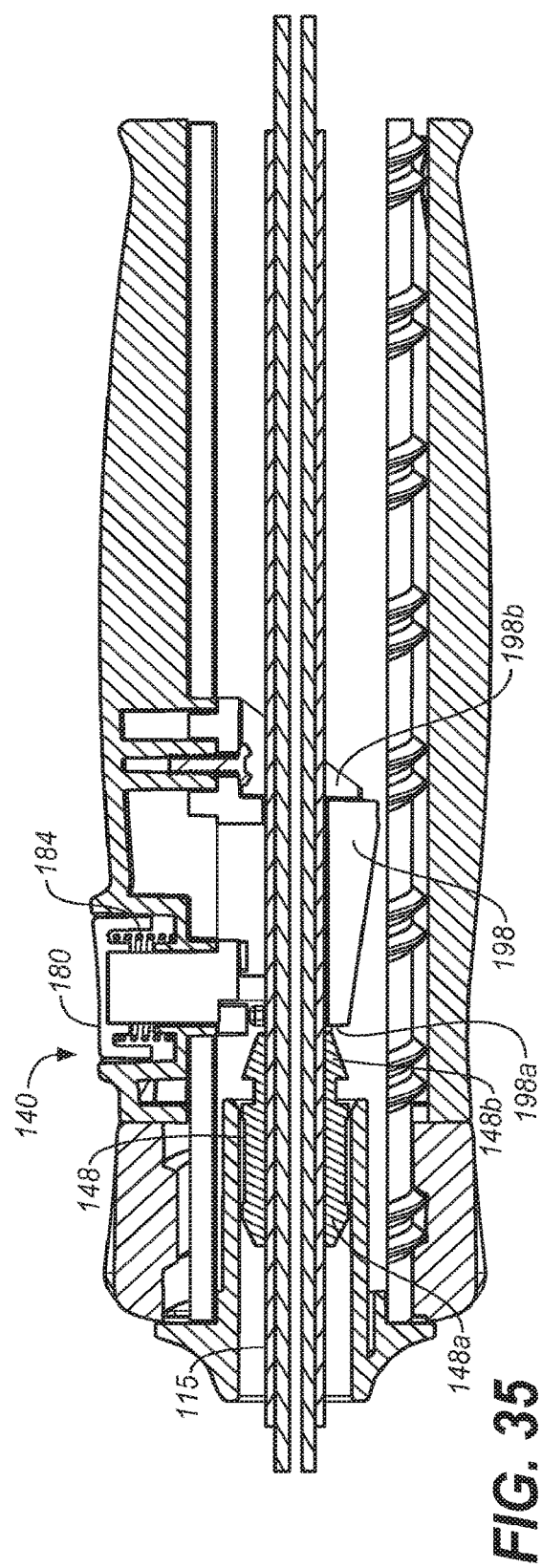

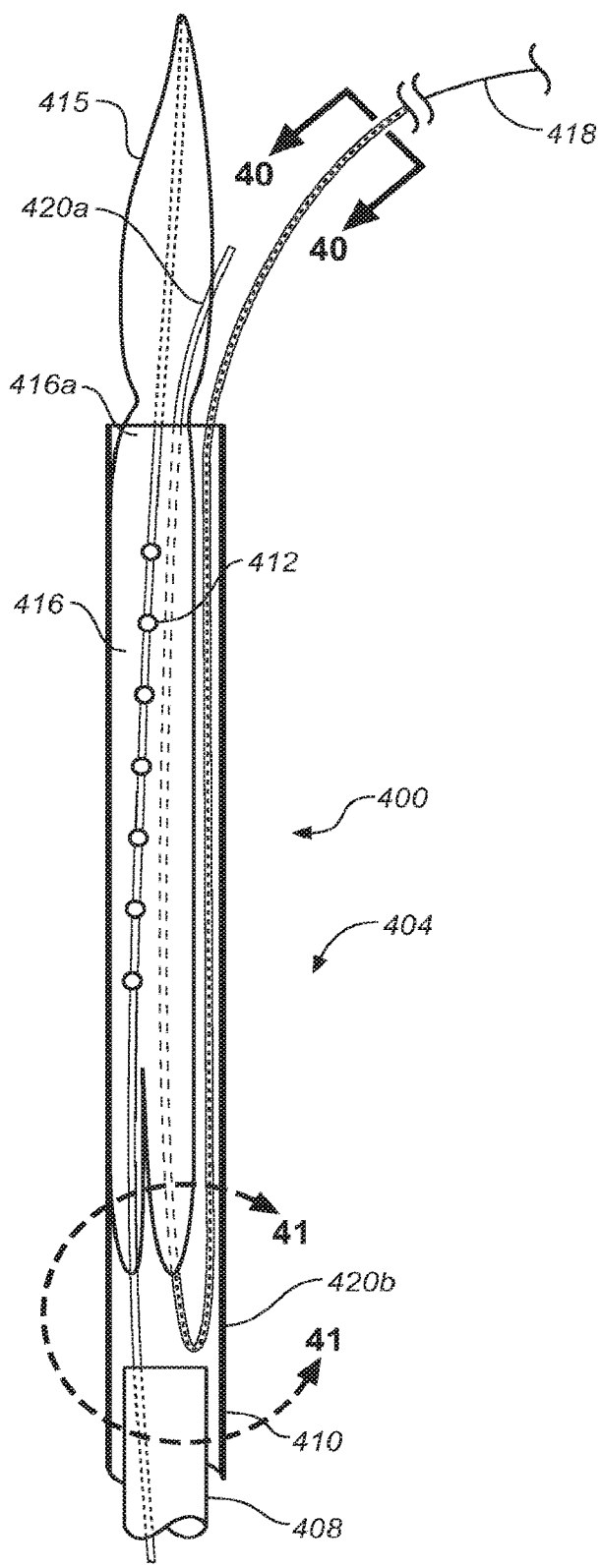
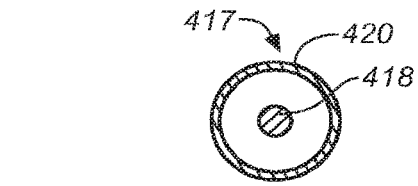
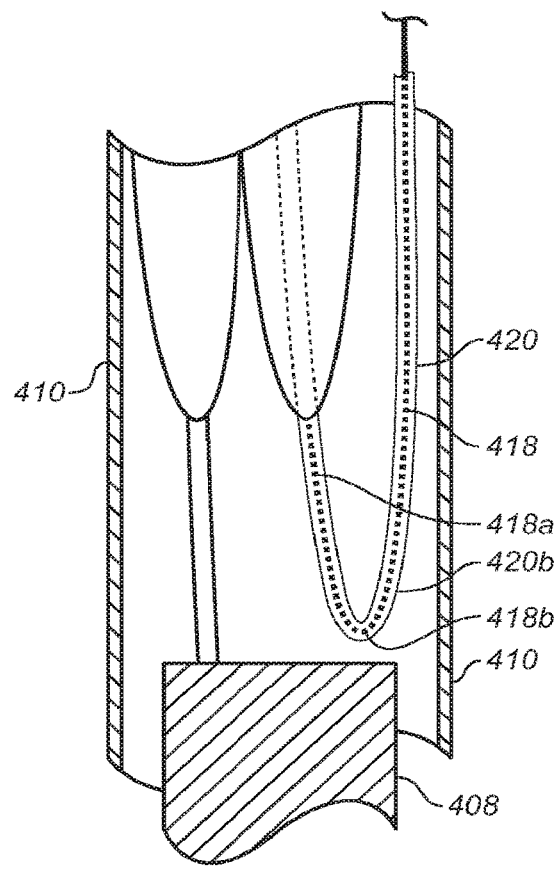
FIG. 39
FIG. 40
FIG. 41

CATHETER SYSTEM AND METHODS OF USING SAME

PRIORITY CLAIM

The present application is a continuation of U.S. patent application Ser. No. 15/379,268, filed Dec. 14, 2016, which is a continuation of U.S. patent application Ser. No. 14/462,485, filed Aug. 18, 2014, now U.S. Pat. No. 9,549,835, which is a divisional of U.S. patent application Ser. No. 13/408,952, filed Feb. 29, 2012, now U.S. Pat. No. 8,808,350, issued Aug. 19, 2014, which claims priority from U.S. Patent Application No. 61/448,154, filed Mar. 1, 2011, the content of both of which is incorporated by reference herein in its entirety. The benefit of priority is claimed under the appropriate legal basis including, without limitation, under 35 U.S.C. § 119(e).

INCORPORATION BY REFERENCE

U.S. application Ser. No. 11/623,022, filed Jan. 12, 2007, entitled "DUAL CONCENTRIC GUIDEWIRE AND METHODS OF BIFURCATED GRAFT DEPLOYMENT." U.S. application Ser. No. 12/101,863, filed Apr. 11, 2008, entitled "BIFURCATED GRAFT DEPLOYMENT SYSTEMS AND METHODS," U.S. application Ser. No. 12/496,446, filed Jul. 1, 2009, entitled "CATHETER SYSTEM AND METHODS OF USING SAME," U.S. application Ser. No. 12/769,506, filed Apr. 28, 2010, entitled "APPARATUS AND METHOD OF PLACEMENT OF A GRAFT OR GRAFT SYSTEM." and U.S. Pat. No. 6,077,296, entitled "ENDOLUMINAL VASCULAR PROSTHESIS," are hereby incorporated by reference as if fully set forth herein.

TECHNICAL FIELD

The present disclosure relates to catheter systems, in particular, catheter systems for delivering a medical prosthesis.

BACKGROUND

Introducer catheters or introducer sheaths can be used for minimal invasive placement of catheters into blood vessels. Introducer catheter sheaths typically comprise tubing that is inserted into the blood vessel and a seal or valve at the proximal end of the tubing which is positioned outside of the body. The seal can provide a hemostatic seal against blood loss. Stents or other medical prostheses are typically passed through the introducer sheath into the blood vessel or body passageway. The introducer sheath thus provides continuous access for the delivery of stents or other medical prostheses, protects the inner wall of the blood vessel or body passageway against damage when the stent or other prostheses is advanced through the body passageway, and provides a hemostasis seal against blood loss.

There are situations in which the catheters require substantial maneuvering within the blood vessel. For example, placement of a stent or stent graft may require the delivery catheter to be positioned precisely axially as well as rotationally at a specific location within the blood vessel. In addition deployment of the stent may require precise operation of the delivery system within the introducer. In these situations, the operator has to carefully control both the position of the introducer and the delivery system. A need exists for a delivery system that permits a user or medical practitioner to precisely control the axial position of the stent or prosthesis during deployment.

SUMMARY

Embodiments disclosed herein pertain to a catheter system for the insertion and positioning of diagnostic or therapeutic devices into blood vessels. The system comprises an introducer or an introducer sheath (also referred to herein as an outer sheath) and at least one delivery catheter. The introducer catheter can be introduced through a percutaneous puncture site into the blood stream. A docking mechanism can engage the proximal end of the introducer catheter assembly with a distal end portion of a delivery catheter and can prevent axial movement between the introducer catheter assembly and the delivery catheter assembly.

The catheter system can include an introducer catheter and a delivery catheter, where the introducer catheter includes an outer sheath and a seal that has an adjustable hemostasis valve connected to the proximal portion of the outer sheath. The introducer catheter and the delivery catheter can be configured such that the delivery catheter can removably engage with the introducer catheter such that, when the delivery catheter is engaged with the introducer catheter, the delivery catheter can be axially fixed to the introducer catheter so as to prevent substantial axial movement between the introducer catheter and the delivery catheter and to enable the catheters to be manipulated in an axial direction as a single unit.

Alternatively, the delivery catheter and introducer catheter can be configured such that, when the delivery catheter is engaged with the introducer catheter, an inner core of the delivery catheter can be rotated relative to the introducer catheter and the introducer sheath (also referred to herein as an outer sheath). Alternatively, the delivery catheter can be configured such that the inner core thereof can be locked or substantially prevented from rotational movement relative to the outer sheath of the introducer catheter and/or relative to the introducer catheter. Also disclosed is a method of placement of a stent or medical prosthesis into a blood vessel, wherein the stent or medical prosthesis is passed through an introducer sheath and the proximal end of the introducer catheter physically engages with or is removably docked with a distal end portion of the delivery catheter to prevent substantial axial motion between the introducer sheath and the delivery catheter.

Some endoprostheses, including stents, grafts, stent grafts, and dissection treatment devices, (all such endoprostheses are collectively referred to herein as a stent or stents) may require precise placement in both axial and rotational direction. For example, stents or stent grafts with fenestrations require accurate placement of those fenestrations relative to the branch vessels. The catheter systems disclosed herein can be configured to allow for the rotation of the delivery catheter and, hence, the stent, relative to the introducer sheath, in some embodiments, the friction that can otherwise impede the rotational freedom of the delivery catheter can be further reduced by lining the inner surface of the introducer sheath and/or the tubular sheath of the deployment catheter with a low-friction coating such as polytetrafluoroethylene, silicone, hydrophobic silicone, or other lubricating substance, or by applying a hydrophilic coating to the outer surface of the inner core or restraining sheaths of the delivery catheter. The lubrication can be swabbed onto the target surface.

Thus, the introducer sheath can remain rotationally static or fixed while the delivery catheter is rotated within the introducer sheath. This can protect the delivery catheter and stent from being damaged, torqued, or stressed during the rotational manipulation of the delivery catheter and stent, and also prevent any damage or stress on the vessel wall from the rotation of the delivery catheter or stent.

Additionally, the delivery catheter can be configured to permit a user or medical practitioner to selectively control or prevent, the rotational movement of the delivery catheter and stent relative to the introducer catheter, or the inner core of the delivery catheter and stent relative to the outer sheath of the delivery catheter. For example, the delivery catheter can comprise a threaded hub supported at the proximal end portion of the delivery catheter configured to selectively constrict or tighten against an outer wall of the inner core of the delivery catheter. By constricting the hub against the inner core, the inner core can be prevented or inhibited from rotating relative to the introducer catheter. By loosening the hub relative to the inner core, the rotational freedom of the inner core or delivery catheter relative to the introducer sheath can be restored.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 2A is a schematic representation of another catheter system comprising a docking arrangement to physically engage a catheter with an introducer sheath.

FIG. 2B is a schematic representation of the catheter system shown in FIG. 2A, showing the catheter engaged with the introducer sheath.

FIG. 2C is a schematic representation of the catheter system shown in FIG. 2A, showing a mechanism for disengaging the catheter from the introducer sheath.

FIG. 18 is a top view of the delivery catheter assembly of FIG. 16.

FIG. 19 is a side view of the delivery catheter assembly of FIG. 16.

FIG. 27 is a side view of the inner core engagement assembly and the inner core as in FIG. 26, showing the inner core in the second, partially engaged position relative to the inner core engagement assembly.

FIG. 28 is a top view of the inner core engagement assembly and the inner core as in FIG. 26, showing the inner core in the second, partially engaged position relative to the inner core engagement assembly.

FIG. 34 is a cross-sectional view of a portion of the delivery catheter through the axial centerline of the delivery catheter, showing the inner core in the disengaged position relative to the inner core engagement assembly.

FIG. 35 is a cross-sectional view of a portion of the delivery catheter through the axial centerline of the delivery catheter, showing the inner core in the engaged position relative to the inner core engagement assembly.

FIG. 39 is a schematic side view of a catheter system having a deployment catheter assembly showing a stent supported therein, and a branch vessel wire assembly loaded in the delivery catheter.

FIG. 40 is a cross-sectional view of the branch vessel wire assembly taken at line 40-40 of FIG. 39.

FIG. 41 is an enlarged schematic view of a portion 41-41 of the branch vessel wire assembly of FIG. 39.

DETAILED DESCRIPTION

The following detailed description is now directed to certain specific embodiments. In this description, reference is made to the figures wherein like parts are designated with like numerals throughout the description and the drawings. Described below are various embodiments of a catheter system that can comprise an introducer sheath and a docking arrangement. The catheter systems disclosed herein can be used in diagnostic or therapeutic procedures such as, but not limited to, endoluminal vascular prosthesis deployment procedures.

Figure 1A:
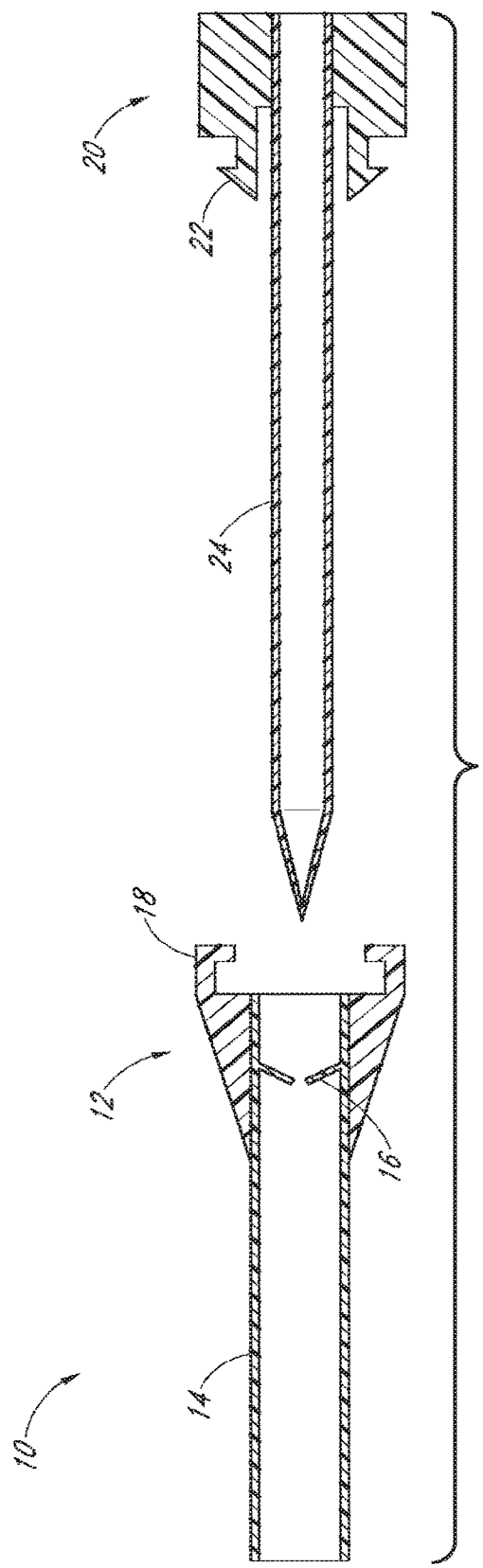
FIG. 1A is a schematic representation of a catheter system comprising a docking arrangement to physically engage a catheter with an introducer sheath.
Figure 1B:
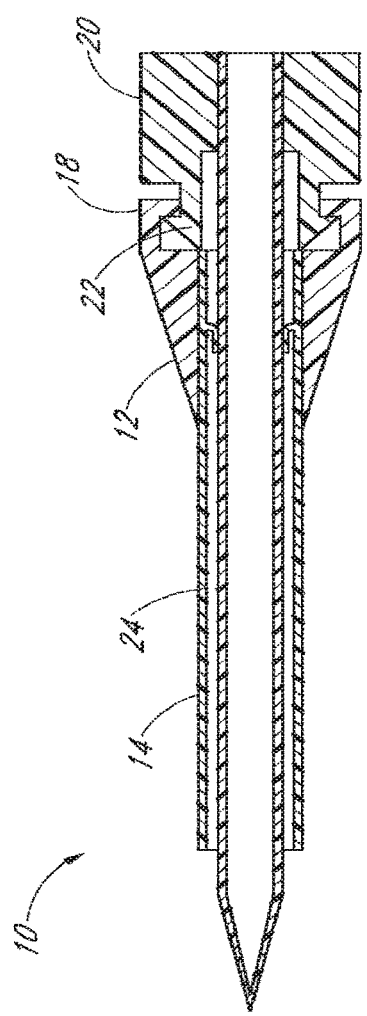
FIG. 1B is a schematic representation of the catheter system shown in FIG. 1A, showing the catheter engaged with the introducer sheath.

FIG. 1A is a schematic representation of a catheter system 10 comprising a docking arrangement configured to physically engage a catheter 20 with an introducer 12. FIG. 1B is a schematic representation of the catheter system. 10 shown in FIG. 1A, showing the catheter 20 engaged with the introducer 12. The catheter 20 or any catheter disclosed herein can be a diagnostic or therapeutic catheter, or any other suitable catheter. The introducer 12 can comprise a tubular sheath 14, a seal 16, and a female docking mechanism 18. The first seal 16 can be a rubber seal, an interference or close tolerance fit between adjacent components, an adjustable hemostasis valve, or any other suitable sealing component or feature.

The catheter 20 catheter has a shaft 24 and a male docking mechanism 22. As illustrated in FIG. 1B, the catheter 20 is inserted into the introducer 12 and the female docking mechanism 18 is engaged with the male docking mechanism 22. The docking mechanism prevents the introducer 12 and the catheter 20 from moving axially with respect to each other when the docking mechanism is engaged. Additionally, the catheter system 10 is configured so that the catheter 20 can rotate within the introducer 12, even when the catheter 20 is docked with the introducer 12.

The introducer 12 comprises a tubular introducer sheath 14 and a seal 16 (which, again, can be a rubber seal, an interference or close tolerance fit, an adjustable hemostasis valve, or any other suitable scaling component or feature) connected to the proximal end of the introducer sheath 14. The overall design of the sheath 14 and seal 16 may be similar to the design of commercially available introducers, or any other introducers presently known or later developed. The catheter 20 has an outside dimensional profile (crossing profile) that is sized and/or configured to pass through the introducer sheath 14. The proximal end of the catheter 20 and the proximal end of the introducer sheath 14 are configured to permanently or removably engage with each other, and to allow for the rotation of the catheter 20 within the introducer sheath 14 while substantially limiting the axial movement of the catheter 20 with respect to the introducer sheath 14.

With respect to the sizing of the introducer lumen versus the size of the outer sheath (containing the stent graft), in one configuration they are the same size and the introducer acts as a sheath, as the stent graft is pushed from its initial position within the outer sheath through to the lumen of the introducer. In a second configuration, the introducer lumen is larger than the outside diameter of the outer sheath and the two easily rotate relative to one another as needed for rotational alignment. Further, the introducer material can be softer or more flexible material than the outer sheath, so while the stent graft could be initially loaded into a strong high-strength sheath material, it could be extruded through to the lower strength more highly flexible introducer material for the short time needed to deliver the stent grafts to its treatment site, the materials that might be used to provide this feature, include any kind of soft polymer extrusion including Nylon, PEBAX, and PE.

After engagement of the catheter and introducer, the combined system is operable by a single operator. The catheter system 10 is configured so that the catheter 20 can substantially freely rotate within the introducer sheath 14, which can allow for precise rotational positioning of the catheter within the introducer. After completion of the procedure, the catheter 20 is disengaged from the introducer 12 so that the catheter 20 can be removed from the patient's body. Additionally, the introducer 12 can be repositioned for a second intervention and a second catheter can be inserted and engaged with the introducer 12 for additional procedures.

FIG. 2A is a schematic representation of a catheter system 40 comprising a docking arrangement to physically engage a catheter 50 with an introducer 42. FIG. 2B is a schematic representation of the catheter system 40, showing the catheter 50 engaged with the introducer 42. FIG. 2C is a schematic representation of the catheter system 40 shown in FIG. 2A, showing a mechanism for disengaging the catheter 50 from the introducer 42.

In particular. FIG. 2C schematically illustrate that the catheter 50 can be disengaged from the male docking mechanism 52 and the introducer 42 by compressing the levers or tabs 56. Accordingly, as illustrated the male docking mechanism 52 can be elongated and can comprise levers 56.

Figure 3A:
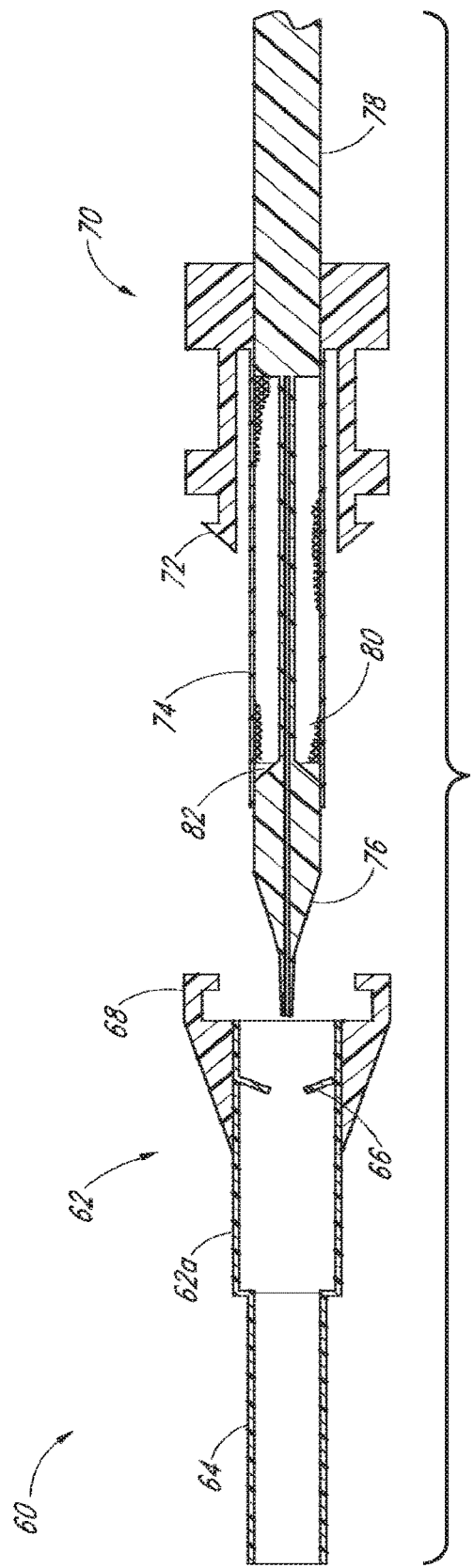
FIG. 3A is a schematic representation of another catheter system comprising a docking arrangement to physically engage a catheter with an introducer sheath, the catheter system being configured to deliver a stent or stent graft into a blood vessel.
Figure 3B:
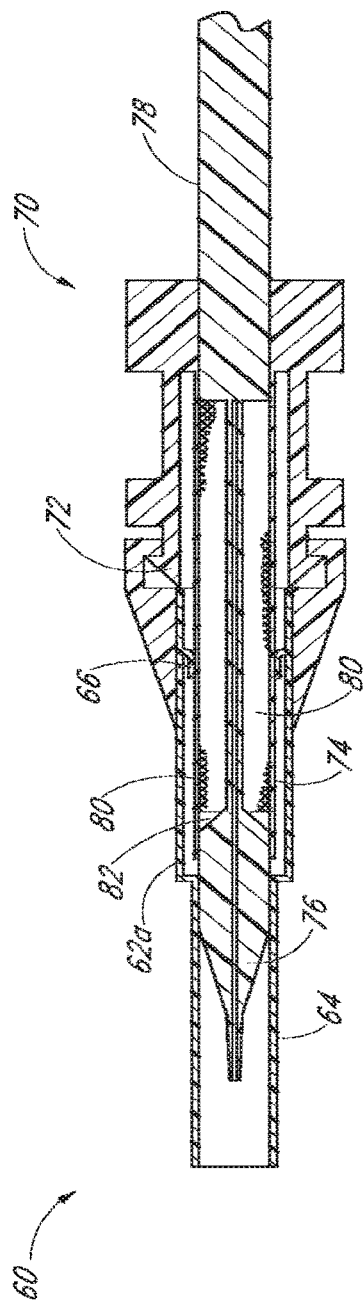
FIG. 3B is a schematic representation of the catheter system shown in FIG. 3A, showing the catheter engaged with the introducer sheath.
Figure 3C:
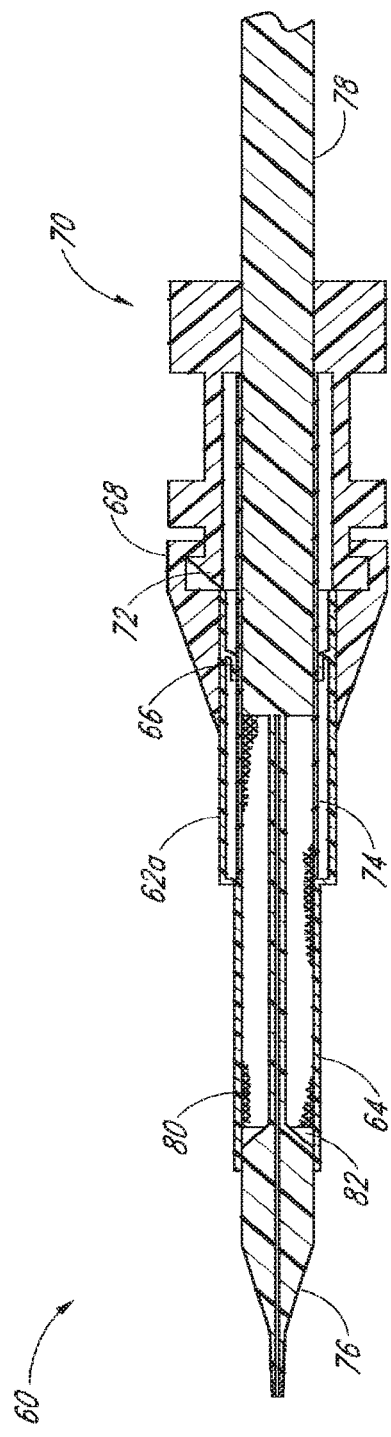
FIG. 3C is a schematic representation of the catheter system shown in FIG. 3A, illustrating the axial insertion of a stent into the tubular sheath of the introducer sheath shown in FIG. 3A.
Figure 3D:
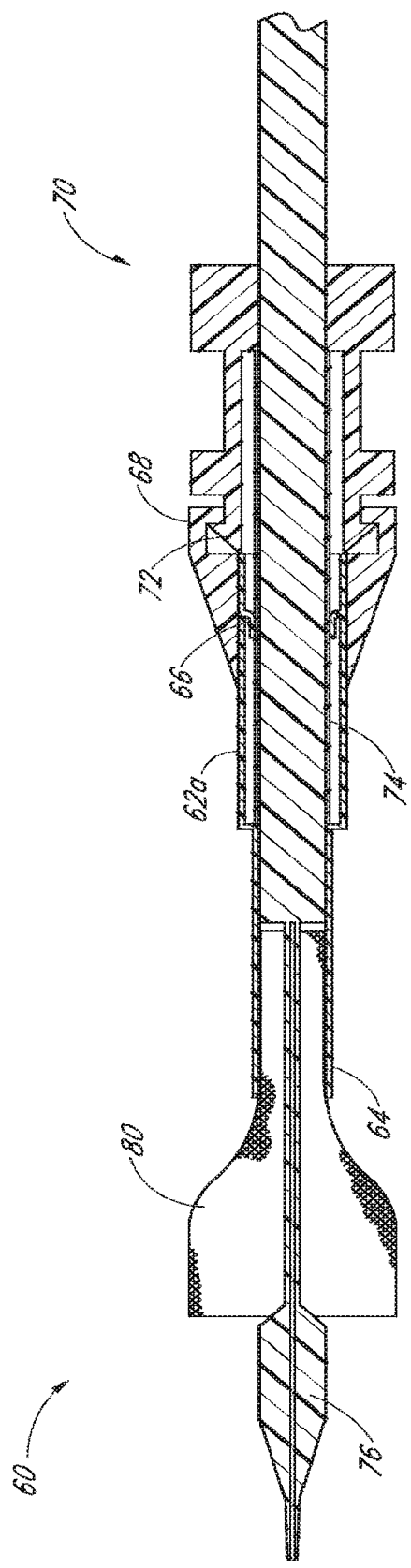
FIG. 3D is a schematic representation of the catheter system shown in FIG. 3A, illustrating the stent being deployed after the tubular sheath of the introducer sheath shown in FIG. 3A has been retracted from the stent.

FIG. 3A is a schematic representation of a catheter system 60 comprising a docking arrangement to physically engage a catheter 70 with an introducer 62, the catheter system 60 being configured to deliver a stent or stent graft 80 into a blood vessel. FIG. 3B is a schematic representation of the catheter system 60 shown in FIG. 3A, showing the catheter 70 engaged with the introducer 62. FIG. 3C is a schematic representation of the catheter system 60 shown in FIG. 3A, illustrating the axial insertion of a stent or stent graft 80 into the tubular sheath 64 of the introducer 62 shown in FIG. 3A. FIG. 3D is a schematic representation of the catheter system 60 shown in FIG. 3A, illustrating the stent 80 being deployed after the tubular sheath 64 of the introducer 62 shown in FIG. 3A has been retracted from the stent 80.

Self-expanding stent or stents grafts are typically retained in a deployment sheath within the delivery catheter. The deployment sheath can protect the stent or stent graft and the vessel wall from damage during insertion and can retain the stent or stent graft in a collapsed low-profile configuration during delivery. The stent or stent graft can be deployed in the desired position of the blood vessel by removing the deployment sheath and allowing the stent or stent graft to radially expand against the wall of the blood vessel. To pass such a delivery catheter into the desired blood vessel, the catheter system can be configured so that the inner diameter of the introducer sheath is larger than the outer diameter of the deployment sheath. Clinicians prefer a low profile of the introducer sheath to minimize damage to the blood vessel and allowing for access into small blood vessels.

Cartridge systems have been developed, in which the stent or stent graft can be transferred from delivery sheath into the introducer sheath and the stent or stent graft can be passed through the introducer sheath to the target location. In such cartridge systems, the introducer sheath effectively acts as a deployment sheath. The transfer eliminates the need for a second sheath and minimizes the profile of the system in the blood vessel. The docking arrangement provides a secure engagement of the delivery catheter and the introducer sheath prior to transfer of the stent or stent graft into the introducer sheath. This prevents potential user errors in the transfer and further converts the delivery catheter and introducer sheath into a single-user system.

As illustrated in FIGS. 3A-3D, the catheter system 60 is used to transfer and deploy a stent or stent graft 80 into a blood vessel (blood vessel not shown). As illustrated therein, the introducer 62 comprises a tubular sheath 64 that is inserted into the body of the patient. The proximal end 62a of the introducer 62 can be sized and/or configured to accommodate the deployment sheath 74 of the catheter 70. The introducer sheath can also have a seal 66 (referred to herein as a first seal) and a female docking mechanism 68, similar to any of the embodiments of the seal, hemostasis valve, and/or docking mechanisms described above. The seal 66 can be an annular rubber seal (as illustrated), an interference or close tolerance fit between adjacent components, an adjustable hemostasis valve, or any other suitable sealing component or feature. The stent delivery catheter 70 can comprise an inner core 78, a pocket 82 that can house the collapsed stent 80, a deployment sheath 74 that can retain the collapsed stent 80, and a catheter tip 76.

As illustrated in FIG. 3B, the catheter 70 can be inserted into the introducer 62 when the docking mechanisms 68 and 72 are engaged. In some embodiments (not illustrated), the deployment sheath 74 of the delivery catheter 70 can be sized and con-figured to be received within the larger diameter proximal end 62a of the introducer sheath and to extend into the distal tubular sheath 64 of the introducer 62. Alternatively, the deployment sheath 74 of the delivery catheter 70 can be sized and configured to be received within the larger diameter proximal end 62a of the introducer sheath but not the distal tubular sheath 64 of the introducer 62. In some embodiments, as illustrated in FIGS. 3C and 3D, the deployment sheath 74 and the tubular sheath 64 can be sized and configured such that, when the deployment sheath 74 has advanced through the proximal end 62a of the introducer sheath, the similar size or shape of the distal tubular sheath 64 can prevent the deployment sheath 74 from advancing through the distal tubular sheath 64. The inner and/or outer diameters of the deployment sheath 74 and the tubular sheath 64 can be substantially the same.

As illustrated in FIG. 3C. The inner core 78 of the catheter 70 can be pushed distally, thereby transferring the stent 80 from the deployment sheath 74 into the tubular sheath 64 of the introducer 62. The stent 80 can be advanced until the catheter tip 76 reaches the distal end of the tubular sheath 64. In this configuration, the catheter/introducer system effectively becomes a single-unit deployment catheter. Thus, the tubular sheath 64 can function as a deployment sheath. The stent 80 can be advanced in a collapsed configuration within the protective introducer 62 to the target location in the blood vessel without increasing the profile of the delivery system. If the delivery catheter were passed through a traditional introducer sheath, the sheath of the introducer would have to be of a larger diameter than the deployment sheath of the delivery catheter to accommodate the stent and the deployment sheath. 2) other advantages which were mentioned:

in the configuration described the device can be rotated after it has been introduced to the introducer, but before it is deployed, further the device can be accurately position as a result of the low friction between the introducer and the outer sheath. When devices having an expanded diameter of 25 and 28 mm diameter devices are to be used, the same (one size) introducer sheath can be used for either and both devices delivery. Only when a larger 34 mm diameter device, having a larger compressed crossing profile, is to be delivered, is it necessary to use a larger introducer. The fact that the introducer and delivery catheter mechanically engage and create a single unitary structure which can be held by one hand, allows a single user to manipulate the whole system with two hands) one hand holding the core stationary and the second hand manipulating the sheath retraction mechanism.

As is known in the art, delivery catheters with loaded stent grafts typically have less trackability and pushability than an introducer sheath supported by a dilator. This is due to the fact that the stent grafts alter the local stiffness of the catheters. This can lead to kinking of the delivery catheter during insertion. By placing the introducer sheath with a dilator first, a conduit for placing the stent graft is established. Kinking of the delivery system pacing through the sheath is very unlikely.

Figure 4:
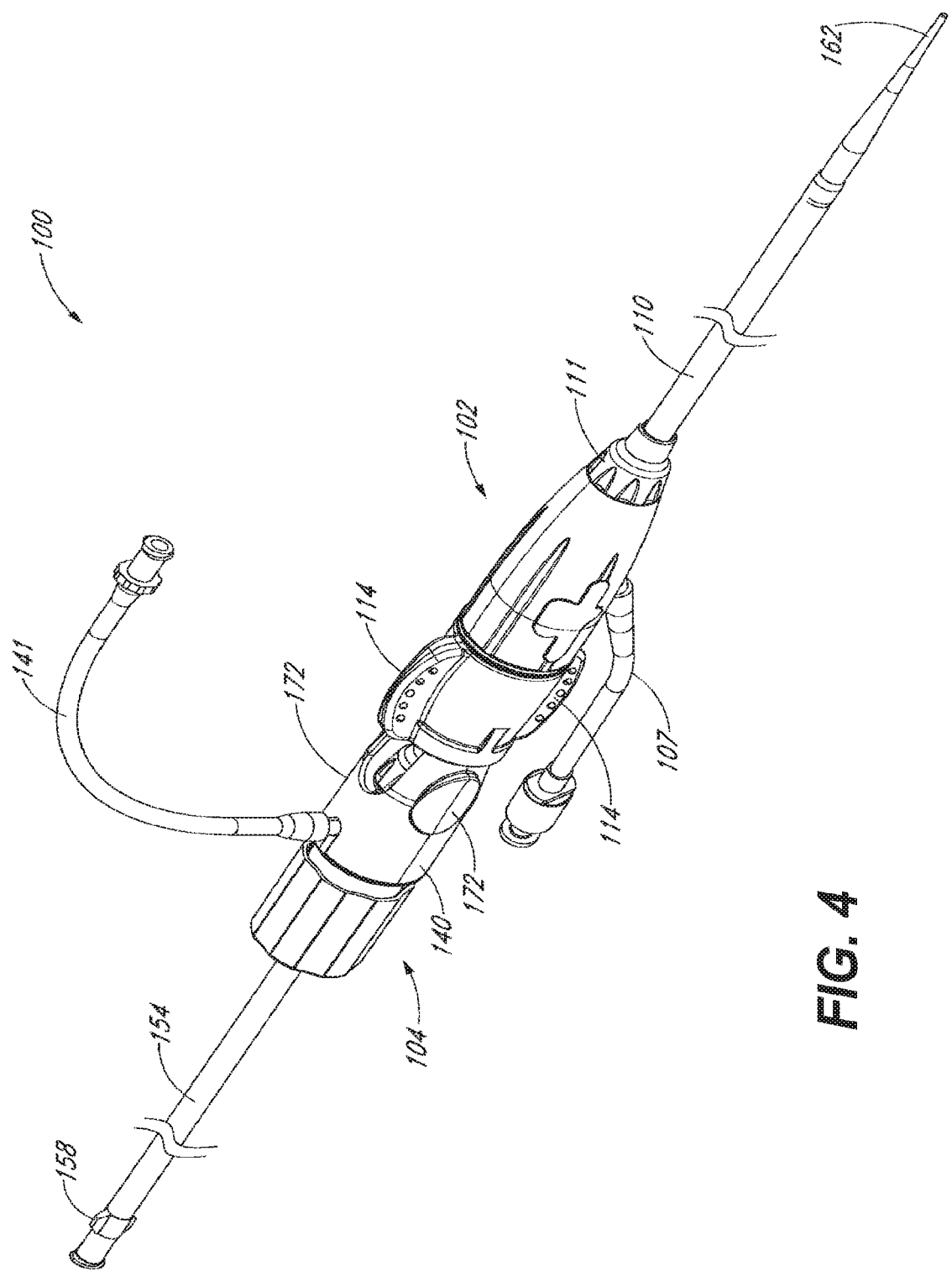
FIG. 4 is an oblique view of a catheter system comprising an introducer and a delivery catheter.

FIG. 4 is an oblique view of another catheter system 100 comprising an introducer catheter 102 (also referred to as an introducer) and a delivery catheter 104. The delivery catheter 104 can be configured for the delivery of an endoluminal prosthesis, or for any other suitable use. Therefore, the embodiments of the catheters and introducers disclosed herein can be configured for any suitable purpose, and the embodiments of the introducers disclosed herein can be configured to receive any suitable catheter design.

Figure 5:
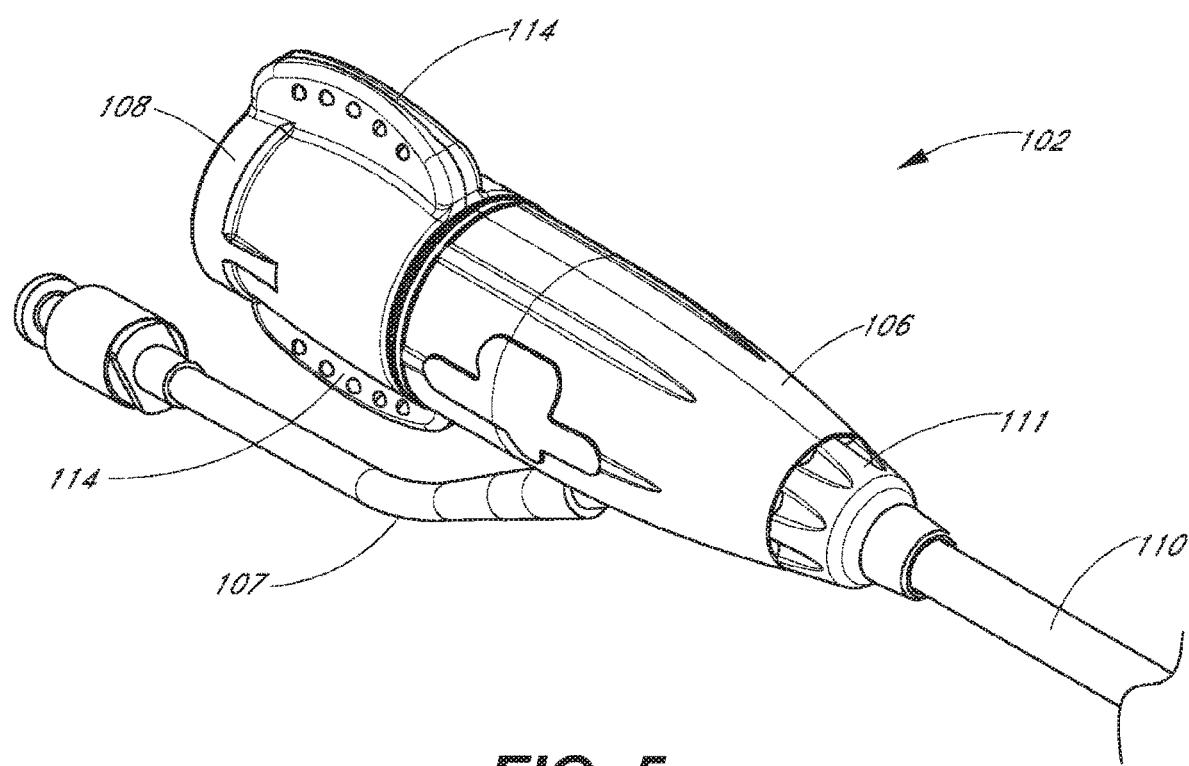
FIG. 5 is an oblique view of the introducer shown in FIG. 4.
Figure 6A:
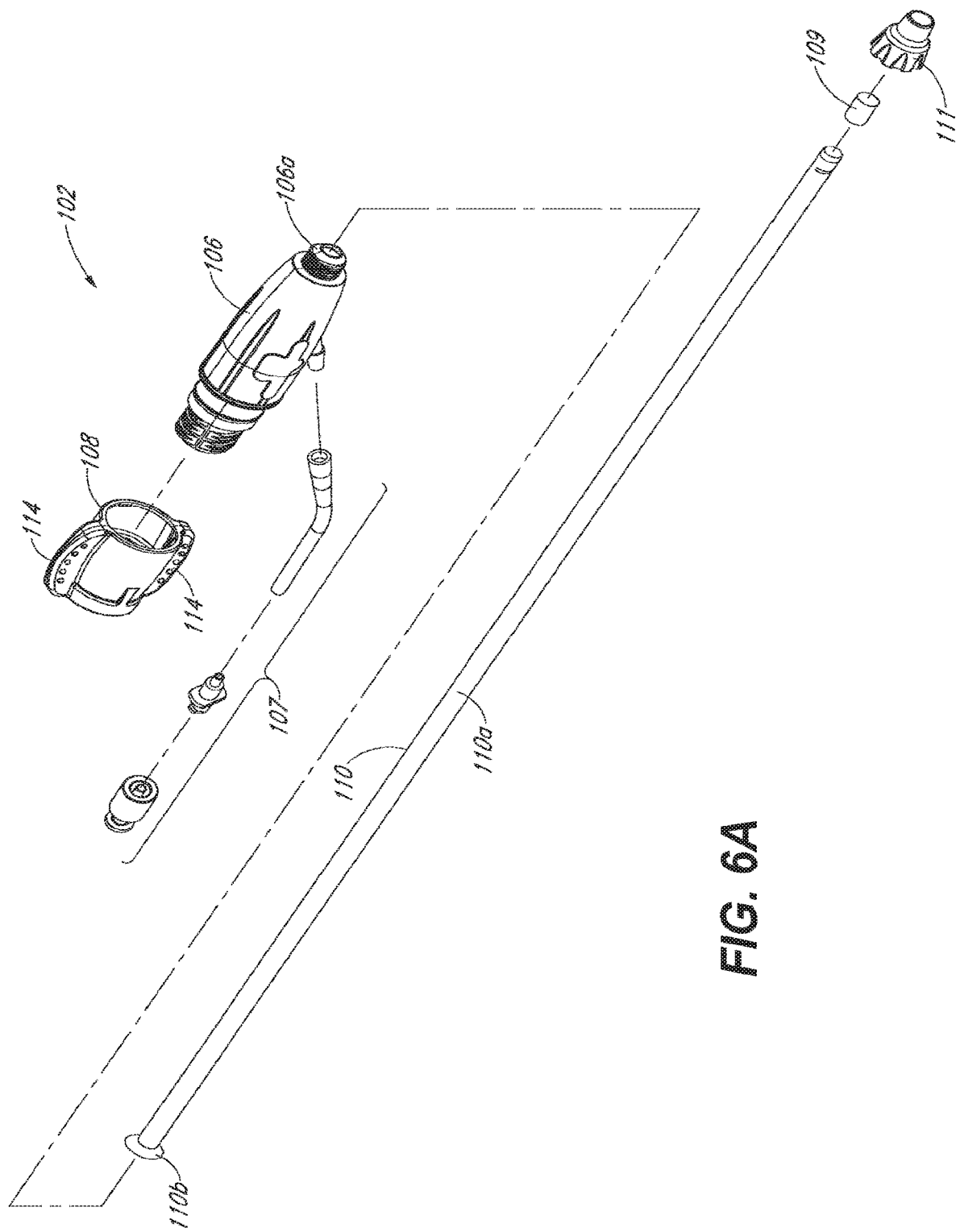
FIG. 6A is a first exploded assembly view of the introducer shown in FIG. 5.
Figure 6B:
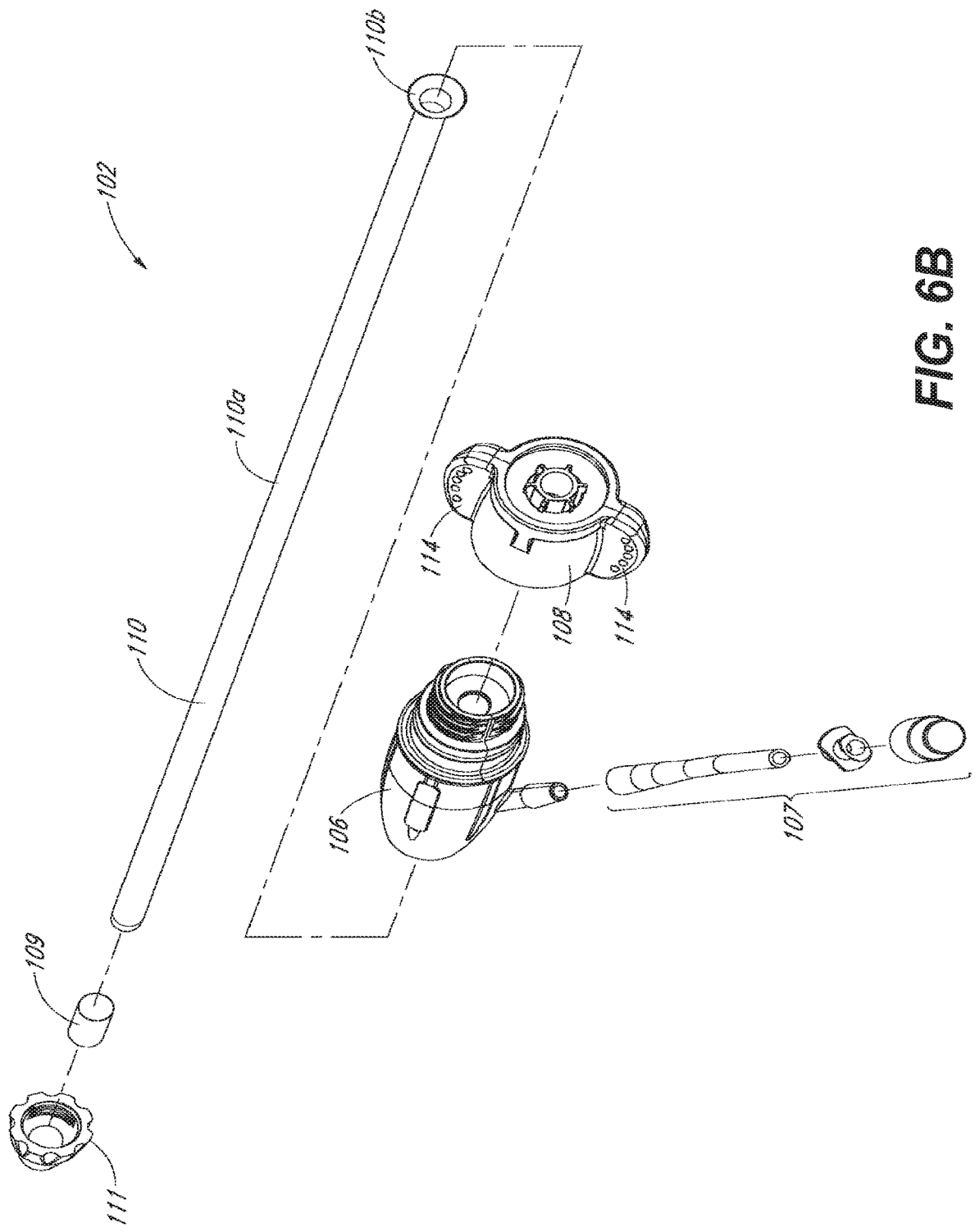
FIG. 6B is a second exploded assembly view of the introducer shown in FIG. 5.

FIG. 5 is an oblique view of the introducer 102 of the catheter system 100 shown in FIG. 4. FIGS. 6A and 6B are a first and a second exploded assembly view of the introducer 102 shown in FIG. 5. With reference to FIGS. 4-6, the introducer 102 can have a main body 106, a threadably engageable hub portion 108, an introducer sheath 110, and a threaded cap 111 configured to threadably engage with a threaded end portion of the main body 106.

In some embodiments, a first tube 107 can be supported by the main body 106 so as to provide an orifice or access port into the main body 106. The first tube 107 can be used to flush the introducer 102 with saline or other suitable substances at any stage, such as but not limited to prior to the advancement of an endoluminal prosthesis through the introducer 102, or prior to other procedures for which an introducer may be used. The first tube 107 can support any suitable medical connector and/or valve on the distal end thereof.

The introducer sheath 110 can have an elongate portion 110a extending to any predetermined or desired length. As will be discussed in greater detail below, similar to the introducer 12 of the catheter system 10 described above, the introducer sheath 110 can be configured such that an endoluminal prosthesis that is advanced into the introducer sheath 110 can be constrained or restrained by the introducer sheath 110. In this arrangement, the inside and/or outside diameter of the introducer sheath 110 can be approximately the same as or similar to the inside and/or outside diameter of the outer sheath of a delivery catheter that is engaged with the introducer 102. The elongate portion 110a can be circular in cross-section (as illustrated), or can define any suitable cross-sectional shape such as without limitation triangular, square, hexagonal, octagonal, or polygonal.

Further, as shown most clearly in FIG. 6A, the introducer sheath 110 can have a flared end portion 110b that can be configured to abut against a fore surface 106a of the main body 106. With reference to FIG. 6A, the elongate portion 110a of the introducer sheath 110 can pass through an opening formed in the cap 111 so that the flared portion 110b of the introducer sheath 110 can be engaged with and/or overlap an inside surface of the cap 111. In this configuration, the cap 11 supporting the introducer sheath 110 can be threadedly engaged with the main body 106 so that the introducer sheath 110 can be supported by the main body 106.

Additionally, with reference to FIGS. 6A and 6B, a tubular support or spacer 109 can be inserted over the elongate portion 110a of the introducer sheath 110 and positioned approximately adjacent to the flared portion 110b. The tubular spacer 109 can improve the fit and, hence, the seal between the outside surface of the introducer sheath 110 and the cap 111. The tubular spacer 109 can also provide additional support to the introducer sheath 110.

Figure 7:
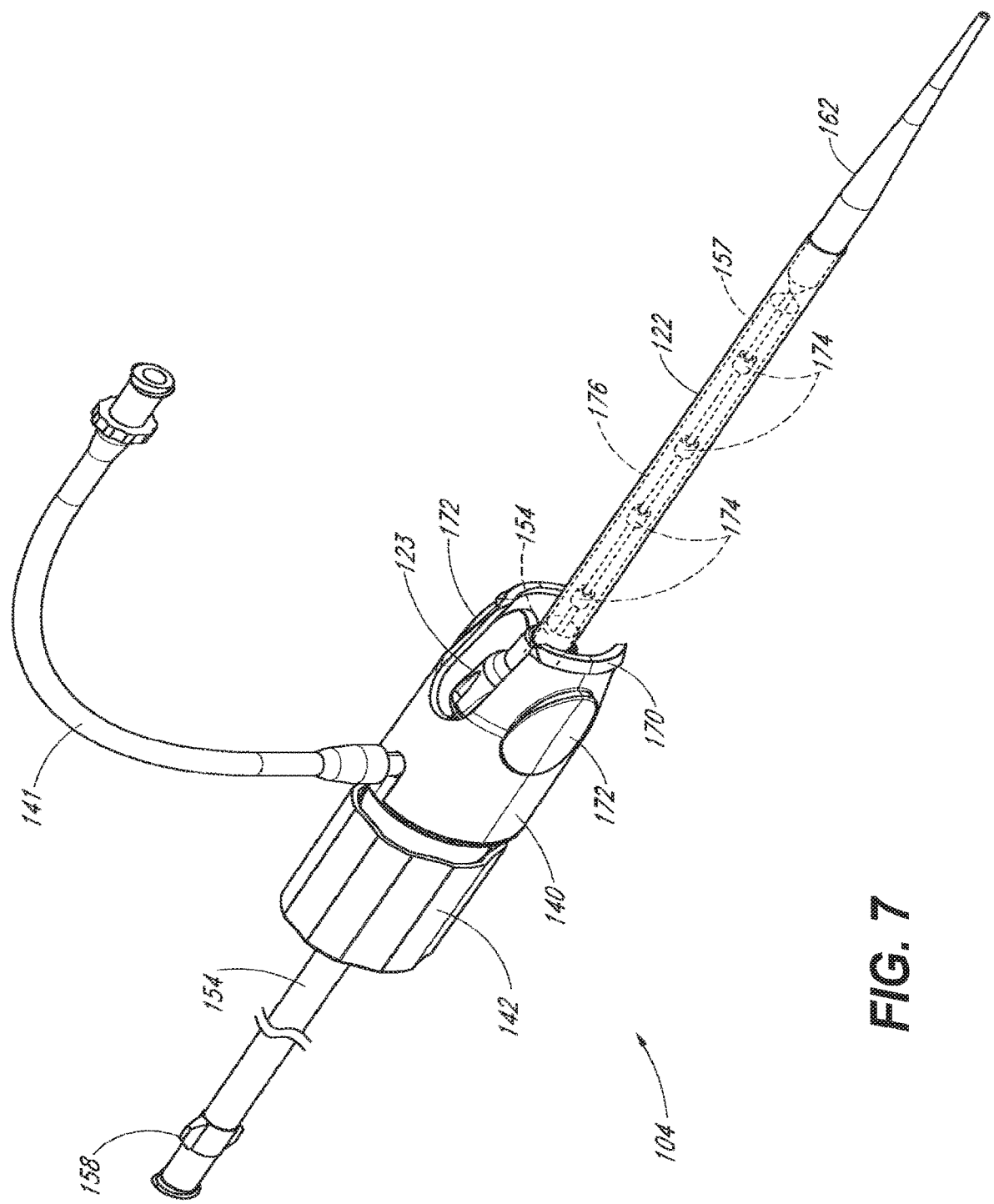
FIG. 7 is an oblique view of the delivery catheter shown in FIG. 4.

FIG. 7 is an oblique view of the delivery catheter 104 of the embodiment of the catheter system 100 shown in FIG. 4.

Figure 8A:
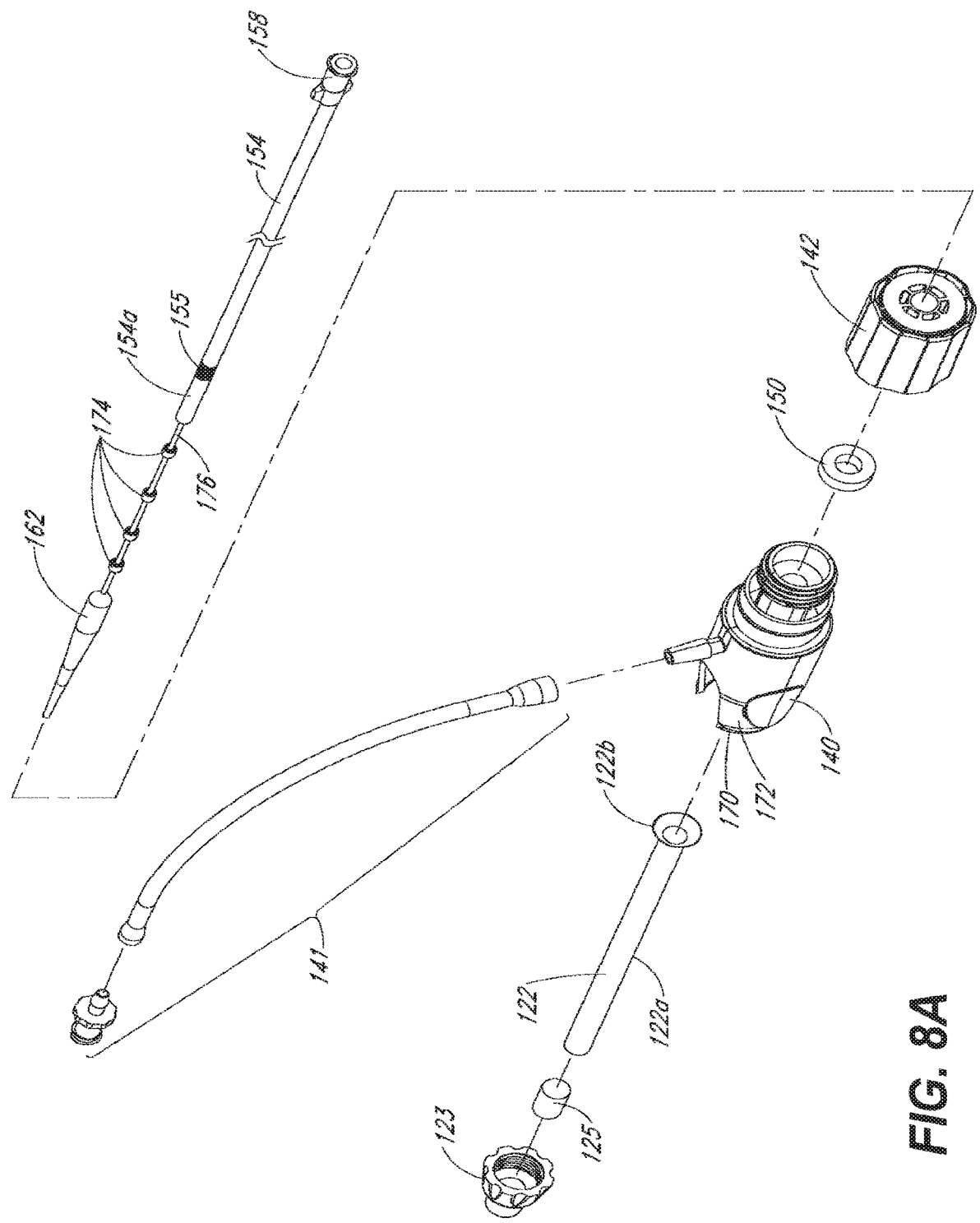
FIG. 8A is a first exploded assembly view of the delivery catheter shown in FIG. 7.
Figure 8B:
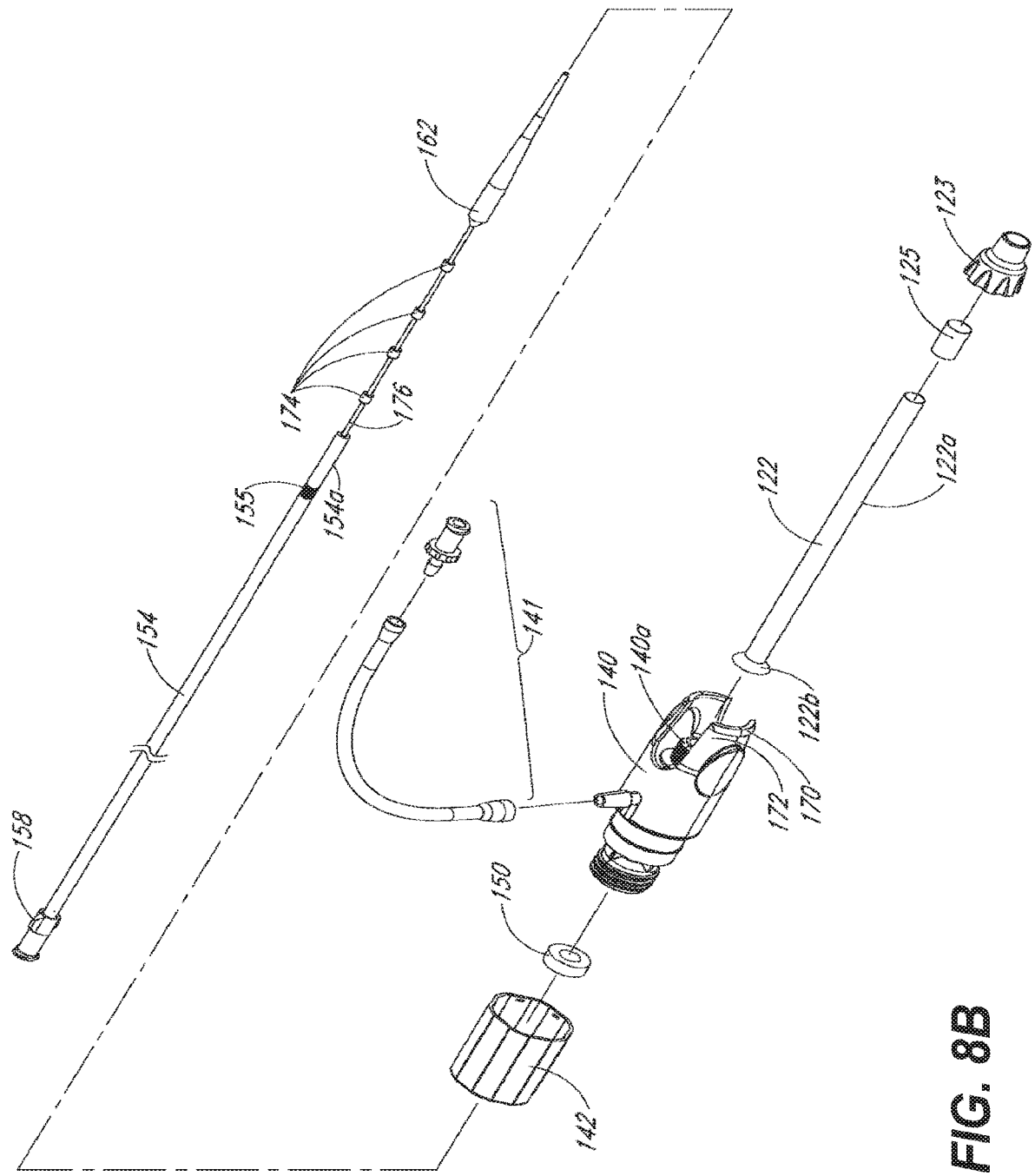
FIG. 8B is a second exploded assembly view of the delivery catheter shown in FIG. 7.

FIGS. 8A and 8B are a first and second exploded assembly view of the delivery catheter 104 shown in FIG. 7.

Figure 9:
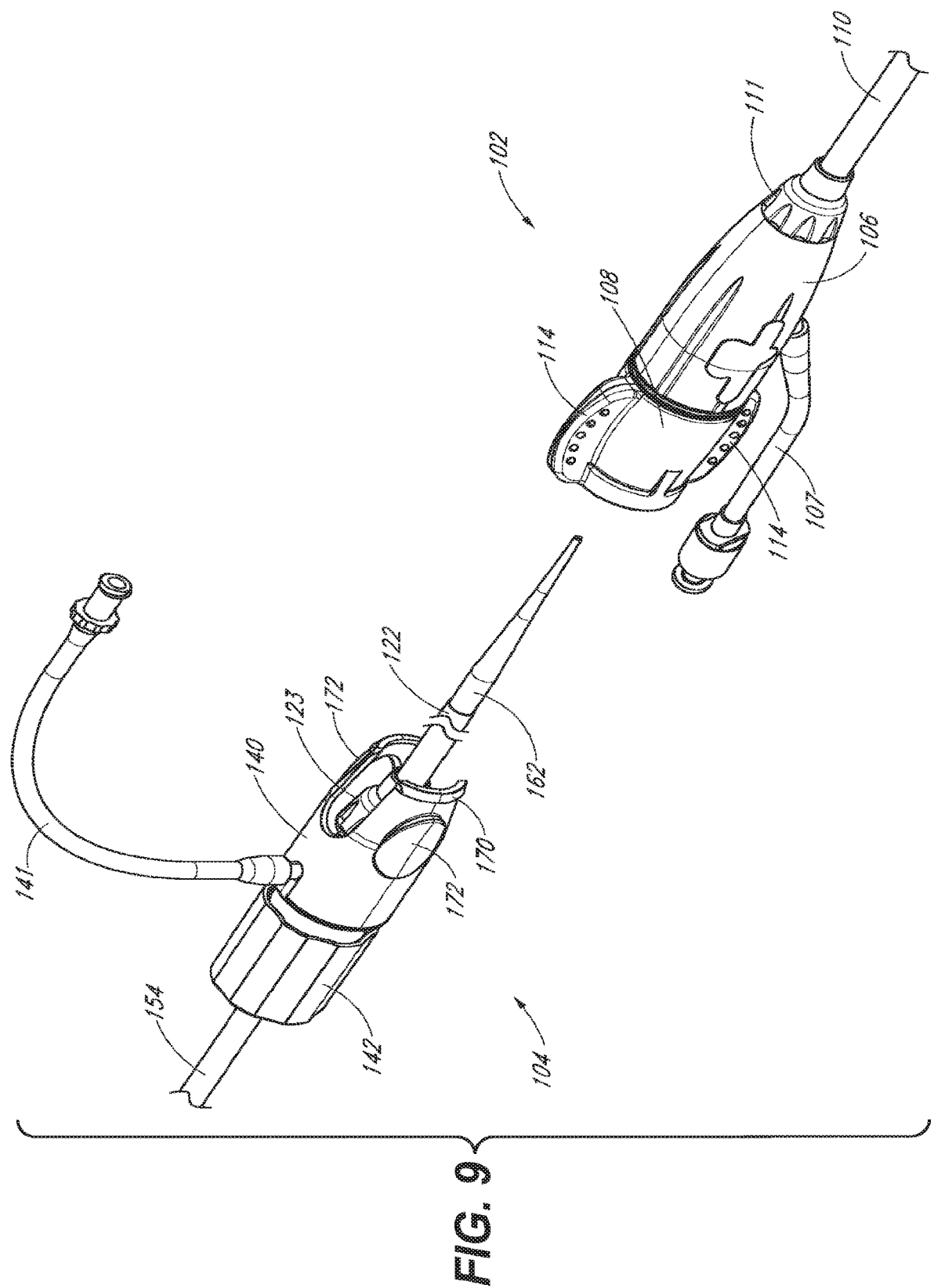
FIG. 9 is an oblique view of the catheter system shown in FIG. 4, showing the delivery catheter before the docking mechanism of the delivery catheter has been engaged with the docking mechanism of the introducer.

FIG. 9 is an oblique view of the catheter system 100 shown in FIG. 4, showing the delivery catheter 104 before the docking mechanism of the delivery catheter 104 has been engaged with the docking mechanism of introducer 102.

Figure 10:
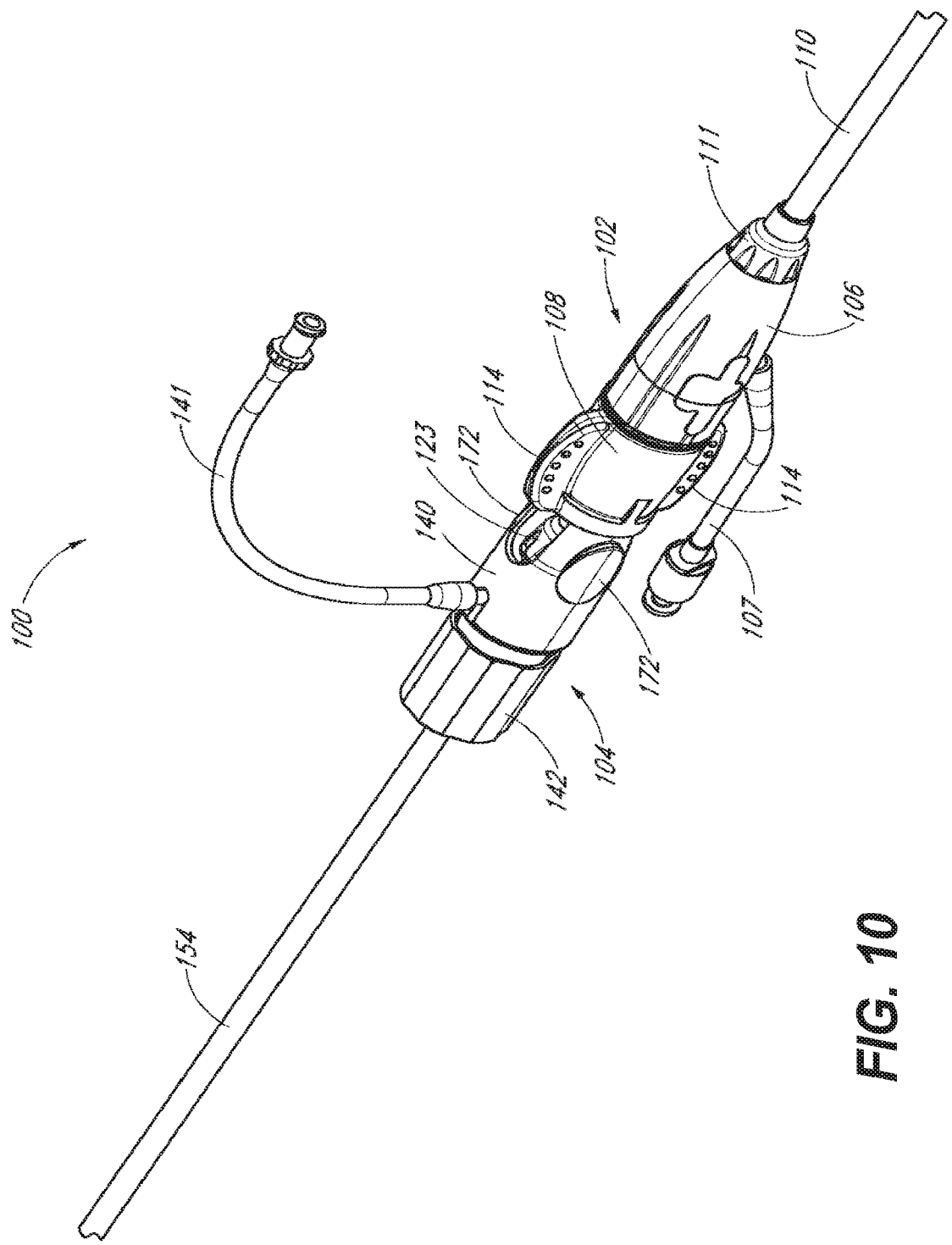
FIG. 10 is an oblique view of the catheter system shown in FIG. 4, showing the delivery catheter after the docking mechanism of the delivery catheter has been engaged with the docking mechanism of the introducer.

FIG. 10 is an oblique view of the catheter system 100 shown in FIG. 4, showing the delivery catheter 104 after the docking mechanism of the delivery catheter 104 has been engaged with the docking mechanism of the introducer 102.

Figure 11:
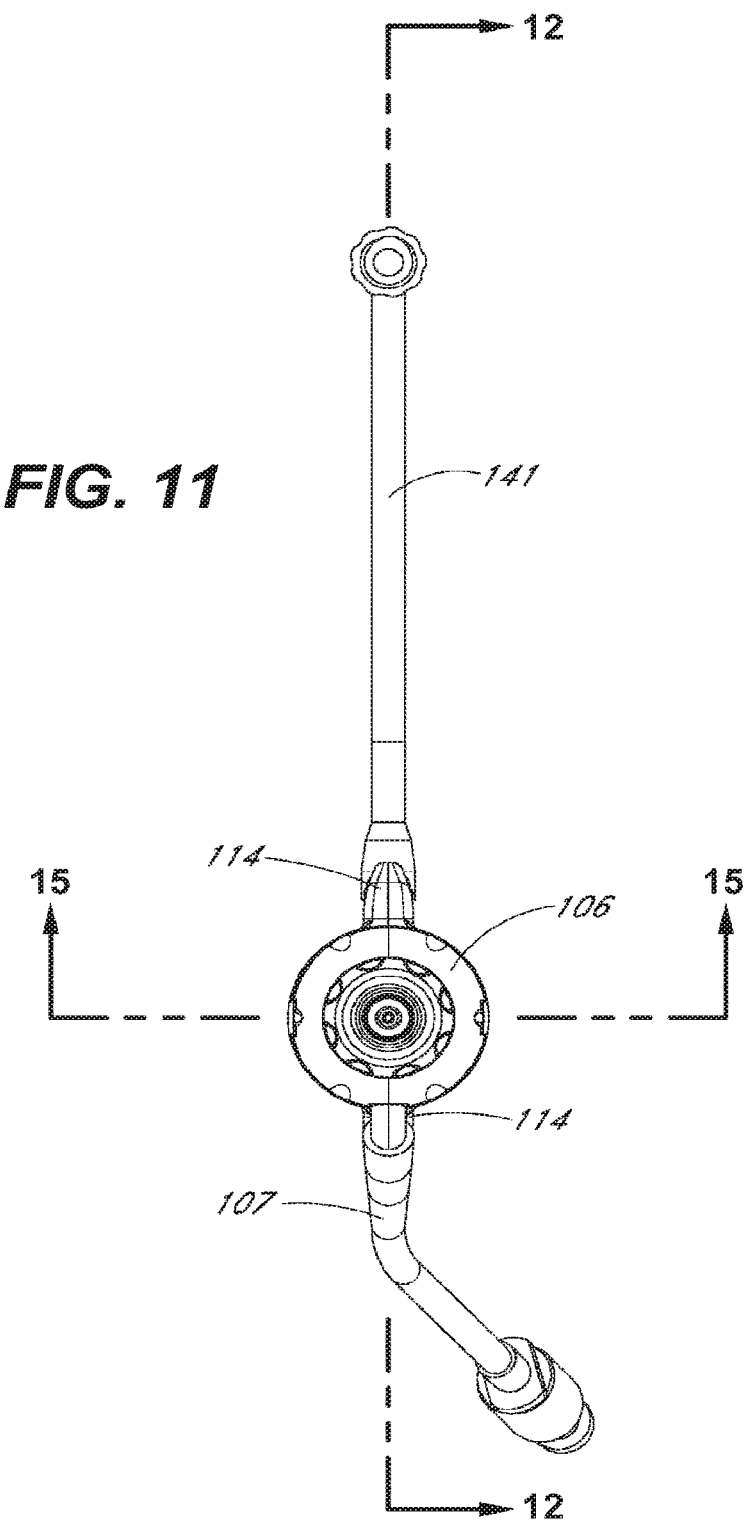
FIG. 11 is an end view of the catheter system shown in FIG. 4.
Figure 12:
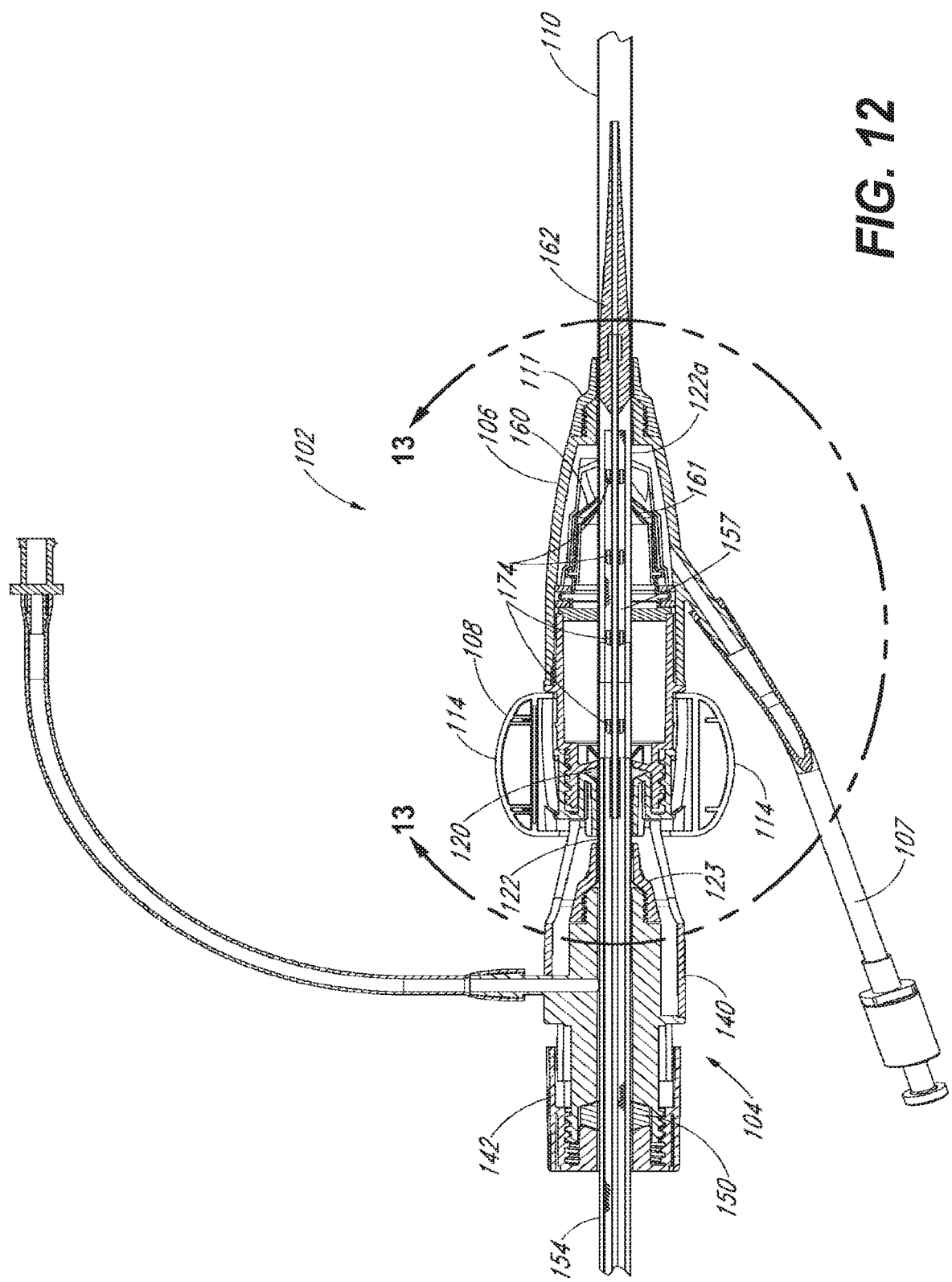
FIG. 12 is a cross-sectional view of the catheter system shown in FIG. 4, taken at line 12-12 of FIG. 11.
Figure 13:
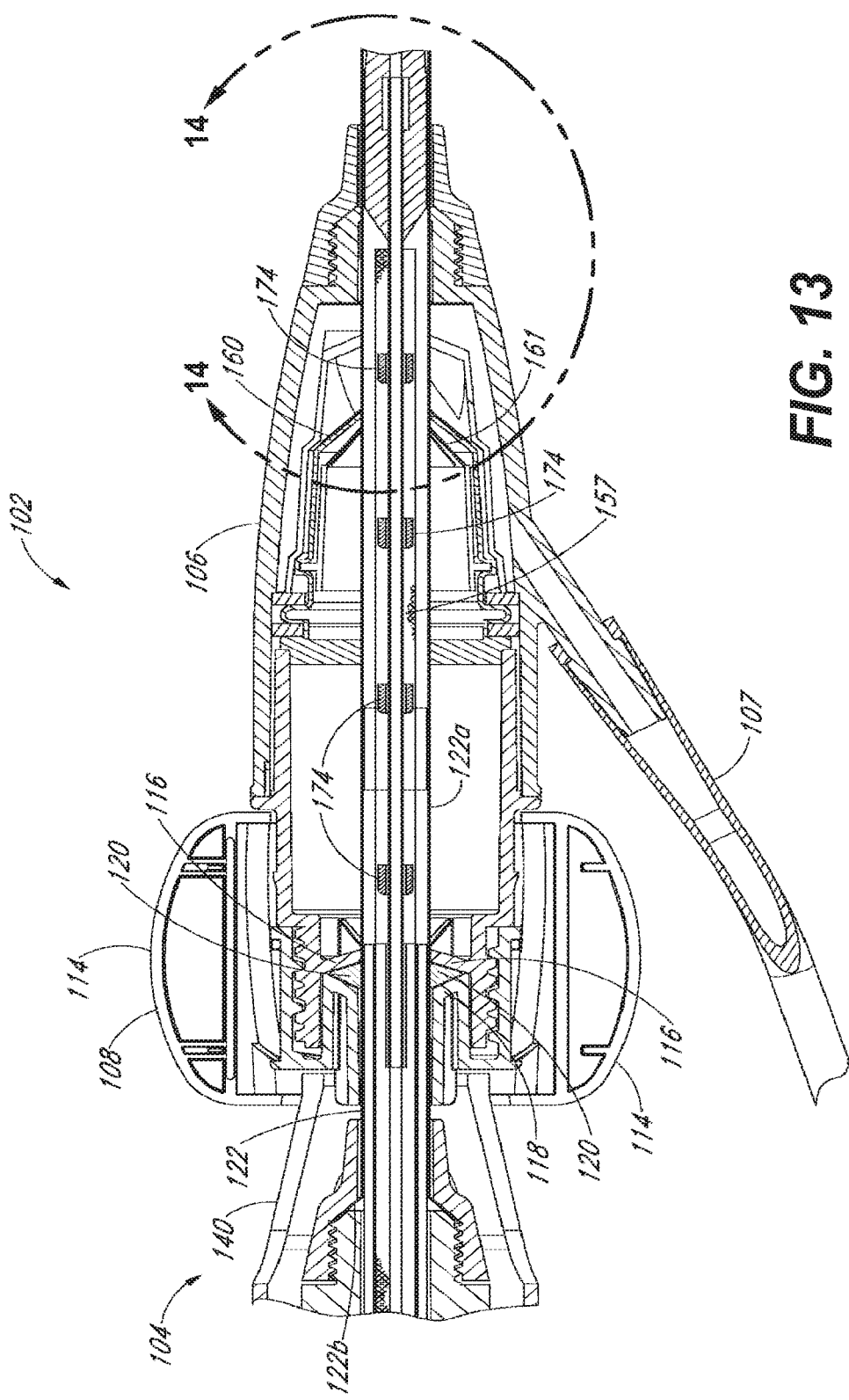
FIG. 13 is an enlarged cross-sectional view of the catheter system shown in FIG. 4, showing a close up of 13-13 of FIG. 12.
Figure 14:
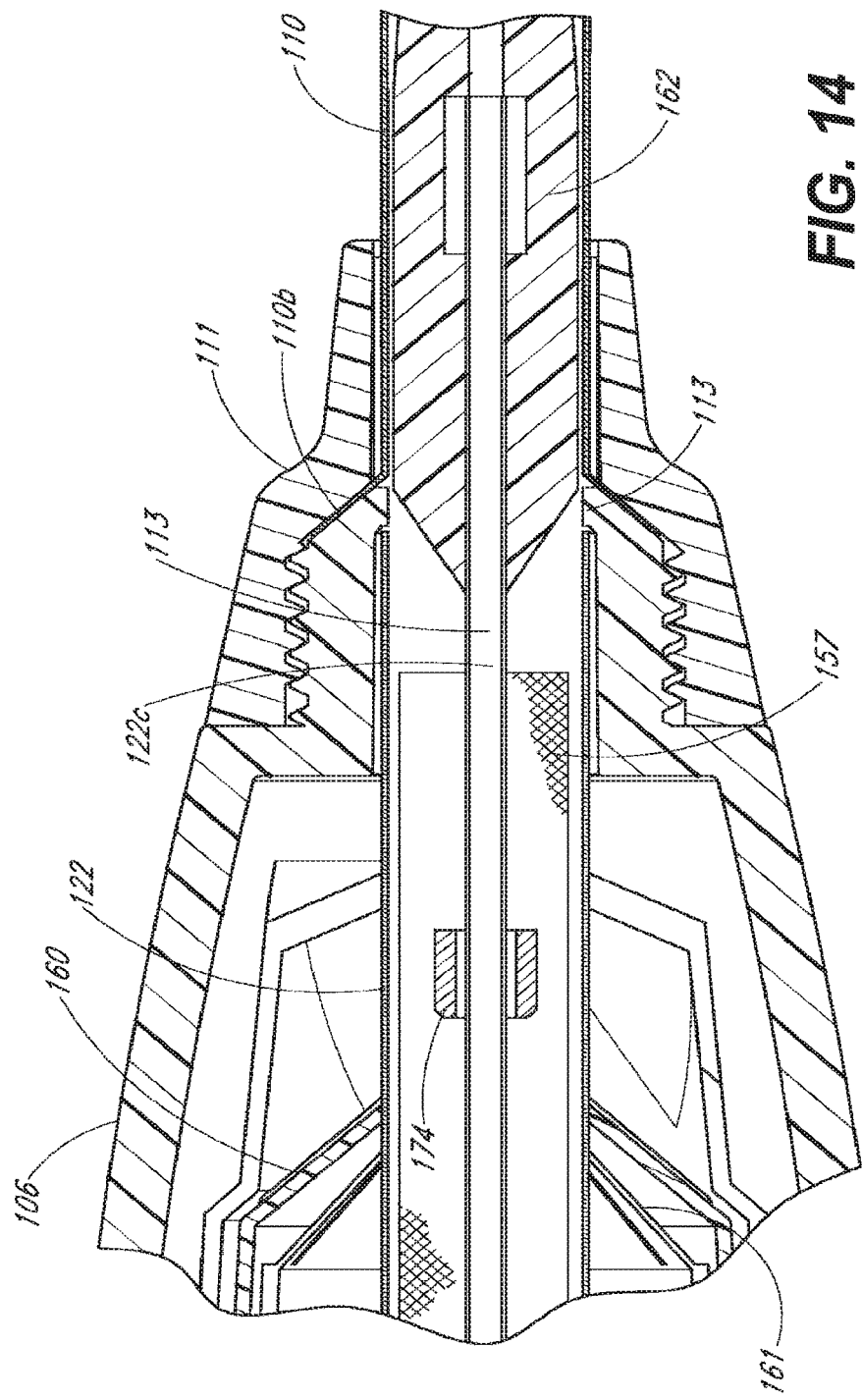
FIG. 14 is an enlarged section view of the catheter system shown in FIG. 4, showing a close up of 14-14 of FIG. 13.

FIG. 11 is an end view of the catheter system shown in FIG. 4, with the delivery catheter 104 engaged with the introducer 102. FIG. 12 is a section view of the embodiment of the catheter system 100 shown in FIG. 4, taken at line 12-12 of FIG. 11. FIG. 13 is an enlarged section view of the catheter system 100 shown in FIG. 4, defined by curve 13-13 of FIG. 12. FIG. 14 is an enlarged section view of the embodiment of the catheter system shown in FIG. 4, defined by curve 14-14 of FIG. 13. Finally, FIG. 15 is a section view of the catheter system shown in FIG. 4, taken at line 15-15 of FIG. 11.

Figure 15:
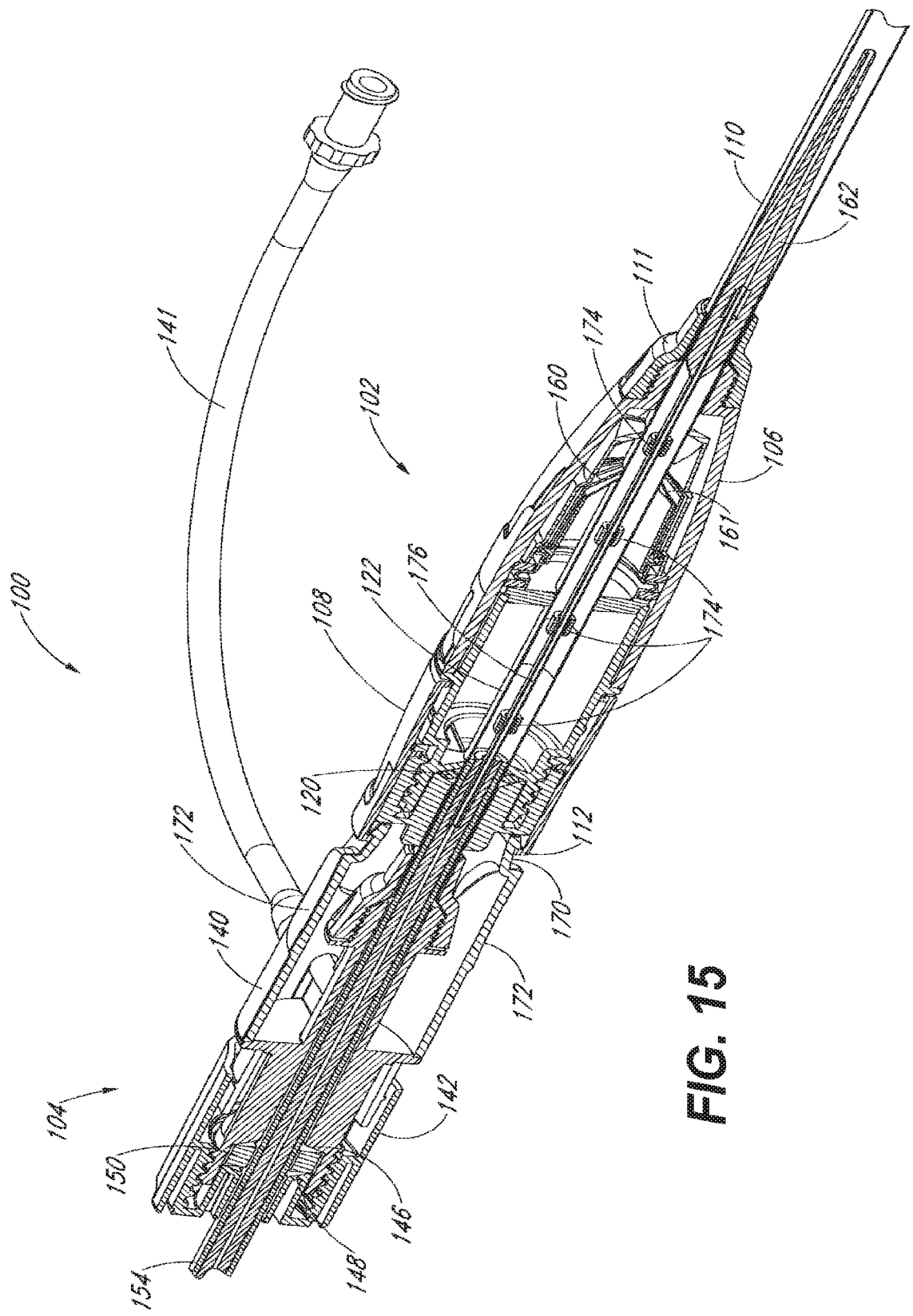
FIG. 15 is a cross-sectional view of the catheter system shown in FIG. 4, taken at line 15-15 of FIG. 11.

As shown most clearly in FIGS. 12 and 15, the hub portion 108 of the introducer 102 can have a docking mechanism or flange 112 or can be configured to removably receive or engage with the delivery catheter 104. In some embodiments, as in the illustrated embodiment, the docking mechanism 112 of the introducer 102 can be configured to be a female receiver, con-figured to receive a male docking member of the catheter 104, as will be described below. The hub portion 108 can comprise one or more tabs 114 configured to improve a user's grip on the hub portion 108, and ability to rotate the hub portion 108 relative to the main body 106.

With reference to FIGS. 12, 13, and 15, some embodiments of the seal portion of the introducer 102 will be described. As mentioned above, the hub portion 108 can be configured to be threadably engageable with the main body 106. The main body 108 can define an inner annular surface 116 that can be angled (so as to not be perpendicular to the axial centerline of the catheter system 100). The surface 116 can be angled approximately 75 degrees relative to the axial centerline of the catheter system 100, or from approximately 65 degrees or less to approximately 80 degrees or more relative to the axial centerline of the catheter system 100. The surface 116 can be approximately perpendicular to the axial centerline of the catheter system 100.

Similarly, the hub portion 108 can define an inner annular surface 118 that can be angled so as to not be perpendicular to the axial centerline of the catheter system 100. The surface 118 of the hub portion 108 can be angled approximately 75 degrees relative to the axial centerline of the catheter system 100, or from approximately 65 degrees or less to approximately 80 degrees or more and relative to the axial centerline of the catheter system 100 in a direction that is opposite to the direction of the angle defined by the surface 116 of the main body 106. In some embodiments, as in the illustrated embodiment, the shape and angular orientation of the surface 118 of the hub portion 108 can approximately mirror the shape and angular orientation of the surface 116 of the main body 106. The surface 118 can be approximately perpendicular to the axial centerline of the catheter system 100.

An annular seal member 120 can be supported by the introducer 102 and positioned between the surface 116 of the main body 106 and the surface 118 of the hub portion 108. The seal member 120 can be formed from a resilient material, such as silicone, rubber or any other suitable material. The seal member 120 can be configured such that, when the hub portion 108 is threaded onto the main body 106, the surface 118 of the hub portion 108 can be moved axially toward the surface 116 of the main body 106, thereby compressing or squeezing the seal member 120. The relative angles of the surface 116 of the main body 106 and the surface 118 of the hub portion 108 can cause the seal member 120 to be forced against an outer sheath 122 of the delivery catheter 104 or other component of the delivery catheter 104 that is engaged with the introducer 102, thereby creating an adjustable seal between the outer sheath 122 of the delivery catheter 104, which can project distally from an end portion of the delivery catheter 104, and the introducer 102. The level of seal can be adjusted by tightening or loosening the hub portion 108 of the introducer 102 relative to the main body 106 of the introducer 102. The introducer 102 can be configured to provide a seal against devices with a profile ranging from 1 Fr to 20 Fr.

Alternatively, in some embodiments, any of the seals or seal portions described herein can be an interference or close tolerance fit between adjacent components such as, the outer sheath 122 and one or more inside surfaces of the main body 106 or the hub portion 108 of the introducer 102. In some embodiments, any of the seals or seal portions described herein can be an interference or close tolerance fit between the inner core 154 and one or more inside surfaces of the main body 140 or the hub portion 142 of the catheter 104.

As shown in FIGS. 7, 8A, and 8B, some embodiments of the delivery catheter 104 can comprise a main body 140 and a hub portion 142 threadably engageable with the main body 140. Some embodiments of the delivery catheter 104 can also have an outer sheath 122 supported by the main body 140. In particular, the outer sheath 122 can be removably sup-ported by the main body 140 using a cap 123 threadably supported by the main body 140. Further, the outer sheath 122 can have an elongate portion 122a extending to any predetermined or desired length.

As mentioned above, the inside and/or outside diameter of the outer sheath 122 of a delivery catheter 104 can be approximately the same as or similar to the inside and/or outside diameter of the introducer sheath 110. The elongate portion 122a can be circular in cross-section (as illustrated), or can define any suitable cross-sectional shape such as without limitation triangular, square, hexagonal, octagonal, or polygonal.

The outer sheath 122 can have a flared end portion 122b that can be configured to abut against a fore surface 140a of the main body 140. With reference to FIG. 8A, the elongate portion 122a of the outer sheath 122 can pass through an opening formed in the cap 123 so that the flared portion 122b of the outer sheath 122 can be engaged with and/or overlap an inside surface of the cap 123. In this configuration, the cap 123 supporting the outer sheath 122 can be threadedly engaged with the main body 140 as mentioned above so that the outer sheath 122 is supported by the main body 140.

Additionally, with reference to FIGS. 8A and 8B, a tubular support or spacer 125 can be inserted over the elongate portion 122a of the outer sheath 122 and positioned approximately adjacent to the flared portion 122b of the outer sheath 122. The tubular spacer 125 can improve the fit and, hence, the seal between the outside surface of the outer sheath 122 and the cap 123. The tubular spacer 125 can also provide additional support to the outer sheath 122.

Similar to the hub portion 108 of the introducer 102, the hub portion 142 of the delivery catheter 104 can be configured to be threadably engageable with the main body 140 of the delivery catheter 104. The main body 140 can define an inner annular surface 146 that can be angled so as to not be perpendicular to the axial centerline of the catheter system 100. The surface 146 can be angled approximately 75 degrees relative to the axial centerline of the catheter system 100, or from approximately 80 degrees or more to approximately 65 degrees or less relative to the axial centerline of the catheter system 100. The surface 146 can be approximately perpendicular to the axial centerline of the catheter system 100.

In some embodiments, a second tube 141 can be supported by the main body 140 so as to provide an orifice or access port into the main body 140. The second tube 141 can be used to flush the delivery catheter 104 with saline or other suitable substances at any stage, such as but not limited to prior to the advancement of an endoluminal prosthesis through the delivery catheter 104 and/or introducer 102, or prior to other procedures for which an delivery catheter may be used. The second tube 141 can support any suitable medical connector and/or valve on the distal end thereof.

Similarly, the hub portion 142 can define an inner annular surface 148 that can be angled so as to not be perpendicular to the axial centerline of the catheter system 100. The surface 148 of the hub portion 142 can be angled approximately 75 degrees relative to the axial centerline of the catheter system 100, or from approximately 65 degrees or less to approximately 80 degrees or more relative to the axial centerline of the catheter system 100 in a direction that is opposite to the direction of the angle defined by the surface 146 of the main body 140. The surface 148 can be approximately perpendicular to the axial centerline of the catheter system 100.

Similar to that of the introducer, in some embodiments, a seal or seal portion comprising an annular seal member 150 can be supported by the delivery catheter 104 and positioned between the surface 146 of the main body 140 and the surface 148 of the hub portion 142. The seal member 150 can be formed from a resilient material, such as silicone, rubber or any other suitable material. The seal member 150 can be configured such that, when the hub portion 142 is threaded onto the main body 140, the surface 148 of the hub portion 142 can be moved axially toward the surface 146 of the main body 140, thereby compressing or squeezing the seal member 150. The relative angles of the surface 146 of the main body 140 and the surface 148 of the hub portion 142 can cause the seal member 150 to be forced against the inner core 154 of the delivery catheter 104, thereby creating an adjustable seal between the inner core 154 the outer sheath 122 of the delivery catheter 104.

The level of seal can be adjusted by tightening or loosening the hub portion 142 of the delivery catheter 104 relative to the main body 140 of the delivery catheter 104. Additionally, The rotational freedom of inner core 154 of the delivery catheter 104 can be inhibited or prevented by tightening the seal member 150 as described above. Thus, the force exerted by the seal member 150 on the inner core 154 can be adjusted to permit the inner core 154 and/or other components to rotate relative to the main body 140 and hub portion 142 of the delivery catheter 104. As illustrated in FIG. 4, an end portion or cap 158 can be supported at the proximal end of the inner core 154 to facilitate a user's ability to axially slide and/or rotate that inner core 154 relative to the main body 140 and hub portion 142 of the delivery catheter 104. The cap 158 can have wings or tabs formed thereon to increase the torque or rotational force that can be exerted on the inner core 154. Alternatively, The seal or seal portion within the catheter 104 can be formed from an interference or close tolerance fit between adjacent components such as, without limitation, the inner core 154 and one or more inside surfaces of the main body 140 or the hub portion 142 of the catheter 104.

The inner core 154 can have a band or other marking 155 near a distal end thereof. The marking 155 can be sized, positioned, and configured to provide a visual indication to the medical practitioner as to the location of the end portion 154a of the inner core 154 and/or the location of a catheter tip 162 as the inner core 154 is being advanced into or withdrawn from the introducer 102.

In some embodiments, as illustrated most clearly in FIGS. 12 and 13, an additional seal member 160 can be supported by the main body 106 of the introducer 102 to provide an additional seal between the outer sheath 122 of the delivery catheter 104 and the introducer 102. The seal 160 can be a flap type seal formed from a conically shaped piece of resilient material such as, but not limited to, rubber having one or more slits therein to allow the distal tip 162 and the outer sheath 122 to pass therethrough. In some embodiments, a supported flange 161 can be supported within the main body 106 and positioned behind the seal 160 to support the seal 160 and maintain the position of the seal 160 so that the seal 160 does not become inverted when the delivery catheter 104 is removed from the introducer 102. The distal tip 162 can be formed from a soft material such as rubber and can be configured to be atraumatic so as to prevent any damage to a patient's vasculature as the catheter 104 is being advanced through the patient's vasculature.

As mentioned above, in some embodiments, as in the illustrated embodiment, the docking mechanism 112 of the introducer 102 can be configured to receive a male docking member or portion of the catheter 104. In particular, with reference to FIGS. 7, 8A and 8B, one or more deflectable tabs 170 can be supported by the main body 140 of the catheter 104. The tabs 170 can be deflected by pressing or exerting a radial inward force against pads 172, causing the ends of the tabs 170 to move radially inward toward the axial centerline of the main body 104. By deflecting the tabs 170 inwardly, the main body 140 of the catheter 104 can be moved axially into engagement with the hub portion 108 of the introducer 102. The tabs 170 can be automatically deflected inwardly when the main body 140 of the catheter 104 is moved axially into engagement with the hub portion 108 of the introducer 102. Once the main body 140 of the catheter 104 is moved axially into engagement with the hub portion 108 of the introducer 102 so as to abut against the hub portion 108 of the introducer, the tabs 170 can be released, thereby removably locking the main body 140 of the catheter 104 to the hub portion 108 of the introducer 102.

In this configuration, the catheter 104 can be axially engaged with or locked to the introducer 102 so that a user can axially manipulate the introducer 102 and the catheter 104 simultaneously. Additionally, in some embodiments, in this configuration, as discussed above, the catheter system 100 can be configured such that at least the inner core 154 of the catheter 104 can be rotated relative to the main body 140 of the catheter 104 and the introducer 102.

In some embodiments, as shown in FIGS. 7, 8A, and 8B, the inner core 154 has a central tube or wire 176 configured to support a stent, such as stent 157 illustrated in FIGS. 7 and 12-1.4. Additionally, one or more beads or tabs 174 can be formed on or supported by the central tube or wire 176. The tabs 174 can be configured to increase the axial support or connection between the inner core 154 and an endoluminal prosthesis supported by the central tube 176 when the prosthesis is supported in a collapsed configuration by the central tube 176. The catheter 104 can be configured such that an opening passes through the distal tip 162, the central tube 176, and the inner core 154. The opening can be configured so that at least the distal tip 162, the central tube 176, and the inner core 154 can be advanced over a guidewire positioned within a patient's vasculature, such as is described in U.S. patent application Ser. No. 12/101,863 filed on Apr. 11, 2008 (titled: BIFURCATED GRAFT DEPLOYMENT SYSTEMS AND METHODS), which application is hereby incorporated by reference in its entirety as if fully set forth herein.

Additionally, in some embodiments (not illustrated), the tabs 174 can be sized, spaced, and otherwise configured to provide axially support to multiple individual stent segments. For example, without limitation, multiple independent or tethered stent segments can be positioned within a tubular or bifurcated graft, and the stent graft can be positioned relative to the tabs 174 such that the tabs 174 are positioned between the stent segments. This arrangement can reduce the overall diameter of the outer sheath 122, the introducer sheath 110, and other components comprising the catheter system, can enhance the axial support provided by the tabs 174 to the endoluminal prosthesis, and can allow for a more uniform distribution of support forces between the tabs 174 and the endoluminal prosthesis. The tabs 174 can be sized, spaced, and otherwise configured so as to be positioned adjacent to the links, bends, loops, and/or other connectors formed in a tubular or bifurcated stent, such as the links, bends, loops, and/or other connectors comprising the embodiments of the stents disclosed in U.S. Pat. No. 6,077,296 titled ENDOLUMINAL VASCULAR PROSTHESIS, which patent is hereby incorporated by reference as if fully set forth herein.

With reference to FIGS. 13-15, the outer sheath 122 of the deployment catheter 104 can be advanced into an axial opening within the introducer 102 when the deployment catheter 104 is engaged with the introducer 102. The outer sheath 122 can be sized and configured such that the distal end portion 122c of the outer sheath 122 can terminate within the introducer 102 prior or proximal to the proximal end or flared portion 110b of the introducer sheath 110. Although not required, the introducer 102 can have a constricted portion 113 formed in the main body 106 of the introducer. In some embodiments, as shown most clearly in FIG. 14, the catheter system 100 can be configured such that the distal end 122c of the outer sheath 122 terminates prior to or approximately adjacent to a constricted portion 113 of the main body 106 of the introducer 102.

In some embodiments (not illustrated), the distal end portion 122c of the outer sheath 122 can be positioned near to or approximately adjacent to the proximal end portion or the flared portion 110b of the introducer sheath 110, regardless of whether the catheter 104 has a constricted portion 113. The inner diameter of the constricted portion 113 can be approximately the same as the inner diameter of the outer sheath 122 and/or the inner diameter of the introducer sheath 110.

Therefore, The outer sheath 122 of the catheter 104 and the introducer sheath 110 can be configured to provide a lumen having a generally uniform cross-sectional size through the catheter system through which the endoluminal prosthesis can be advanced. The lumen through the catheter system 100 through which the endoluminal prosthesis can be advanced can be substantially continuous, so that the endoluminal prosthesis can be advanced through the catheter system 100 without the pros-thesis being obstructed by or snagging on any components or features of the catheter system 100 as it is being advanced. The lumen can be substantially continuous but have short gaps on the order of approximately 1 mm to approximately 3 mm in the lumen such as, without limitation, adjacent to the distal end of the outer sheath 122 of the catheter 104 and/or adjacent to the proximal or flared end 110*b* of the introducer sheath 110. For example, in some embodiments, short gaps can be formed adjacent to the distal end of the outer sheath 122 of the catheter 104 and/or adjacent to the proximal or flared end 110*b* of the introducer sheath 110 as some components comprising the catheter system 100 are threadedly engaged with other components comprising the catheter system 100. Further, in some embodiments, one or more surfaces of other components comprising the catheter 104 or the introducer 102 in addition to the outer sheath 122 and the introducer sheath 110, such as without limitation the constricted portion 113 of the main body 106 of the introducer 102 as discussed above, can form portions of the lumen through the catheter system 100.

The outer sheath 122 can constrain or restrain an endoluminal prosthesis supported by the central tube 176 as described above. In this configuration, as the catheter tip 162, central core 154, and an endoluminal prosthesis (such as, but not limited to, stent 157 illustrated in FIGS. 7 and 12-14) are advanced through the outer sheath 122, the outer sheath 122 can restrain the endoluminal prosthesis and prevent the endoluminal pros-thesis from expanding before reaching the target position within the patient's vasculature. Additionally, the catheter system 100 can be configured such that, as the catheter tip 162, central core 154, and endoluminal prosthesis are advanced past the distal end 122*c* of the outer sheath 122, the constricted portion 113 and, subsequently, the introducer sheath 110 can radially restrain the endoluminal prosthesis as the endoluminal prosthesis is advanced through the introducer sheath 110.

The endoluminal prosthesis or the stent 157 can be a tubular stent, a bifurcated stent, or any other desirable stent, graft, stent graft, or endoluminal prosthesis (collectively referred to herein as stent or stents), including without limitation any of the stents or grafts disclosed in U.S. patent application Ser. No. 12/101,863 referenced above and incorporated herein by reference as if fully set forth herein. Accordingly, the catheter system 100 or catheter 104 can be configured to deploy any suitable or desirable stent or stents.

Thus, in this configuration, the endoluminal prosthesis can be transferred from the outer sheath 122 to the introducer sheath 110. In this arrangement, using the introducer sheath 110 as the restraint can allow the outside diameter of the introducer sheath 110 to be reduced, which can minimize trauma to the patient's vasculature and assist in the deployment of the endoluminal prosthesis.

Many embodiments of the docking mechanism and catheter system have been described in connection with FIGS. 1-15. It will apparent to one of ordinary skill in the art that there are many potential embodiments of a permanent or removable docking mechanism that may be suitable for medical use and which are contemplated herein. For example, in some embodiments, a nut-screw combination could be used to connect the introducer sheath and the catheter. As another example, a bayonet style locking mechanism, such as is used for camera lenses, can also be used. In some embodiments, any of the components or features of some embodiments of the catheters disclosed herein or other catheters available in the field can be combined to form additional embodiments, all of which are contemplated herein.

Figure 16:
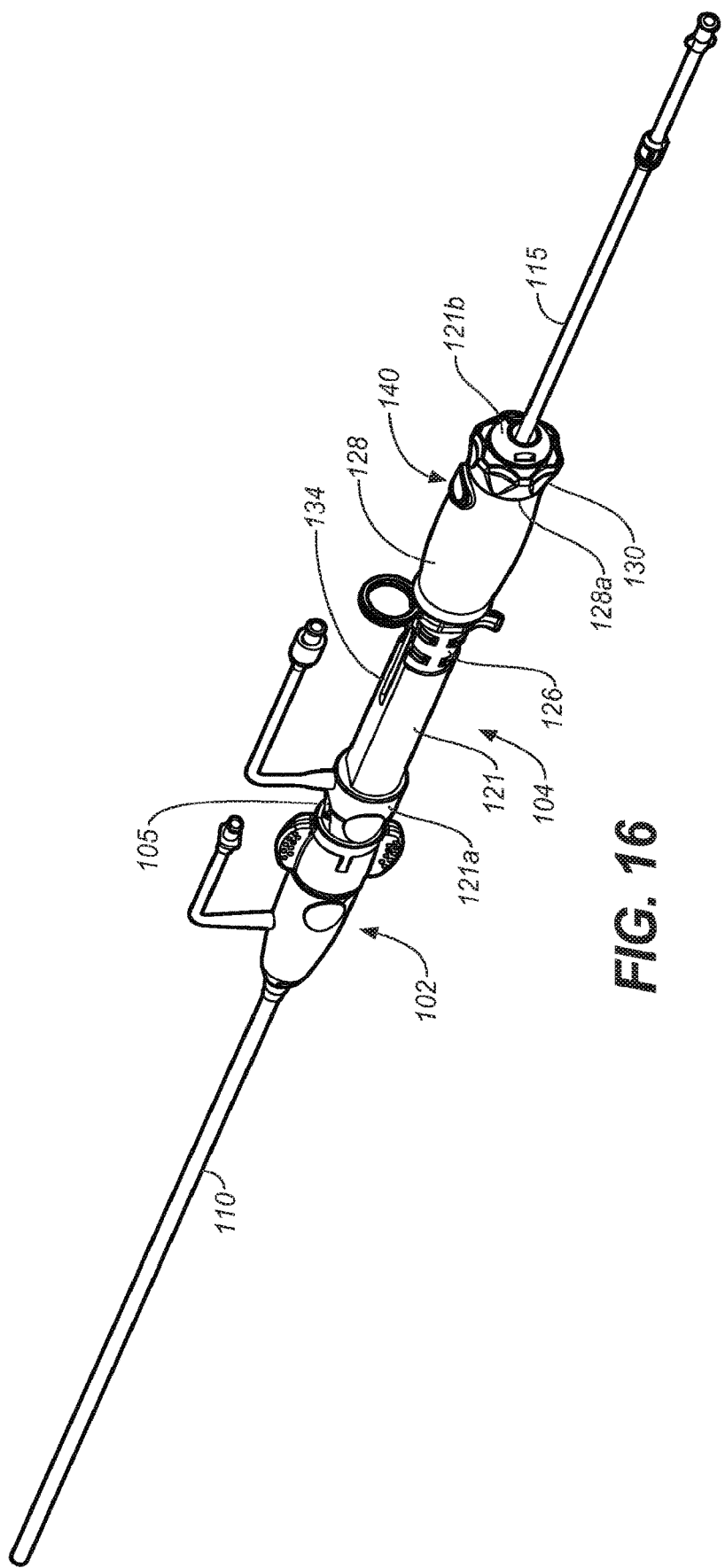
FIG. 16 is an oblique view of a catheter system, having a delivery catheter assembly docked to an introducer catheter assembly.

The catheter system disclosed in FIG. 16 has an introducer catheter assembly, also referred to herein as an introducer catheter, and a delivery catheter assembly, also referred to herein as a delivery catheter.

The catheter systems disclosed herein can be used for diagnostic or therapeutic procedures such as, but not limited to, endoluminal vascular prosthesis deployment procedures. It should be apparent to one skilled in the art that the catheter system embodiments disclosed herein can be used for delivering prostheses for supporting body tissue in general as well as various blood vessels and aneurysms. Examples of such blood vessels that can be treated with the catheter system embodiments disclosed herein include the aorta, aortic aneurysms such as abdominal aortic aneurysms, saphenous vein grafts, the vena cava, the renal arteries, the iliac arteries, the femoral arteries, the popliteal artery, the carotid artery, the cranial arteries, pulmonary arteries, etc. Other organs or body tissue that can be treated with some catheter system embodiments disclosed herein include the prostate, the biliary tract, the esophagus, the trachea, the fallopian tubes, the vas deferens, the ureters, the tear ducts, the salivary ducts.

The catheter systems disclosed herein can be configured for deployment of a wide range of endoluminal prostheses, including mechanically expandable stents, self-expanding stents, drug eluting stents, grafts, bifurcated and non-bifurcated stent grafts, fenestrated stent grafts, suprarenal stent extensions, stent segments, dissection treatment devices, medical prostheses deployable in any suitable region of the body, and any of the stents or prostheses disclosed in U.S. application Ser. No. 12/101,863, filed Apr. 11, 2008. U.S. application Ser. No. 12/496,446, filed Jul. 1, 2009, U.S. application Ser. No. 12/769,506, filed Apr. 28, 2010, and U.S. Pat. No. 6,077,296, which are hereby incorporated by reference as if fully set forth herein.

The stent can have an oversized graft have a mid portion that is not sutured or otherwise attached to the stent frame. In this configuration, the mid portion can be permitted to expand against an inside wall of the vessel or passageway to further improve the seal between the graft and the vessel wall. Additionally, the stent can have an oversized graft of highly collapsible, flexible material (e.g., expanded polytetrafluoroethylene) such that, when the stent is expanded, the graft can form tight folds in the seal zone to reduce cross-sectional area of leak zones between the stent and the vessel wall.

For simplicity, all such foregoing stents or prostheses are collectively referred to herein as a stent or stents unless otherwise defined. Therefore, while illustrations and the disclosure that follows may describe stents and may show deployment in a particular passageway or in a region of the body, it is contemplated that any of the embodiments disclosed herein can be used, with or without modifications within the capabilities of one of ordinary skill in the art, for deployment of any desired prosthesis in any suitable portion of the body.

Figure 17:
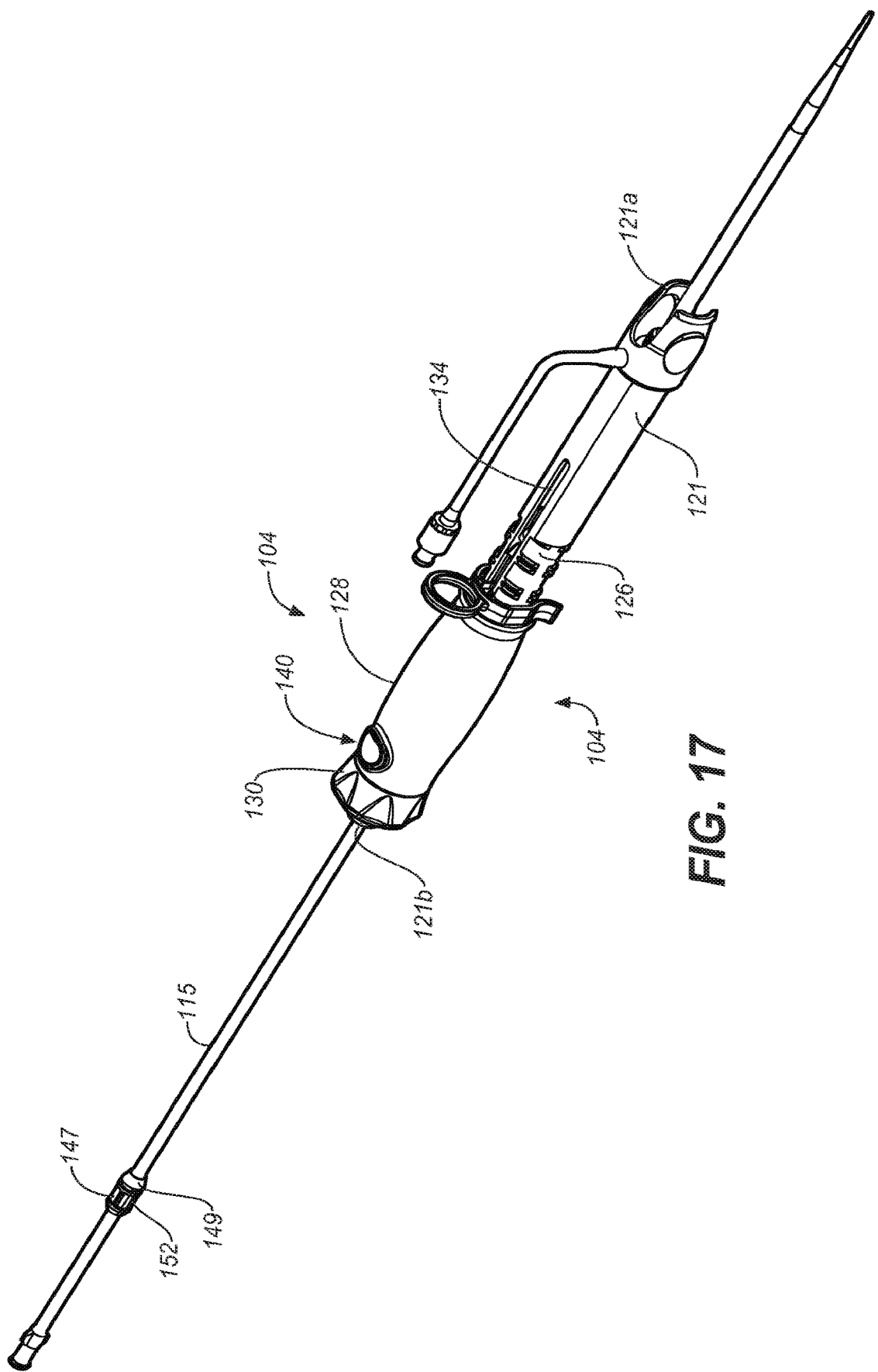
FIG. 17 is an oblique view of the delivery catheter assembly of FIG. 16.

FIG. 16 is an oblique view of a catheter system 100, having a delivery catheter assembly 104 docked to an introducer catheter assembly 102. FIGS. 17-19 are oblique, top, and side views, respectively, of the delivery catheter assembly 104 of FIG. 1. With reference to FIGS. 16-17, the catheter system 100 has a docking arrangement wherein a proximal end portion of an introducer catheter assembly 102 can receive and dock with a distal end portion 121a of the main body 121 (also referred to herein as housing member or housing shaft) of a delivery catheter assembly 104. The introducer catheter 102 can have an outer sheath 110 (also referred to herein as an introducer sheath) supported by and extending from a distal end portion of the introducer catheter 102. Similarly, the delivery catheter assembly 104 has a tubular sheath 127 (also referred to herein as a delivery catheter sheath) extending from a distal end portion 121a of the housing shaft 121. The sheath 127 can be made from polyether ether ketone (PEEK), or any other suitable material.

Additional details regarding the features and components of such a docking arrangement and other details regarding the catheter system are disclosed in U.S. application Ser. No. 12/101,863, filed Apr. 11, 2008, entitled "BIFURCATED GRAFT DEPLOYMENT SYSTEMS AND METHODS" and U.S. application Ser. No. 12/496,446, filed Jul. 1, 2009, entitled "CATHETER SYSTEM AND METHODS OF USING SAME." both incorporated by reference as if fully set forth herein. Any of the embodiments of the catheter systems, the delivery catheters, and the introducer catheters disclosed herein can have any of the components, features, materials, or other details of any of the embodiments of the catheters disclosed in the foregoing applications, which combinations are made part of this disclosure.

One or more stents can be loaded in, supported by, and delivered by the catheter system 100 embodiments disclosed herein. A stent or stents can be loaded into the delivery catheter assembly 104 during assembly of the delivery catheter assembly 104 or just before the surgical procedure by compressing the stent around an outer surface of an inner core member 115 of the delivery catheter assembly 104.

A removable restraint and/or an outer sheath of the introducer catheter and/or delivery catheter can hold the stent in a compressed state. In the compressed state, the stent can be held in a generally fixed axial position relative to the inner core such that axial or rotational movement of the inner core will result in axial and rotationally movement of the stent. As will be discussed, the inner core can have features, such as fins, beads, tabs, or other projections, to improve the traction or grip between the compressed stent and the inner core or inner core wire, the inner core with the stent compressed around the outer surface thereof will be advanced through a constriction element in or adjacent to the introducer catheter to compress the stent to the approximate inner diameter of the outer sheath projecting from the introducer catheter.

The inner core member 115 can have a core wire 117 forming a portion of the inner core member 115. An atraumatic distal tip 119 can be supported at a distal end portion of the core wire 117. The inner core member 115, core wire 117, and the distal tip 119 can comprise a continuous lumen therethrough, being configured to receive a guide wire therein such that the inner core member 115, the core wire 117, and the distal tip 119 can be advanced over the guide wire, the stent can be collapsed or compressed about at least a portion of the inner core wire 117 in the stent loaded condition.

As mentioned, the catheter system can be configured such that the inner core member 115 is axially slidable relative to the outer sheath 110. In this configuration, the stent can be deployed in the target region of the patient's vasculature by retracting the outer sheath 110 relative to the inner core member 115, thereby exposing the stent. In some embodiments where the outer sheath 110 provides radial constraint to the stent, exposing the stent will permit a self-expanding stent to self-expand against the vessel wall as the outer sheath 110 is being retracted.

As will be described in greater detail, some embodiments of the catheter system 100 disclosed herein are configured such that, when a user or surgeon manipulates the delivery catheter assembly 104 slowly and with mechanical advantage in a first manner, the delivery catheter can be used to slowly and controllably deploy a stent or a portion of a stent from the delivery catheter assembly 104. Some embodiments of the catheter system disclosed herein are further configured such that, when a user or surgeon manipulates the delivery catheter assembly 104 quickly by directly pulling the adjustment member in a second manner, the delivery catheter assembly 104 is used to more rapidly deploy the stent or a portion of the stent from the delivery catheter assembly 104.

The catheter systems disclosed herein can be configured to accommodate any combination of the manners of deployment described above. For example, the user or surgeon can initially manipulate the delivery catheter in the first manner to slowly deploy the stent from the delivery catheter assembly 104 and then, once the proper positioning of the partially deployed stent is confirmed, the surgeon can then manipulate the delivery catheter assembly 104 in the second manner to rapidly deploy the remainder of the stent.

With reference to FIG. 16, a distal end portion 121a of the housing shaft 121 of the delivery catheter assembly 104 is removably and axially supported by a female receiving portion 105 supported at a proximal end portion of the introducer catheter 102. The introducer catheter 102 supports an outer sheath 110 at a distal end thereof, the outer sheath 110 defining a lumen therethrough that is configured to slidably receive an inner core member 115 therein. The inner core member 115 can be slidably advanced through an opening or lumen in the delivery catheter assembly 104, through an opening or lumen in the introducer catheter 102, and through a lumen in the outer sheath 110.

The delivery catheter assembly 104 has a main body or housing shaft 121 having a distal end portion 121a and a proximal end portion 121b. The housing shaft 121 pounds a generally tubular cross-sectional shape, and has external threads 126 along a portion of the housing shaft 121 (referred to as the threaded portion 126).

The housing shaft 121 supports a slidable handle member 128 that can be configured to slide axially along the housing shaft 121 between the distal end portion 121a of the housing shaft 121 and an rotatable adjustment member 130 supported by the housing shaft 121. As will be described, the delivery catheter assembly 104 is configured such that the handle member 128 is selectively engageable with the inner core member 115. When in the engaged configuration, movement of the handle member 128 results in simultaneous and equal movement of the inner core member 115, the delivery catheter assembly 104 can be configured such that the handle member 128 is prevented from rotating relative to the housing shaft 121 and, consequently, the introducer catheter 102 and outer sheath 110, to prevent any inadvertent rotation of the inner core member 115 when the handle member 128 is engaged with the inner core member 115.

The threaded portion 126 extends along approximately 60% of the length of the housing shaft 121. The threaded portion 126 can extend along approximately 40% to approximately 70% of the length of the housing shaft 121. The threaded portion 126 can be positioned adjacent to the proximal end portion 121b of the housing shaft 121. The length of the threaded portion 126 can be from approximately 20% to approximately 200% of the length of the stent to be deployed by the catheter. For example, if only the proximal end portion of the stent is to be deployed by rotation of the adjustment member 130, the length of the threaded portion can be approximately from 20% to approximately 50% of the length of the stent. As used throughout this disclosure, the term approximately can mean plus or minus 15% of the stated value.

Preventing the rotational movement of the handle member 128 can be achieved in any number of ways. For example, the handle member 128 has a tab, protrusion, or similar feature or features that can project into one or more channels or slots formed in the housing shaft 121. As illustrated in FIG. 16, the housing shaft 121 can have a single slot 134 extending in a linear fashion along a portion of the length of the housing shaft 121, the slot 134 configured to slidingly receive therein a tab, protrusion, or other similar feature supported by the handle member 128.

The handle member 128 pounds an inner core engagement assembly 139 supported by the handle member 128. As mentioned, the delivery catheter assembly 104 is configured such that, when the inner core member 115 is axially engaged with the handle member 128, any axial movement of the handle member 128 will result in simultaneous axial movement of the inner core member 115 relative to the introducer catheter 102 and the outer sheath 110. Depressing the inner core engagement assembly 139 can release the inner core member 115 from the handle member 128 so that the inner core member 115 can be axially moved relative to the handle member 128. In some configurations, the inner core member 115 can be rotated relative to the handle member 128 even when the inner core member 115 is axially engaged with the handle member 128.

As mentioned, the rotatable adjustment member 130 is supported by the housing shaft 121. The rotatable adjustment member 130 is threadedly engaged with the outer threads on the threaded portion 126 of the handle member 128. In this configuration, rotating or turning the rotatable adjustment member 130 in one direction causes the rotatable adjustment member 130 to advance along the threads and move in an axial direction toward the distal end portion 121a of the housing shaft 121. Rotating or turning the rotatable adjustment member 130 in a second, opposite direction causes the rotatable adjustment member 130 to move in an axial direction away from the distal end portion 121a of the housing shaft 121 of the delivery catheter assembly 104. As a result of the threaded engagement between the rotatable adjustment member 130 and the housing shaft 121, the rotatable adjustment member 130 can be prevented from axially sliding relative to the housing shaft 121. Accordingly, the handle member 128 can axially slide but be prevented from rotating relative to the housing shaft 121, and the rotatable adjustment member 130 can rotate but be prevented from axially sliding relative to the housing shaft 121.

In use, a surgeon may grasp the handle member 128 with one hand (for example, the left hand) and the rotatable adjustment member 130 (which is initially axially positioned adjacent the proximal 130a of the housing shaft) with the other hand. The surgeon moves the inner core member 115 to engage with the handle member 128. To retract the outer sheath 110 of the introducer catheter 102 relative to the inner core member 115, the surgeon holds the handle member 128 in a fixed position while axially withdrawing the housing shaft 121 of the delivery catheter assembly 104, which is axially fixed to the introducer catheter 102 and to the outer sheath 110. Holding the handle member 128 in a fixed position, with the inner core engagement (and release) assembly 139 engaged with the inner core member 115, holds the inner core member 115 fixed as the outer sheath 110 is axially retracted relatively inner core member 115 fixed to the housing shaft 121. Retracting the housing shaft 121 portion of the delivery catheter assembly 104 can be done by grasping and rotating the rotatable adjustment member 130 or directly by applying a pull force to retracting the rotatable adjustment member 130 relative to the handle member 128. This step causes withdrawal of the outer sheath 110 relative to the inner core member 115 is desired.

The slower incremental withdrawal of the outer sheath 110 relative to the inner core member 115 is accomplished as the rotatable adjustment member 130 axially abuts a proximal end 128a of the handle member 128. Rotating the rotatable adjustment member 130 in a first direction while holding the handle member 128 in a fixed axial position will slowly and incrementally and controllably retract or withdraw the housing shaft 121 of the delivery catheter assembly 104 and, consequently, the outer sheath 110. This controlled withdrawal of the outer sheath 110 is usually performed during the initial deployment phase of exposing and deploying a stent, to allow the surgeon greater control and accuracy in positioning the stent in the target location.

In sum, in this configuration, with the handle member 128 initially positioned on a proximal portion of the housing shaft 121, a surgeon can controllably retract the outer sheath 110 to expose the stent by holding the handle member 128 in a fixed position relative to the patient in one hand, while using his or her other hand to turn the rotatable adjustment member 130 in a first direction to retract the housing shaft 121 and outer sheath 110 relative to the handle member 128 and inner core member 115. Once the surgeon is confident that the stent is in the desired position, the surgeon can then more rapidly retract the outer sheath 110 relative to the inner core member 115 by grabbing and axially retracting the housing shaft 121 relative to the handle member 128.

As illustrated in FIGS. 17-19, the delivery catheter assembly 104 can have a selectively engageable locking feature positioned on the inner core member 115, such as the lock engagement ring 147. As will be described in greater detail below, the engagement ring 147 can be configured to removably engage with the inner core engagement assembly 139. As discussed above, when the inner core member 115 is engaged with the engagement assembly 139, the inner core member 115 is axially locked to the engagement assembly 139 such that axial movement of the handle member 128 results in simultaneous axial movement of the inner core member 115, the inner core member 115 can be free to rotate relative to the engagement assembly 139 and the handle member 128 even when in the locked or engaged position. The engagement ring 147 can be adhered to, integrally formed with, or otherwise permanently fixed to an outer surface of the inner core member 115.

With reference to FIGS. 17-19, some embodiments of the engagement ring 147 can have a tapered surface 149 and an annular channel 152. The tapered surface 149 can improve the ease with which the engagement ring 147 can be advanced into the engagement assembly 139. Additional details regarding these components will be described below.

Figure 20:
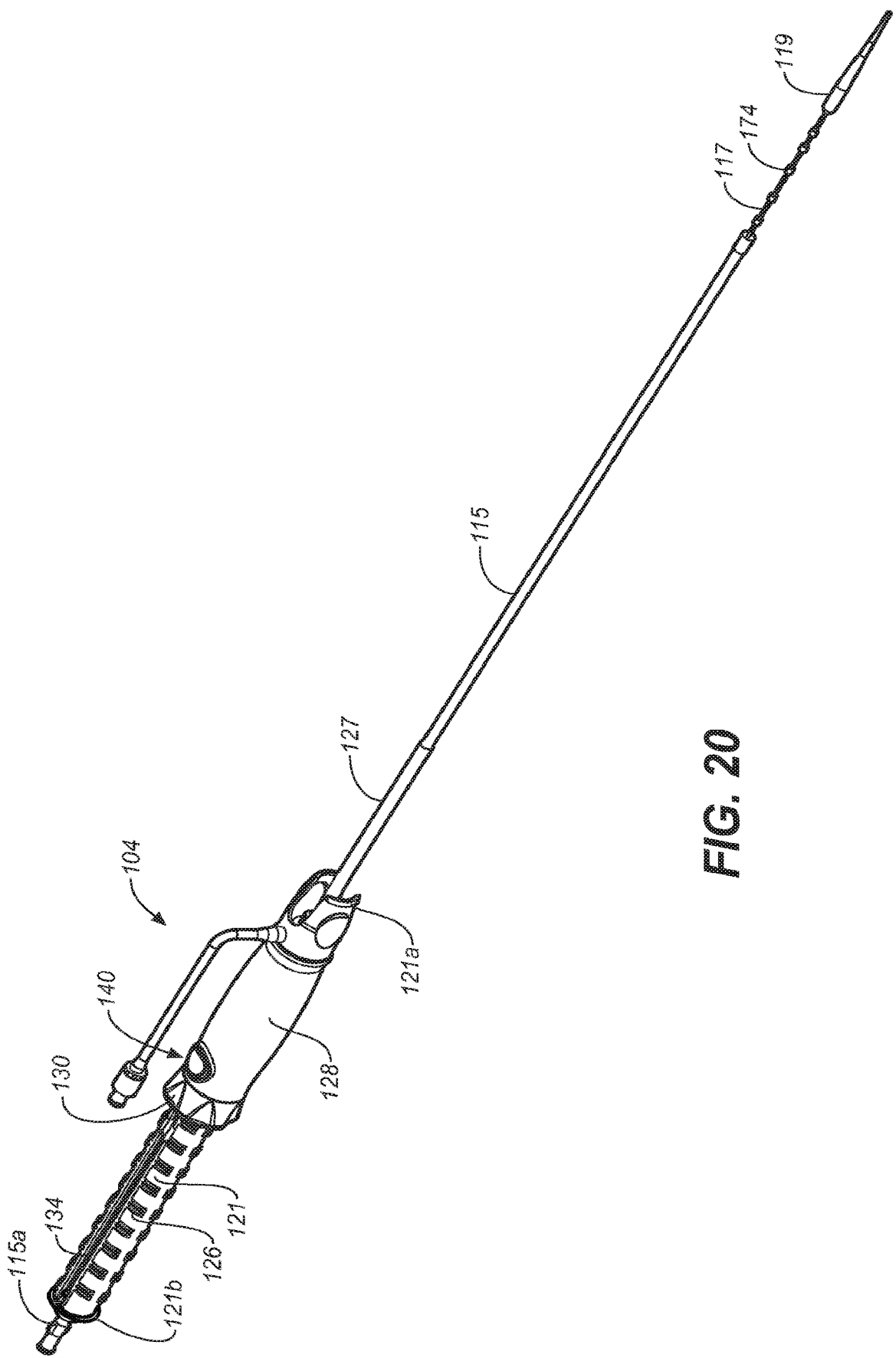
FIG. 20 is an oblique view of the delivery catheter assembly of FIG. 16, illustrating the sheath in a fully retracted position relative to the inner core member.

FIG. 20 is an oblique view of the delivery catheter assembly 104 of FIG. 16, illustrating the inner core member 115 in a fully or approximately fully advanced position relative to the delivery catheter assembly 104. In this position, the inner core member 115, the inner core wire 117, and the distal tip 119 are all advanced past the end of the sheath 127 of the delivery catheter assembly 104. When the delivery catheter assembly 104 is engaged with the introducer catheter 102, the inner core member 115, the inner core wire 117, and the distal tip 119 are also be advanced relative to the end of the outer sheath 110 such that a stent supported by the inner core member 115 would be at least partially, and in some cases fully, exposed.

Figure 21:
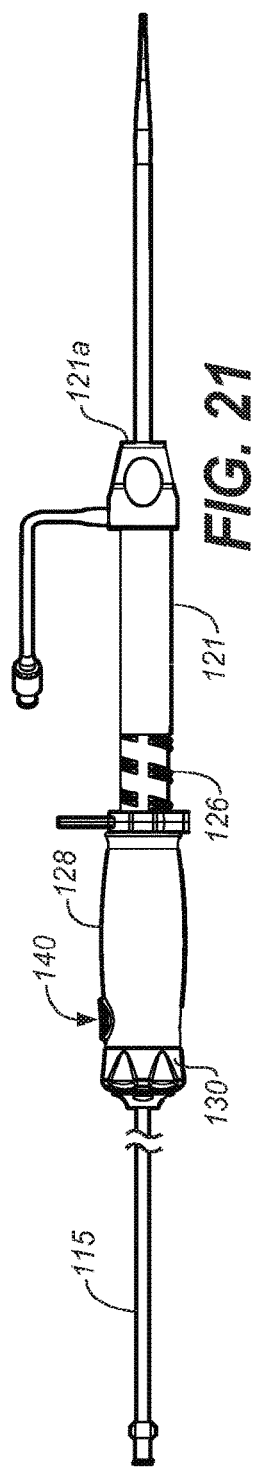
FIG. 21 is a side view of the delivery catheter of FIG. 16, showing the handle member and the inner core in a pre-deployment first position relative to the housing shaft of the delivery catheter.
Figure 22:
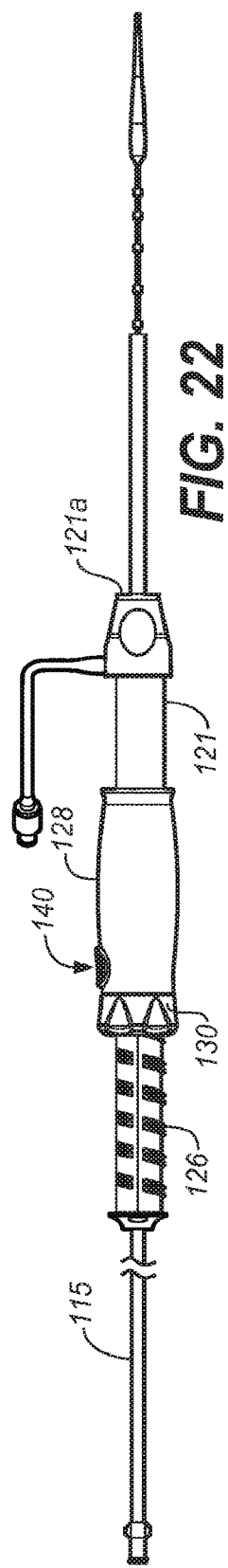
FIG. 22 is a side view of the delivery catheter of FIG. 16, showing the handle member and the inner core in a second, partial deployment position relative to the housing shaft of the delivery catheter.
Figure 23:
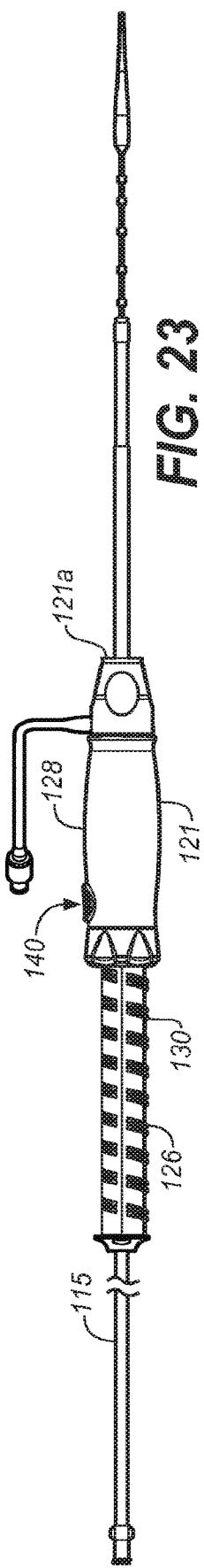
FIG. 23 is a side view of the delivery catheter of FIG. 16, showing the handle member and the inner core in a third, fully advanced position on the housing shaft of the delivery catheter.

FIGS. 21-23 are side views of the delivery catheter of FIG. 16, showing the sheath in a first, pre-deployment position, a second, partial deployment position, and a third, fully retracted position, respectively, and the positions of the housing shaft 121, handle member 128, and the inner core member 115 of the delivery catheter assembly 104. The delivery catheter assembly 104 is configured such that the handle member 128 slides along the housing shaft 121 between the first position, as illustrated in FIG. 21, and at least a third position, as illustrated in FIG. 23. Therefore, in this configuration, the handle member 128 is held stationary while the user or surgeon can retract the housing shaft 121 by sliding it relative to the handle member 128. Accordingly, when the handle member 128 is engaged with the inner core member 115, a surgeon can very rapidly advance the inner core member 115 relative to the distal end portion 121a of the housing shaft 121 of the delivery catheter assembly 104 by sliding the handle member 128 toward the distal end portion 121a of the housing shaft 121. Similarly, if the surgeon desires to hold the inner core member 115 and prosthesis in a fixed position within the patient's vasculature, the surgeon or user can hold the handle member 128 in a fixed position and axially slide or retract the delivery catheter assembly 104 away from the patient's body so as to retract the outer sheath 110 of the introducer catheter 102 relative to the inner core member 115 and prosthesis, thereby exposing the prosthesis.

The rotatable adjustment member 130 is separable from the handle member 128 so that the adjustment member 130 and housing shaft 121 can move independently of the handle member 128. The adjustment member 130 includes inside threads that engage with the external threads on the threaded portion 126 of the housing shaft 121. Rotating the adjustment member 130 in a first direction axially retracts the housing shaft 121 and sheath as the adjustment member 130 maintains contact with the handle member 128 as the adjustment member rotates. Rotation of the adjustment member 130 is used to control the speed of slow retraction of the housing shaft 121 or an axial force applied to the adjustment member provides the option of a quick retraction.

Figure 24:
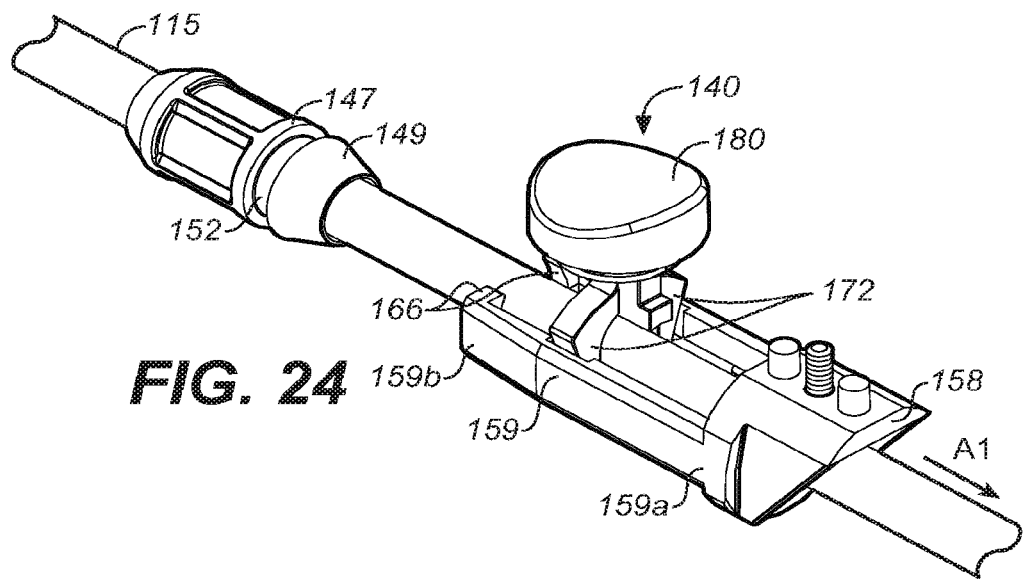
FIG. 24 is an oblique view of the inner core engagement assembly and the inner core, showing the inner core in a first, disengaged position relative to the inner core engagement assembly, other components of the delivery catheter being removed from this view for clarity.
Figure 25:
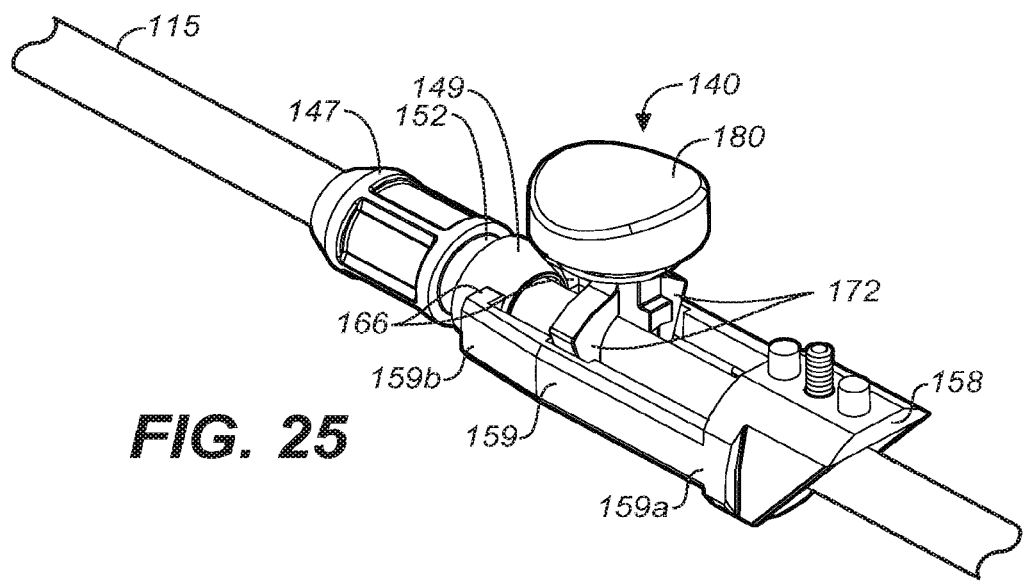
FIG. 25 is a cross-sectional view of a portion of the delivery catheter through the axial centerline of the delivery catheter, showing the inner core in the first, disengaged position relative to the inner core engagement assembly.
Figure 26:
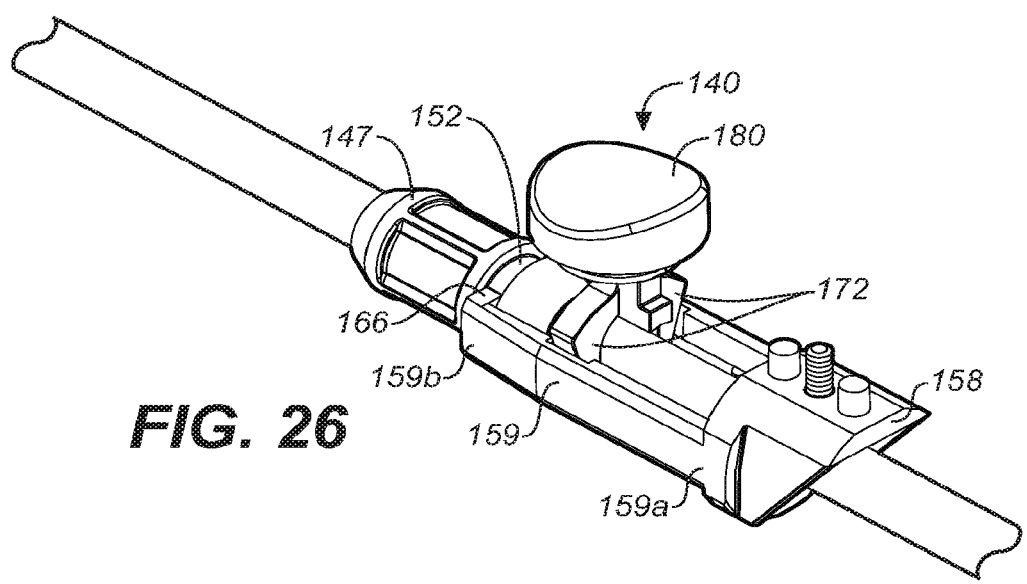
FIG. 26 is an oblique view of the inner core engagement assembly and the inner core as in FIG. 24, showing the inner core in a second, partially engaged position relative to the inner core engagement assembly.

The handle member 128 is selectively engageable with the inner core member 115. FIG. 24 is an oblique view of the inner core engagement assembly 139 and the inner core member 115, showing the inner core member 115 in a first, disengaged position relative to the inner core engagement assembly 139, other components of the delivery catheter being removed from this view for clarity. FIG. 25 is a cross-sectional view of a portion of the delivery catheter assembly 104 through the axial centerline of the delivery catheter assembly 104, showing the inner core member 115 in a first, disengaged position relative to the inner core engagement assembly 139. FIG. 26 is an oblique view of the inner core engagement assembly 139 and the inner core member 115 as in FIG. 24, showing the inner core in a second, partially engaged position relative to the inner core engagement assembly.

With reference to FIGS. 24-26, in some embodiments of the delivery catheter assembly 104, an engagement ring 147 is supported by the inner core member 115. The engagement ring 147 has a tapered fore surface 149 and a channel or depression 152 formed around an outside surface of the engagement ring 147. The fore surface 149 can have a generally frustoconical shape, and the channel 152 can be formed all around the engagement ring 147 forming a ring groove. The engagement ring 147 is adhered to, formed integrally with, or otherwise fastened to or supported by the inner core member 115 at any desired position along the length of the inner core member 115.

With reference to FIGS. 24-26, a body member 155 of the engagement assembly 139 supports one or more tabs or arms 159 configured to engage with the engagement ring 147. The one or more arms 159 can have inward facing tabs or projections 166 supported at the proximal end 159b of the one or more arms 159. The arms 159 are supported by the body member 155 in a cantilevered configuration so that the base portion 159a of the one or more arms 159 is fixed to the body member 155 and such that the proximal end portion 159b of the one or more arms 159 is unsupported. The arms 159 are supported by the body member 155.

Figure 27A:
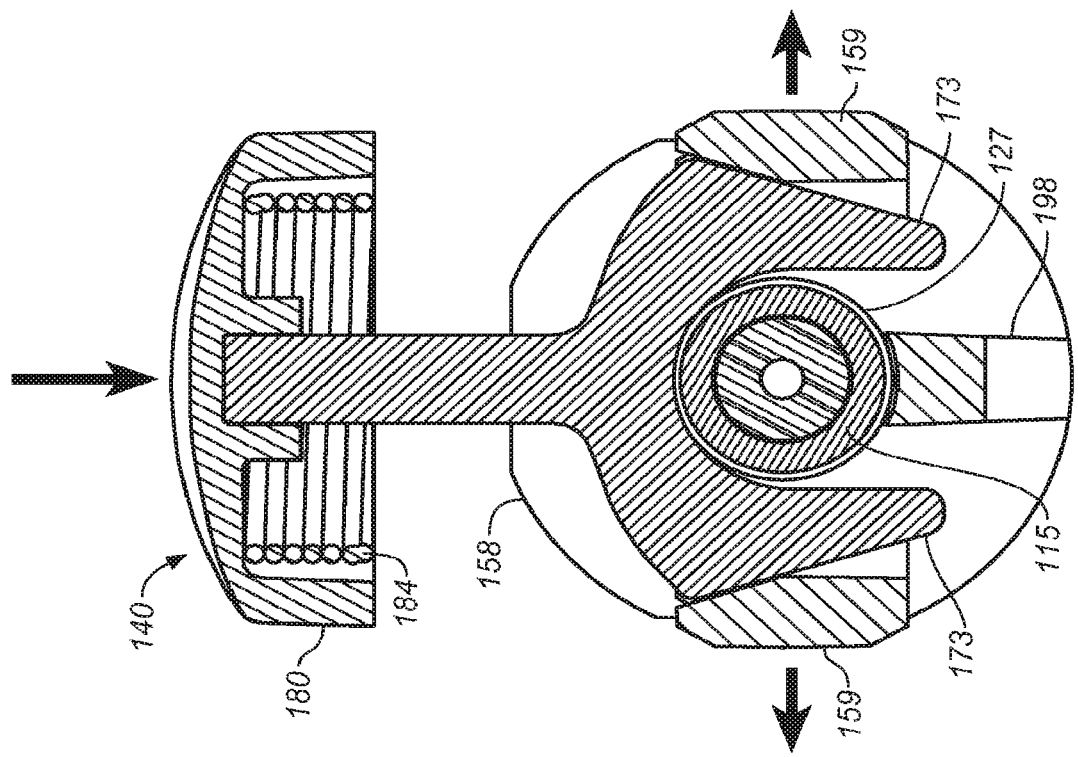
FIG. 27A is a cross-sectional view of a portion of the delivery catheter taken through the line 27A-27A of FIG. 29, showing one or more components of the delivery catheter in a first position.
Figure 30:
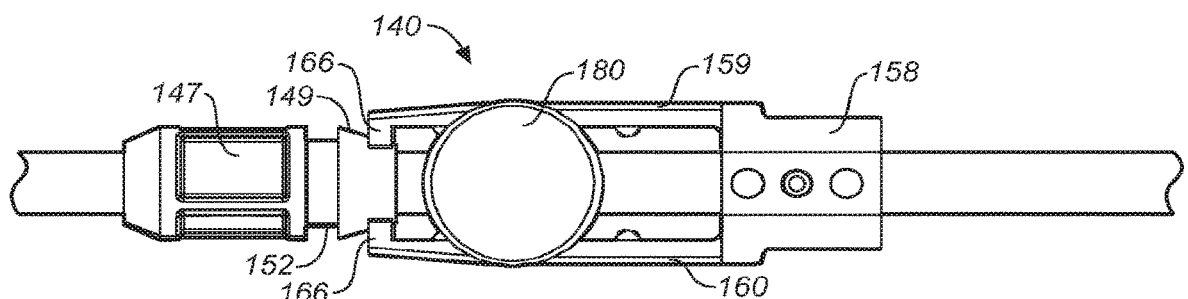
FIG. 30 is an oblique view of the inner core engagement assembly and the inner core as in FIG. 24, showing the inner core in a third, engaged position relative to the inner core engagement assembly.
Figure 31:
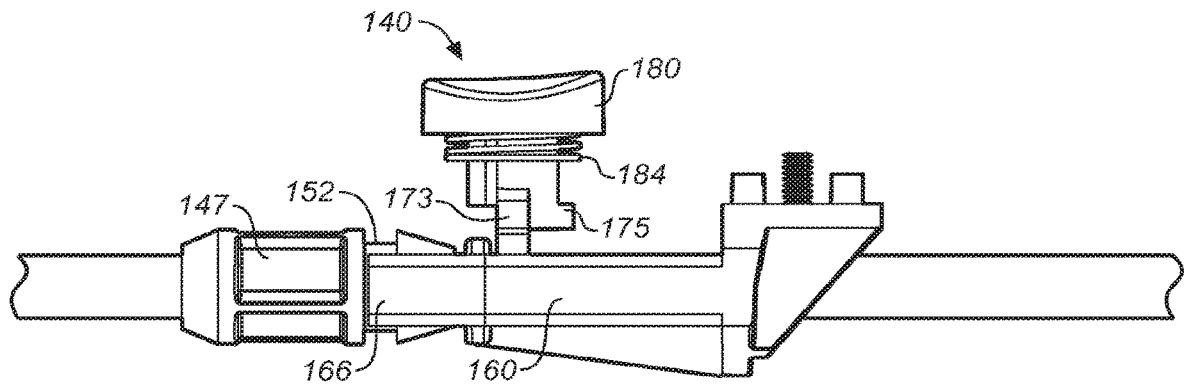
FIG. 31 is a side view of the inner core engagement assembly and the inner core as in FIG. 30, showing the inner core in the third, engaged position relative to the inner core engagement assembly.
Figure 32:
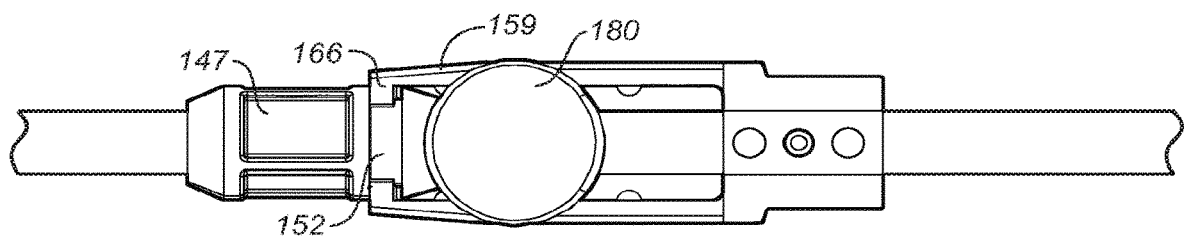
FIG. 32 is a top view of the inner core engagement assembly and the inner core as in FIG. 30, showing the inner core in the third, engaged position relative to the inner core engagement assembly.
Figure 33:
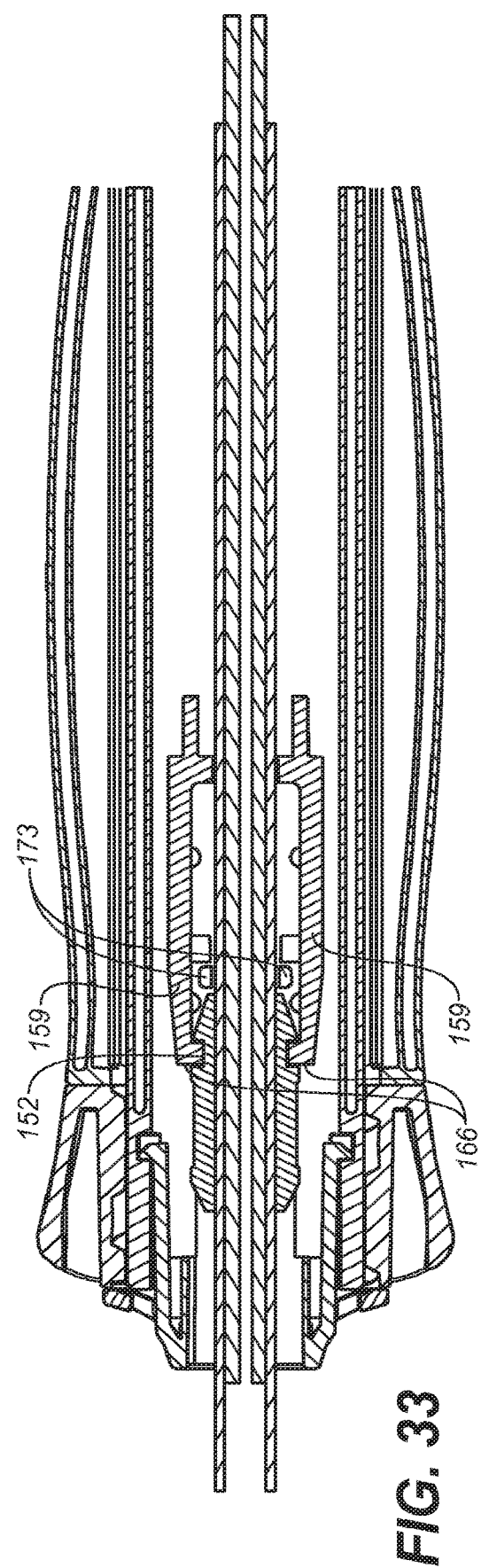
FIG. 33 is a cross-sectional view of a portion of the delivery catheter through the axial centerline of the delivery catheter, showing the inner core in the third, engaged position relative to the inner core engagement assembly.

The engagement ring 147 is configured to be received by the inner core engagement assembly 139 by sliding the inner core member 115 in a first (distal) direction (represented by arrow A1 in FIG. 24) until the engagement ring 147 is engaged with the engagement assembly 139. As illustrated in FIG. 26, as the inner core member 115 and engagement ring 147 are moved toward the engagement assembly 139, a tapered fore surface 149 of the engagement ring 147 causes the tabs or arms 163 spread apart as the engagement ring 147 is advanced into the engagement assembly 139, as illustrated in FIGS. 26-28. With further advancement of the inner core member 115 relative to the handle member 128, when the protruding portions 166 of the arms 159 are in axial alignment with the channel 152, the protruding portions 166 of the arms 159 can compress and shrink (spring) toward each other and into the channel 152 due to the bias of the one or more arms 159. As illustrated in FIGS. 30-32, the inner core member 115 is axially engaged with the handle member 128 until the user disengages the engagement assembly 139 from the engagement ring 147, the inner core member 115 can be freely rotated relative to the handle member 128 even when axially engaged with the handle member 128.

Figure 27B:
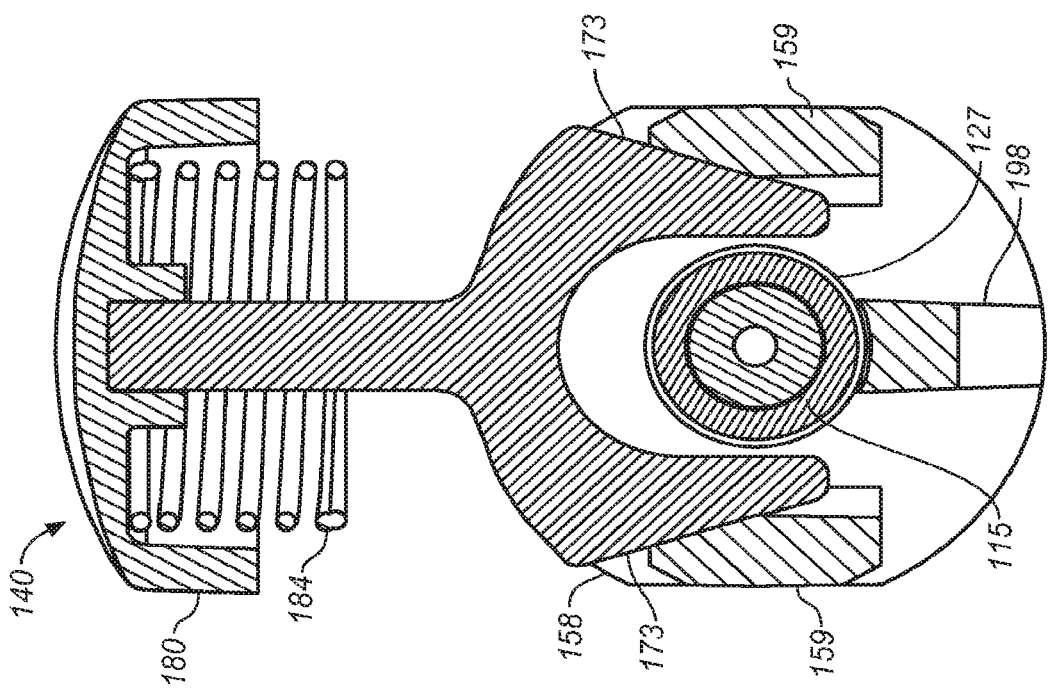
FIG. 27B is a cross-sectional view of a portion of the delivery catheter taken through the line 27A-27A of FIG. 29, showing one or more components of the delivery catheter in a second position.
Figure 29:
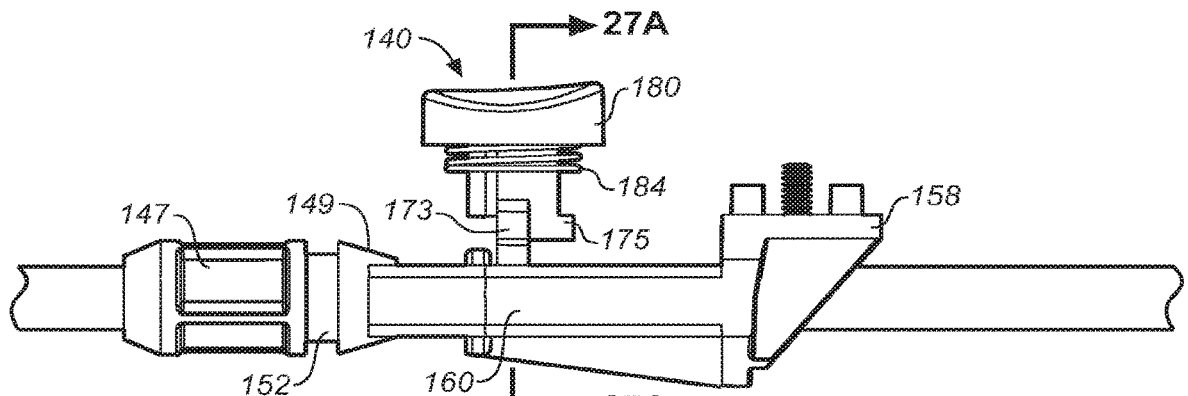
FIG. 29 is a cross-sectional view of a portion of the delivery catheter through the axial centerline of the delivery catheter, showing the inner core in a second, partially engaged position relative to the inner core engagement assembly.

The engagement assembly 139 is further configured so that moving the one or more arms 159 in a radial direction (spreading them, as shown in FIG. 27B) will cause the protruding portions 166 of the arms 159 to be lifted away from the channel 152 of the engagement ring 147. The one or more spread tabs 173 supported by a body portion 175 or configured to exert the necessary radial force (spreading) on the arms 159 to lift the protruding portions 166 away from the engagement ring 147. The spread tabs 173 can have a tapering shape such that, moving the spread tabs 173 in a downward direction relative to the one or more arms 159 deflects the arms 159 outward. Depressing button 180 forces the spread tabs 173 downward, thereby deflecting the arms 159 outward so that the engagement ring 147 is axially released and axially moved away from the engagement assembly 139.

FIG. 34 is a cross-sectional view of a portion of the delivery catheter through the axial centerline of the delivery catheter, showing the inner core member 115 in a disengaged position relative to the inner core engagement assembly 139.

FIG. 35 is a cross-sectional view of a portion of the delivery catheter assembly 104 through the axial centerline of the delivery catheter assembly 104, showing the inner core member 115 in an engaged position relative to the inner core engagement assembly 139. As illustrated therein, a biasing mechanism or spring member 184 is supported by the handle member 128 and is configured to bias the button 180 and, consequently, the spread tabs 175, in a first direction away from the inner core member 115.

Further, with reference to FIGS. 34-35, the handle member 128 has a stop member 198 configured to limit the range of motion of the engagement ring 147 and inner core member 115 relative to the handle member 128. For example, the first end portion 198a of the stop member 198 is configured to abut against a fore surface 149 of the engagement ring 147 when the engagement ring 147 is advanced into the handle member 128.

The stent can be preloaded in the introducer catheter assembly or introducer sheath such that the stent need not be transferred into the catheter assembly or introducer sheath during the surgical operation. The delivery catheter system can have an introducer sheath, inner core, and some or all of the other features of the delivery catheter disclosed herein in one apparatus. In of this inclusive apparatus, the inner core can be permanently joined to the handle member 128 such that there would be no need to configure the delivery catheter to be selectively engageable with the inner core, thereby simplifying the assembly and potentially simplifying the surgical procedures. Therefore, some embodiments of this inclusive delivery catheter assembly, the delivery catheter assembly can have all of the components, features, details, or configurations of the embodiments of the catheter system 100 described above, wherein the inner core engagement assembly 139 and the lock engagement ring 147 of the inner core member 115 can be replaced with a non-selectable coupling or other connection between the inner core member 115 and the handle member 128.

Figure 36:
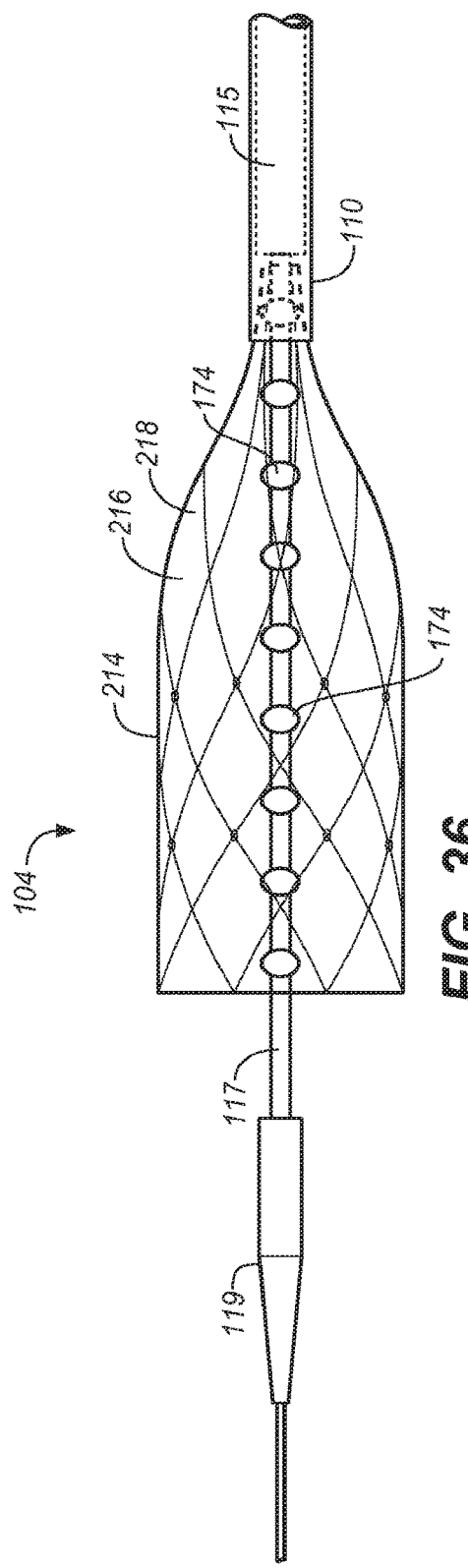
FIG. 36 is an illustration of a prosthesis partially deployed by the delivery catheter.
Figure 37:
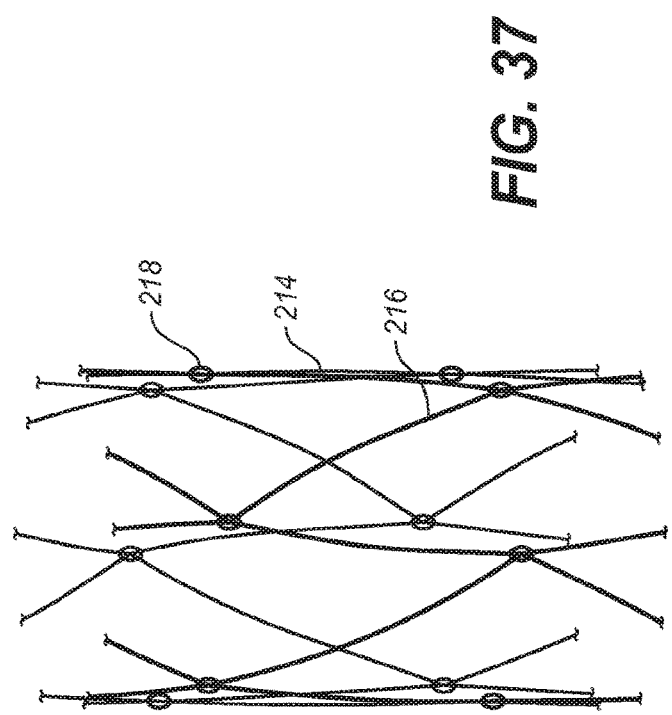
FIG. 37 is a side view of an exemplifying stent that can be deployed with the delivery catheter illustrated in FIG. 36.

FIG. 36 is an illustration of a prosthesis partially deployed by the delivery catheter assembly 104. FIG. 37 is a partial side view exemplifying a stent that can be deployed with the delivery catheter assembly 104. The deployment catheter illustrated in FIG. 36 can be adapted for deployment of any suitable prosthesis and is not limited to deployment of the stent illustrated in FIG. 37. With reference to FIGS. 20, 36, and 37, one or more beads or tabs 174 can be formed on or supported by the core wire 117. The tabs 174 can be configured to increase the axial support or connection between the inner core wire 117 and a stent 214 supported by the core wire 117 when the stent is supported in a compressed on the core wire 117. Additionally, the tabs 174 can be sized, spaced, and otherwise configured to provide axial support to multiple individual stent segments (not illustrated). For example, multiple independent or tethered stent segments can be positioned within a tubular or bifurcated graft or otherwise, and the stent can be positioned relative to the tabs 174 such that the tabs 174 are positioned between the stent segments 216 or between the apices, knuckles, or connection points 218 interconnecting the struts.

In the configuration shown, the beads or tabs 174 supported by the core wire 117 can engage the struts 216 or connection points 218 of the stent 214 to help prevent the stent from axially slipping relative to the inner core wire 117 for portions of the stent 214 that remain compressed within the outer sheath 110. This arrangement provides greater control over the stent 214 during the final stages of deployment of the stent 214, for example, when only an end portion of the stent 214 remains compressed within the outer sheath 110, as illustrated in FIG. 36.

Additionally, positioning the tabs 174 between the struts 216 or connection points 218 can reduce the compressed diameter or crossing profile of the compressed prosthesis, the outer sheath 110, and other components comprising the catheter system. This arrangement can also allow for a more uniform distribution of support forces between the tabs 174, the inner core wire 117, and the stent 214, the tabs 174 can be sized, spaced, and otherwise configured so as to be positioned adjacent to the links, bends, loops, and/or other connectors formed in a tubular or bifurcated stent, such as the links, bends, loops, and/or other connectors comprising the embodiments of the stents disclosed in U.S. Pat. No. 6,077,296, entitled ENDOLUMINAL VASCULAR PROSTHESIS, which patent is hereby incorporated by reference as if fully set forth herein.

In any of the catheter system embodiments disclosed herein, the catheter system can be configured as described herein such that the stent can be compressed from, a first diameter or size to a second diameter or size as the stent is being loaded into the introducer or introducer sheath. The first diameter or size can be the fully relaxed or expanded diameter of the stent, or the first diameter or size can be a partially compressed diameter. For example, for some of the embodiments disclosed herein, the stent can be compressed from a first diameter, as defined or controlled by the sheath of the delivery catheter or by an assembly apparatus surrounding the stent, to a second diameter, as defined or controlled by the introducer sheath. The reduction ratios of the stent when advanced into the introducer can be from approximately 50% to approximately 95%, meaning that the second diameter can be from approximately 50% to approximately 95% of the first diameter.

Figure 38:
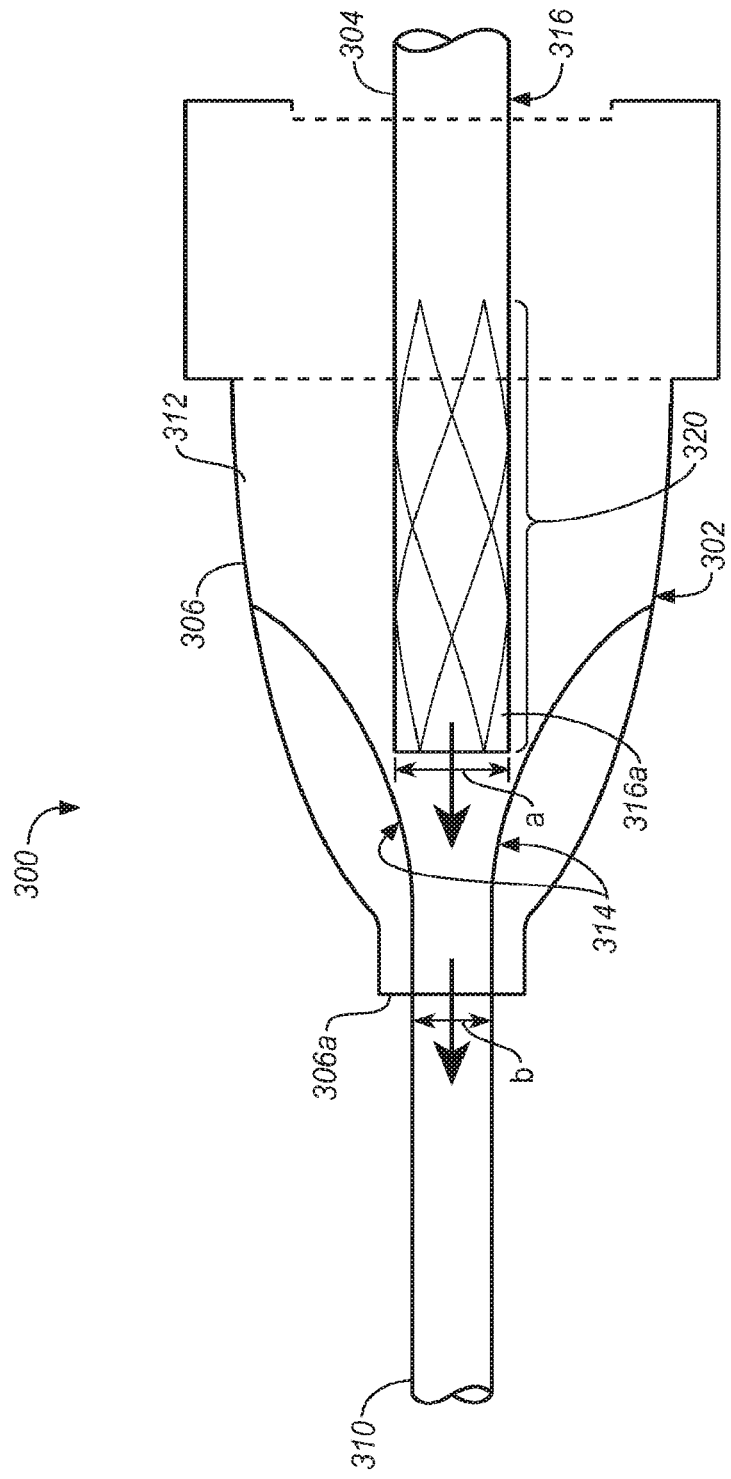
FIG. 38 is a schematic side view of a catheter system having an introducer catheter assembly showing a stent being loaded into an outer sheath of the introducer catheter.

FIG. 38 is a side view of a catheter system 300 having an introducer catheter assembly 302, showing a stent being loaded into an outer sheath of the introducer catheter assembly 302. Only a portion of the delivery catheter 304 is illustrated and certain features of the introducer catheter assembly 302 have been omitted for clarity. The catheter system 300 and/or the introducer catheter assembly 302 can have any of the components, features, materials, or other details of any of the embodiments of the catheter systems or introducer catheter assemblies disclosed or incorporated by reference herein, including U.S. application Ser. No. 12/496, 446, filed Jul. 1, 2009, entitled "CATHETER SYSTEM AND METHODS OF USING SAME." Further, the embodiments of the introducer catheter assembly 302 can be configured to work with any of the delivery catheter assembly embodiments disclosed or incorporated by reference herein.

With reference to FIG. 38, the introducer catheter assembly 302 can have a main body portion 306 and an outer sheath 310 supported at a distal end 306a of the main body portion 306. An inner aperture or opening 312 on the inside of the introducer catheter assembly 302 can be coaxial with the opening formed through the outer sheath 310, the introducer catheter assembly 302 can have tapered or curved wall portions 314 that are configured to compress the stent 320 from a first diameter "a" to a second diameter "b" that is equal to an inside diameter of the (introducer) outer sheath 310 as the stent 320 is being advanced through the introducer catheter assembly 302.

The introducer catheter assembly 302 and the delivery catheter can be configured such that the distal end 316a of the sheath 316 terminates prior to or approximately adjacent to the constricted portion of the main body portion 306. In this configuration, the stent can be loaded into the delivery catheter in a relaxed or mostly relaxed (i.e., expanded) state having diameter "a", and be compressed by the tapered wall portions 314 of the introducer catheter assembly 302 to a final, compressed diameter "b", thereby reducing the stresses applied to the stent prior to loading the stent in the introducer catheter assembly 302.

The sheaths supported by the delivery catheter, for example sheath 316 or the sheath 127 discussed above, can overlap or be advanceable into at least the proximal portion of the introducer or outer sheath 310, 110, or so that the sheath 316 or the sheath 127 discussed above can be advanceable through the entire length of the introducer or outer sheath 310, 110. A distal portion of the sheath supported by the delivery catheter can be tapered. In this configuration, the stent can be further compressed or compressed as it is being passed through the distal portion of the delivery catheter sheath into the introducer or introducer sheath.

The introducer catheter assembly 302 can be configured to receive and deploy any of a variety of prostheses, including non-bifurcated and bifurcated stents and stent grafts, stent segments, fenestrated stents, and other similar stents or stent grafts disclosed herein or otherwise, the introducer catheter assembly 302 or any other introducer catheter assembly embodiment disclosed herein can be configured to receive and removably couple with any of a variety of delivery catheters, including accessory stent catheters, suprarenal stents or stent extension catheters, or bifurcated stent delivery catheters.

The outer sheath 310 or any other outer sheath embodiment disclosed herein has an inner diameter of approximately 0.237 in, and an outer diameter of approximately 0.253 in. When used for the delivery of a bifurcated stent, the sheath 316 has an inner diameter of approximately 0.251 in, and an outer diameter of approximately 0.263 in. When used for the delivery of an accessory stent or non-bifurcated stent, the sheath 316 has an inner diameter of approximately 0.241 in. and an outer diameter of approximately 0.263 in.

When used for the delivery of a bifurcated stent, the inner core (not illustrated in FIG. 38) the catheter system has an outer diameter of approximately 0.212 in. When used for the delivery of a non-bifurcated stent, the inner core of any catheter system has an outer diameter of approximately 0.213 in.

FIG. 39 is a schematic side view of a catheter system 400 having a deployment catheter assembly 404 comprising an inner core 408, an outer sheath 410, a plurality of tabs 412 supported by a core wire 414 axially attached to the inner core 408, and a distal tip 415 axially attached to the core wire 414. A stent 416 is supported by the delivery catheter 404 and is surrounded by the outer sheath 410. The stent 416 is a self-expanding bifurcated stent, as herein illustrated, or can be any other stent or medical prosthesis disclosed or incorporated by reference herein or otherwise. The delivery catheter 404 can further comprise a branch vessel wire assembly 417 loaded in the delivery catheter 404.

FIG. 40 is a cross-sectional view of the branch vessel wire assembly 417 taken at line 40-40 of FIG. 39, and FIG. 41 is an enlarged schematic view of a portion of the branch vessel wire assembly 417 defined by curve 41-41, of FIG. 39. The branch vessel wire assembly 417 includes an inner wire 418 positioned at least partially within a hollow tube or guidewire 420. The branch vessel wire assembly 417, the inner wire 418, or the hollow tube 420 can have any of the sizes, features, materials, or other details of the dual concentric guidewire disclosed in U.S. application Ser. No. 11/623,022, filed Jan. 12, 2007, which is incorporated by reference as if fully set forth herein.

The hollow tube 420 can project through an inside lumen of the stent 416 such that a distal end 420a of the hollow tube 420 projects past an end portion 416a of the stent 416.

Additionally, the hollow tube 420 has a curved or kinked portion 420b proximal to the end of the stent 416. The outer sheath 410 holds the curved portion 420b of the hollow tube 420 in the curved position or orientation (the first state) so as to mechanically link or lock the inner wire 418 axially to the hollow tube 420 until the curve or bend in the curved portion 420b is relaxed. As will be discussed, the curve or bend in the curved portion 420b can be relaxed by retracting or withdrawing the outer sheath 410 past the curved portion 420b of the hollow tube 420, thereby allowing the hollow tube 420 and inner wire 418 to relax and straighten. Therefore, when the hollow tube 420 is in the first state, the inner wire 418 will be axially fixed to the hollow tube 420 such that the inner wire 418 is axially retracted without becoming disengaged from the hollow tube 420. When the outer sheath 410 is retracted past the curved portion 420b of the hollow tube 420, the hollow tube 420 relaxes so that the curved portion 420b is no longer be axially locked to the inner wire 418. In this second, relaxed state, the inner wire 418 can be axially advanced or retracted into and out of the hollow tube 420.

In this arrangement, the inner wire 418 can be advanced through a first puncture site in a first branch vessel or passageway (such as the ipsilateral iliac artery) and then withdrawn though a second branch vessel or passageway (such as the contralateral iliac artery), using any suitable cross-over techniques. For example, the inner wire can be advanced through the ipsilateral iliac artery in a slitted lumen formed in a dual lumen dilator. The dilator can be withdrawn and set aside, allowing the inner wire 418 to pass through the slit in the lumen of the dual lumen dilator, thereby leaving a proximal end of the inner wire 418 positioned within the abdominal aorta. In this position, the inner wire 418 can be snared and retracted through the contralateral iliac artery and through a second puncture site.

Many embodiments of the catheter system have been described in connection with the accompanying figures. It will apparent to one of ordinary skill in the art that there are many potential embodiments of the catheter system that may be suitable for medical use and which are contemplated herein. For example, any of the components or features of some embodiments of the catheters disclosed herein or other catheters available in the field can be combined to form additional embodiments, all of which are contemplated herein.

While the above description has shown, described, and pointed out features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure. Further, as will be recognized, certain embodiments described herein may be embodied within a form that does not provide all of the features and benefits set forth herein, as some features may be used or practiced separately from others.

What is claimed is:

1. A system comprising:
   a main body;
   a delivery catheter sheath projecting distally from a distal end portion of the main body; and
   a handle member supported by the main body, wherein the handle member is axially moveable along the main body by axially sliding the handle member relative to the main body, and wherein the main body comprises a slot configured to receive a protruding portion of the handle member.

2. The system of claim 1, further comprising external threads along a portion of the main body.

3. The system of claim 2, wherein the external threads extend along approximately 40% to approximately 70% of a length of the main body.

4. The system of claim 1, wherein the handle member does not rotate relative to the main body.

5. The system of claim 1, wherein the main body slideably receives the handle member.

6. A system comprising:
a main body having a proximal end portion and a distal end portion;
an inner core axially advanceable through the main body; and
a handle member supported by the main body of a delivery catheter, the handle member being axially moveable along the main body, wherein the inner core is axially moveable by axially sliding the handle member relative to the main body; and wherein the inner core is selectively engageable by the handle member.

7. The system of claim 6, further comprising external threads along a portion of the main body.

8. The system of claim 7, wherein the external threads extend along approximately 40% to approximately 70% of a length of the main body.

9. The system of claim 6, wherein the handle member does not rotate relative to the main body.

10. The system of claim 6, wherein the main body slideably receives the handle member.

11. A system comprising:
a main body having a proximal end portion and a distal end portion;
an inner core axially advanceable through the main body; and
a handle member supported by the main body, the handle member being axially moveable along the main body;
wherein the inner core is axially moveable by axially sliding the handle member relative to the main body; and
wherein the inner core is rotatable relative to the handle member.

12. The system of claim 11, wherein the inner core comprises a core wire and a plurality of tabs are spaced axially along at least a portion of the core wire.

13. The system of claim 11, wherein the handle member is axially moveable along the main body by axially sliding the handle member relative to the main body.

14. The system of claim 11, further comprising external threads along a portion of the main body.

15. The system of claim 14, wherein the external threads extend along approximately 40% to approximately 70% of a length of the main body.

16. The system of claim 11, wherein the main body slideably receives the handle member.

17. A system comprising:
a main body having a proximal end portion and a distal end portion;
an inner core axially advanceable through the main body;
a handle member supported by the main body, the handle member being axially moveable along the main body; and
wherein the inner core is axially moveable by axially sliding the handle member relative to the main body
wherein the handle member does not rotate relative to the main body.

18. The system of claim 17, wherein the inner core is rotatable relative to the handle member.

* * * * *